(12) United States Patent
Phillips et al.

(10) Patent No.: US 6,511,512 B2
(45) Date of Patent: Jan. 28, 2003

(54) ACTIVE SHOCK MODULE PROSTHESIS

(75) Inventors: Van L. Phillips, P.O. Box 1873, Rancho Santa Fe, CA (US) 92067; Hilary D. Pouchak, Carlsbad, CA (US)

(73) Assignees: Ossur Hf (IS); Van L. Phillips, Albion, CA (US)

( * ) Notice: Subject to any disclaimer, the term of this patent is extended or adjusted under 35 U.S.C. 154(b) by 0 days.

(21) Appl. No.: 09/556,249

(22) Filed: Apr. 24, 2000

(65) Prior Publication Data

US 2002/0177906 A1 Nov. 28, 2002

Related U.S. Application Data

(63) Continuation-in-part of application No. 09/289,533, filed on Apr. 9, 1999
(60) Provisional application No. 60/081,282, filed on Apr. 10, 1998.

(51) Int. Cl.$^7$ .............................. A61F 2/74; A61F 2/80
(52) U.S. Cl. ........................................ 623/27; 623/35
(58) Field of Search ............................. 623/27, 35, 38

(56) References Cited

U.S. PATENT DOCUMENTS

| | | | |
|---|---|---|---|
| 49,528 A | 8/1865 | Jewett | |
| 53,931 A | 4/1866 | Weston et al. | |
| 61,780 A | 2/1867 | Watson | |
| 277,562 A | 5/1883 | Furrer | |
| 809,875 A | 1/1906 | Wilkins | |
| 817,340 A | 4/1906 | Rosenkranz | |
| 827,720 A | 8/1906 | Erwin | |
| 1,424,264 A | 8/1922 | Shrodes | |
| 1,804,915 A | 5/1931 | Collins | |
| 2,480,856 A | 9/1949 | Henschke et al. | |
| 2,578,019 A | 12/1951 | Ryan | |
| 2,619,652 A | 12/1952 | Vesper | |
| 2,692,392 A | 10/1954 | Bennington et al. | |

(List continued on next page.)

FOREIGN PATENT DOCUMENTS

| | | | |
|---|---|---|---|
| AT | 194822 | 3/1997 | |
| AU | 179844 | 10/1954 | .................. 623/38 |
| AU | 658687 | 4/1995 | |
| CA | 2119926 | 12/1996 | |
| DE | 328017 | 2/1919 | |
| DE | 196 42 719 A1 | 4/1997 | |
| EP | 0 738 837 | 10/1996 | |
| EP | 0 606 383 | 3/1997 | |
| FI | 941453 | 5/1994 | |
| FR | 2501999 | 9/1982 | .................. 623/38 |
| FR | 2567395 | 1/1986 | .................. 623/27 |
| GB | 2 305 363 A | 4/1997 | |
| GR | 3023230 | 7/1997 | |
| JP | 8-280870 | 10/1996 | |
| JP | 8-284995 | 11/1996 | |
| SU | 605613 | 5/1978 | .................. 623/51 |
| SU | 1465046 | 3/1989 | .................. 623/47 |
| WO | WO 93/06795 | 4/1993 | |

OTHER PUBLICATIONS

Article entitled: "Titanium Elastic Properties and Applications" from Springs, Oct. 1987.
Article entitled: "Titanium Alloy Springs" from Springs, May 1988.
Brochure entitled: MaxLife Die Springs, Dayton Progress Corporation.

Primary Examiner—Corrine McDermott
Assistant Examiner—William H Matthews
(74) Attorney, Agent, or Firm—Knobbe, Martens, Olson & Bear LLP

(57) ABSTRACT

An impact-absorbing shock module comprises two pylons telescopingly engaged to permit axial and rotational motion therebetween. A resilient element, such as a spring-fluid combination, a plurality of interconnected disks, or a Belleville spring, provides axial shock absorption. A tubular torque-resisting cuff provides rotational resistance, or torsion-resistance. A fluid valve is optionally provided so that the fluid pressure may be varied to adjust the torsion resistance.

28 Claims, 38 Drawing Sheets

U.S. PATENT DOCUMENTS

| | | |
|---|---|---|
| 2,699,554 A | 1/1955 | Comelli |
| 2,899,685 A | 8/1959 | Bourcier de Carbon |
| 3,663,967 A | 5/1972 | Vermillion |
| 3,707,731 A | 1/1973 | Morgan |
| 3,784,988 A | 1/1974 | Trumpler |
| 3,800,333 A | 4/1974 | Friberg |
| 3,800,334 A | 4/1974 | Friberg |
| 3,906,552 A | 9/1975 | Weber |
| 4,074,542 A | 2/1978 | Hankosky et al. |
| 4,089,072 A | 5/1978 | Glabiszewski |
| 4,128,903 A | 12/1978 | Marsh et al. |
| 4,161,042 A | 7/1979 | Cottingham et al. |
| 4,177,525 A | 12/1979 | Arbogast et al. |
| 4,216,550 A | 8/1980 | Thompson |
| 4,268,922 A | 5/1981 | Marsh |
| 4,328,594 A | 5/1982 | Campbell et al. |
| 4,370,761 A | 2/1983 | Serri |
| 4,461,045 A | 7/1984 | Shorter et al. |
| 4,463,459 A | 8/1984 | Shorter et al. |
| 4,555,817 A | 12/1985 | McKendrick |
| 4,619,660 A | 10/1986 | Christiansen et al. |
| 4,636,220 A | 1/1987 | Ziegelmeyer |
| 4,883,493 A | 11/1989 | Martel et al. |
| 4,883,494 A | 11/1989 | Cooper |
| 4,938,777 A | 7/1990 | Mason et al. |
| 4,972,920 A | 11/1990 | Zamitter et al. |
| 4,994,086 A | 2/1991 | Edwards |
| 5,019,109 A | 5/1991 | Voisin |
| 5,030,239 A | 7/1991 | Copes |
| 5,071,435 A | 12/1991 | Fuchs et al. |
| 5,116,383 A | 5/1992 | Shorter et al. |
| 5,376,133 A | 12/1994 | Gramnas |
| 5,405,411 A | 4/1995 | McCoy |
| 5,458,656 A | 10/1995 | Phillips |
| 5,509,936 A | 4/1996 | Rappoport et al. |
| 5,702,488 A | 12/1997 | Wood et al. |
| 5,720,474 A | 2/1998 | Sugiyama |
| 5,800,562 A | 9/1998 | Wilkinson |
| 5,800,563 A | 9/1998 | Arbogast et al. |
| 5,888,214 A | 3/1999 | Ochoa |
| 5,984,972 A | 11/1999 | Huston et al. |
| 6,120,547 A | 9/2000 | Christensen |

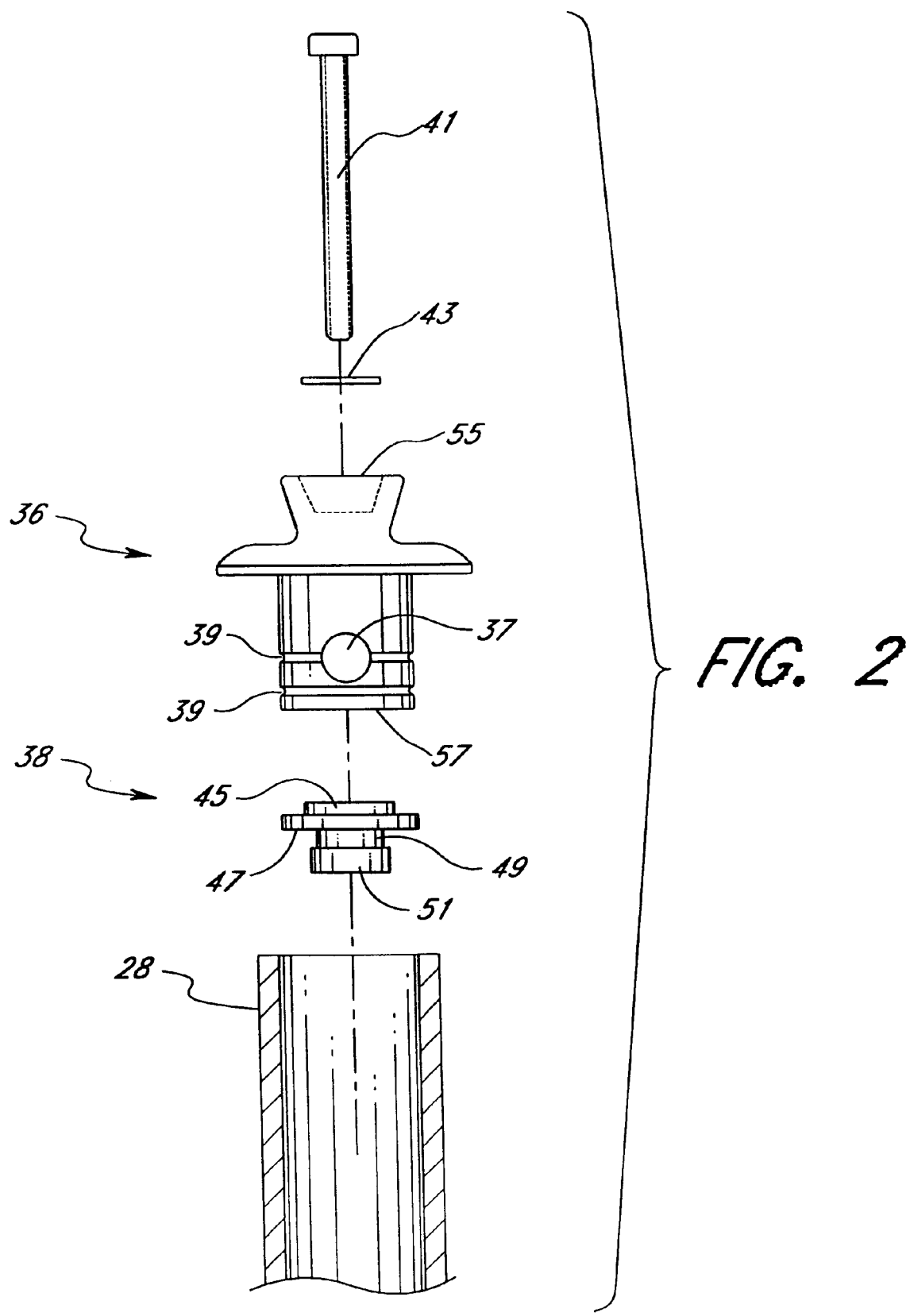

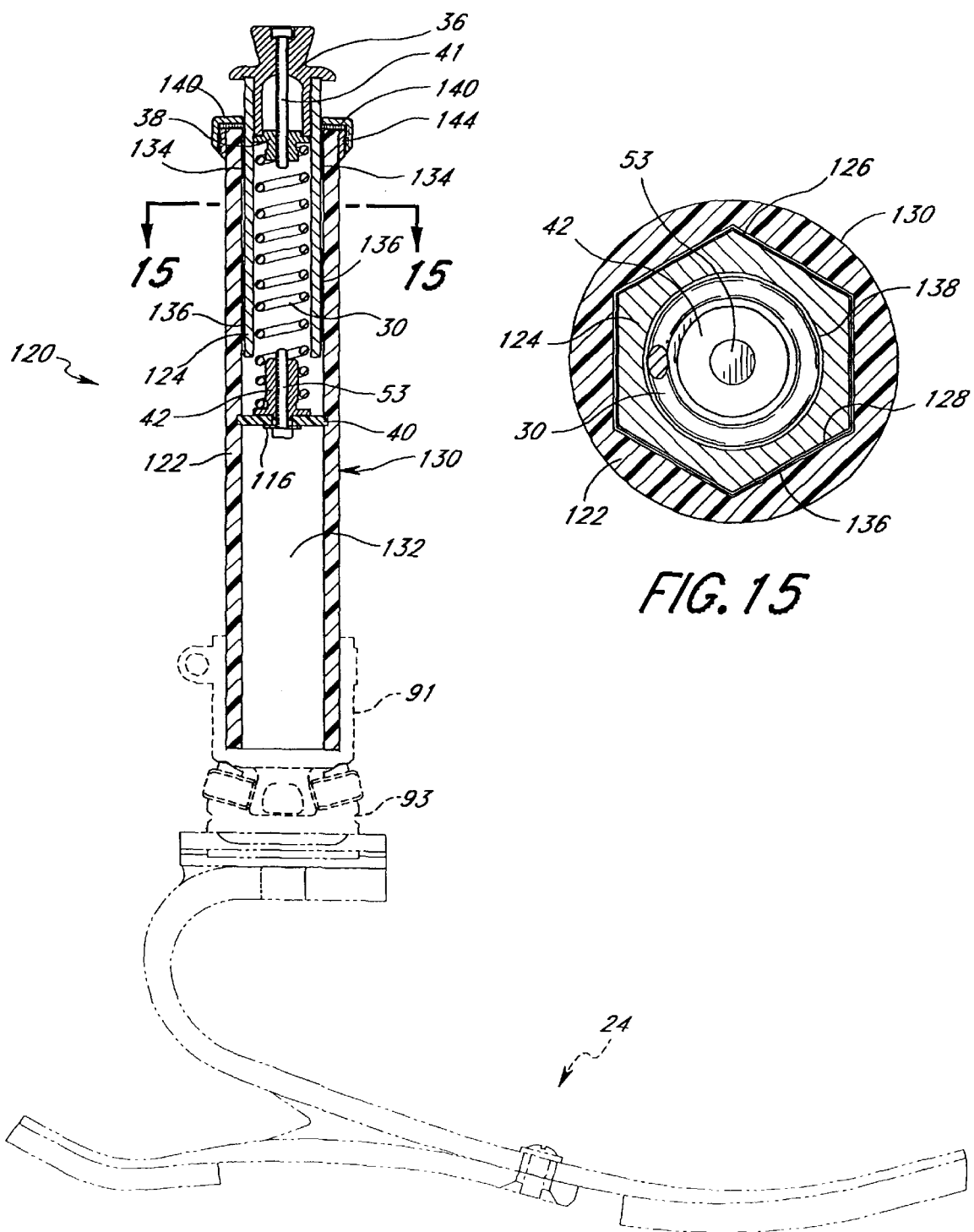

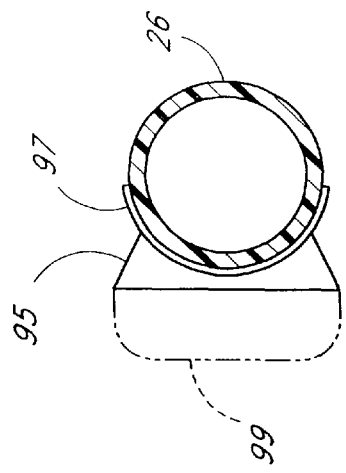
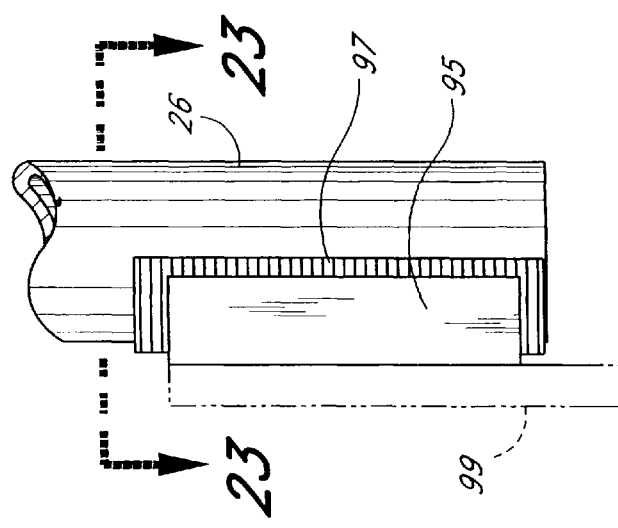
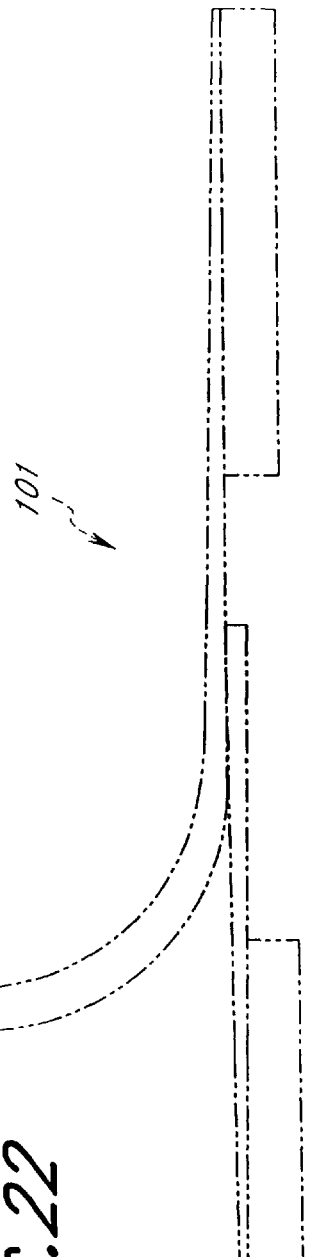

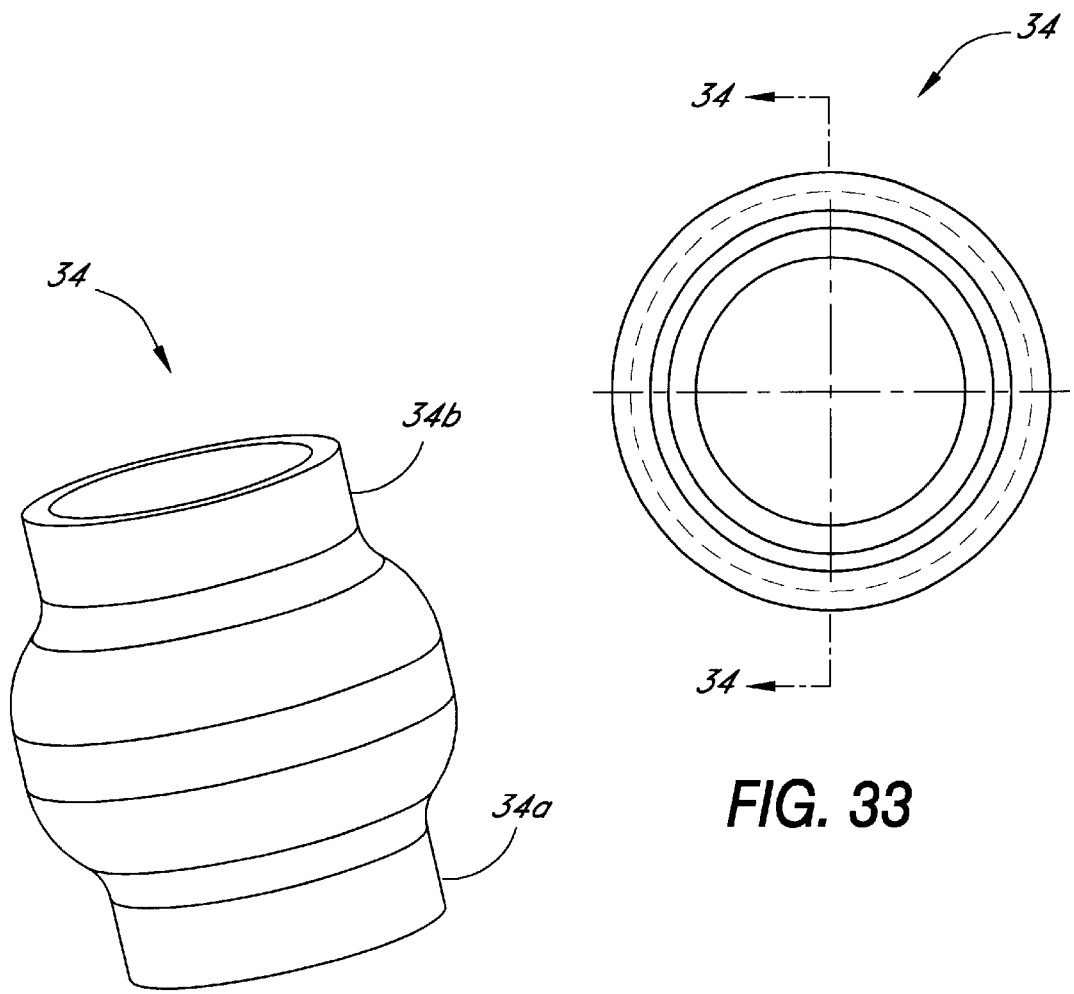
FIG. 32
FIG. 33
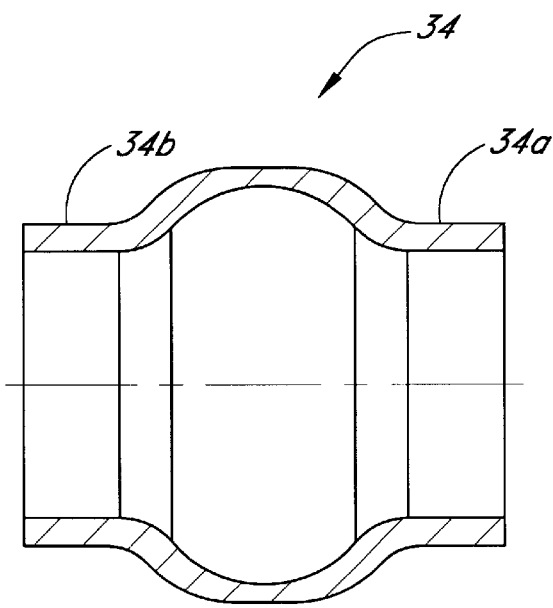
FIG. 34

FIG. 45
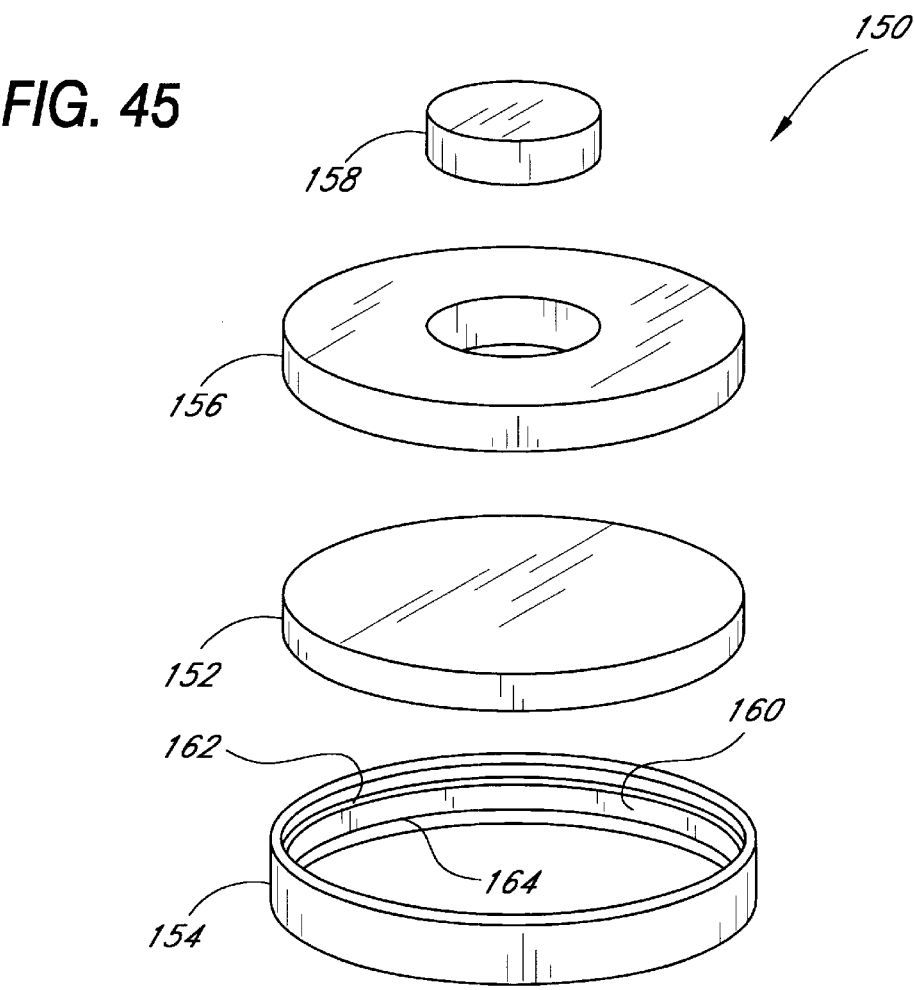
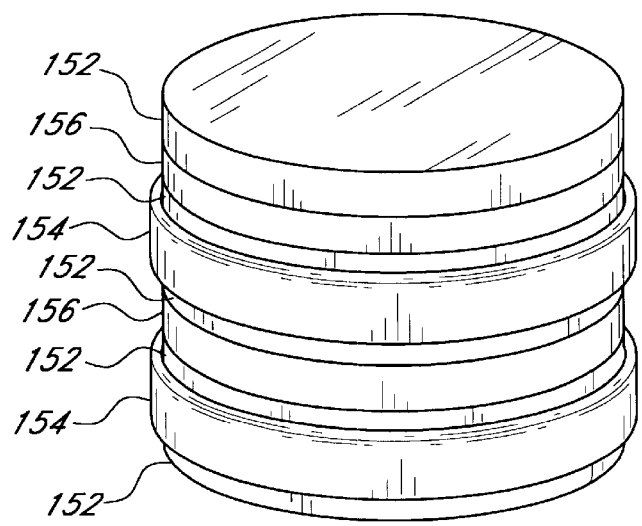

ACTIVE SHOCK MODULE PROSTHESIS

CROSS-REFERENCE TO RELATED APPLICATION

This application is a continuation-in-part of application Ser. No. 09/289,533, filed Apr. 9, 1999, the entirety of which is hereby incorporated by reference, which claims the benefit of U.S. Provisional Application Ser. No. 60/081,282, filed Apr. 10, 1998.

BACKGROUND OF THE INVENTION

1. Field of the Invention

The present invention relates to lower limb prostheses in general, and, in particular, to a shock module prosthesis having a spring and/or fluid resilient element for smooth impact absorption during use of the prosthesis, and also having an adjustable torque-resisting cuff permitting rotational compliance of the lower leg and foot.

2. Description of the Related Art

Various types of lower limb prostheses are known in the prior art. Such devices generally include some form of attachment for coupling the device to the dorsal end of the limb and a leg and/or foot member extending to the ground to support an amputee's weight. These devices generally attempt to simulate the structure and/or the performance of the human leg and foot.

Among the features desirable in a lower limb prosthesis is the incorporation of some means for providing impact absorption and/or dampening during use of the prosthesis, without sacrificing the ability to reliably and predictably support the amputee's body weight. Such impact absorption permits the amputee to participate in activities with comfort and minimal stump trauma, hence allowing the amputee to be mobile for longer periods of time. Also desirable is a convenient means to selectively adjust the degree of impact absorption to suit the particular attributes (e.g., weight) and activity (e.g., walking, running, jumping, etc.) of the amputee.

Impact absorption or, alternatively, shock absorption is normally achieved by the utilization of some form of resilient means, such as a spring, a member fabricated from a resilient material, or a compressible fluid. It should be understood that impact absorption in a prosthesis is simultaneously accompanied by energy absorption/storage and eventually energy release. Such energy release during use of the prosthesis usually aids in forward motion by providing lift and thrust forces to the foot region, thereby permitting the amputee to expend less energy.

Impact absorption in lower limb prostheses is typically achieved by utilizing two or more elongated telescoping members with a resilient means disposed therebetween. Axial forces acting on such members cause relative axial or, alternatively, longitudinal motion between them, with the resilient means providing energy storage and release. Furthermore, optimal performance of such prostheses occurs when there is maintained between these members a smooth relative motion. Unfortunately, a limitation of many such devices is that dirt, debris, and other such particles are free to enter the interface between the telescoping members and upset the smoothness of their relative motion. Thus, it is desirable to incorporate a means for restricting such entrance of dirt, debris, and other particles.

Another desirable feature of lower limb prostheses is the incorporation of some means for allowing rotational compliance of the lower leg and foot relative to the stump of the amputee. Such rotation is beneficial and simulates the action of a natural human knee/ankle in a number of activities that involve the twisting of a person's body with respect to their planted foot, such as golf, tennis, and the like. Rotational compliance in lower limb prostheses is typically achieved by utilizing telescoping members as described above, wherein the interface between such members is cylindrical, permitting them to rotate with respect to each other. However, unrestrained compliance is undesirable, as the foot would be free to twist unnaturally. Thus, it is desirable to incorporate a means for providing torsion-resistance against the rotation of the lower leg and foot relative to the stump of the amputee, and for returning the foot to its natural forward orientation after each rotational movement. Also desirable is a means for selectively adjusting the degree of torsion-resistance, to suit the particular attributes and activity level of the amputee.

The prior art describes many energy storing prostheses which utilize resilient means to cushion impact forces and/or to accentuate the amputee's movements. An example is U.S. Pat. No. 4,883,493 to Martel et al. which illustrates a lower limb prosthesis comprising a pre-loaded heavy duty coil spring and a damper piston mounted between telescoping shafts, using air as a compressible damping fluid. Although this prosthesis provides impact absorption, it encompasses several limitations. One limitation is that the pre-loaded spring provides for a jarring effect at foot/ground contact and a hard stop at spring extension. Such impact shocks may be tolerable to an athlete during running but are unreasonably uncomfortable for an ambulatory amputee. Another limitation is that the bolt-slot assembly restricts any rotational motion of the lower leg and foot. Another limitation is that the prosthesis utilizes the bolt-slot assembly to maintain the vertical position of the damper piston as the stump-supporting shaft vertically oscillates. As a result, the bolt experiences high shear stress caused by the pressure exerted against the damper piston by the compressed air during energy release and thrust. Moreover, the bolt is also vulnerable to shear stress associated with the twisting of the amputee's body with respect to their planted foot, as described above. These undesirable stresses adversely influence the performance of the prosthesis and necessitate frequent maintenance thereof. Yet another limitation is that there is no means for keeping atmospheric debris from entering the interface between the shafts, necessitating frequent disassembling and cleaning.

An example of a prosthesis which provides impact absorption, rotational compliance, and torsion-resistance is set forth in U.S. Pat. No. 5,458,656 to Phillips. In the preferred embodiment of this invention two telescoping cylindrical pylon members are connected by one or more elongated leaf spring elements, Normal and torsional forces imposed on the pylon members cause relative motion therebetween. A corresponding storage/release of energy in the leaf spring element(s) concurrently provides both impact absorption and torsion-resistance. The storage of energy associated with impact absorption is provided by an outward flexure of the leaf spring element(s). In contrast, the storage of energy associated with torsion-resistance is provided by a twisting of the leaf spring element(s).

Although the prosthesis of Phillips '656 utilizes a highly adaptable and effective design, it is very expensive to manufacture and has several characteristics that limit its clinical efficacy. One characteristic is that in order to vary the degrees of impact absorption and torsion-resistance the amputee must replace the leaf spring element(s), which is somewhat inconvenient. Another characteristic is that axial and torsional forces can cause excessive bending and twisting of the leaf spring element(s) which can create local regions of undesirably high stress. Another characteristic is that the outward flexure of the spring element(s) results in a larger effective width profile for the prosthesis, which can make cosmetic finishing more difficult. Yet another characteristic is that there is no means disclosed for keeping atmospheric debris from entering the interface between the pylon members.

A more recent U.S. Pat. No. 5,702,488 to Wood et al. describes another prosthesis that provides impact absorption, rotational compliance, and torsion-resistance. Impact absorption is provided via compression of a compressible volume of fluid which is enclosed between a piston head and cylindrical piston chamber. Torsion-resistance is provided by four resilient cushions that impede the rotation of a torsion key attached to the piston head.

Unfortunately, there are a variety of limitations associated with the prosthesis illustrated by Wood '488. One limitation is that it has a complex design, including the placement of an O-ring seal, a wear ring, two O-ring bumpers, and a retainer block within the interface between the telescoping piston head and piston chamber. This design translates into a heavier, expensive prosthesis that requires high maintenance and frequent adjustment. Another limitation is that torsion forces applied to the prosthesis result in local regions of undesirably high stress in the torsion key, which necessitates frequent maintenance. Another limitation is that the compressible fluid, by itself, provides less impact absorption than other prostheses. Another limitation is that there is no means for varying the torsion-resistance of the prosthesis, except for replacing the resilient cushions, which is inconvenient and cumbersome. Yet another limitation is that there is no means for keeping atmospheric debris from entering the interface between the piston head and piston chamber.

Of course, other shock absorbing means in prostheses simply induce a cushioning effect by utilizing strategically placed resilient materials, such as, for example, lubber in a prosthetic foot, socket liner, or stump socket. Those of ordinary skill in the art will readily comprehend that such cushioning means are of limited effectiveness and can only serve in a secondary capacity. Also, such shock absorbing means are typically integral with the foot or socket/liner and thus cannot be used with other prosthetic feet in a modular manner.

Thus, although the prior art illustrates many impact absorbing prostheses, none provide the benefits of selectively adjustable impact absorption, rotational compliance, conveniently adjustable torsion-resistance, and a means for preventing debris from entering and upsetting the smoothness of the relative motion of telescoping members, all in a relatively simple but highly effective construction which may be utilized in combination with a broad selection of prosthetic feet and sockets in a modular manner.

SUMMARY OF THE INVENTION

Accordingly, it a principle object and advantage of the present invention to overcome some or all of these limitations and to provide an improved shock-absorbing lower limb prosthesis.

In accordance with one embodiment, the present invention provides an impact and torque absorbing prosthetic shock module comprising an outer pylon, an inner pylon telescopingly engaged with said outer pylon so that an annular interface is formed between the pylons, a resilient element resisting relative axial displacement of the pylons, and a torque-resisting cuff providing torsional resistance to relative rotational motion between the pylons. The inner pylon is adapted to move axially and rotationally with respect to the outer pylon.

In accordance with another embodiment, the present invention provides an impact and torque absorbing prosthetic shock module comprising an elongated upper pylon, an elongated lower pylon adapted to move axially and rotationally with respect to the upper pylon, a resilient element resisting relative axial displacement of the pylons, and a torque-resisting cuff providing torsional resistance to relative rotational motion between the pylons. The longitudinal axes of the upper and lower pylons are maintained in a generally colinear alignment.

In accordance with another embodiment, the present invention provides a shock absorbing prosthesis comprising an upper support member, a lower support member, and a flexible tubular member. The upper and lower support members are coaxially and slidably supported relative to one another. The flexible tubular member is secured between the upper and lower support members so as to provide resistance to relative rotation between the upper and lower support members.

In accordance with another embodiment, the present invention provides an impact absorbing lower limb prosthesis comprising an outer tube, an inner shaft, and a coil spring. The outer tube has a longitudinal interior, a proximal end and a distal end. The longitudinal interior has a polygonal cross-section along at least a section of its span. The distal end is attachable to a prosthetic foot. The outer tube houses a support within its interior. The inner shaft has a proximal end, a distal end, and a longitudinal cavity. The proximal end is attachable to a socket for receiving a stump of an amputee. The inner shaft has a polygonal outer cross-section that is closely enveloped by at least a portion of the section of the longitudinal interior of the outer tube. The inner shaft is mounted to move axially with respect to the outer tube. The coil spring has an upper portion residing in the longitudinal cavity of the inner shaft and an upper end fixed in position relative to the inner shaft. The coil spring has a lower end attached such that the lower end is fixed in position relative to the outer tube. The coil spring is capable of a smooth response to loading and unloading via compression and extension, the compression and extension of the coil spring controlling relative motion between the outer tube and the inner shaft. The loading/unloading characteristics of the prosthesis to vertical compressive loads may be adjusted according to the particular weight of the amputee by selectively varying the spring characteristics of the coil spring.

In accordance with another embodiment, the present invention provides an impact absorbing lower limb prosthesis comprising an outer tube, an inner shaft having a hollow interior and being reciprocatingly interfitted with the outer tube, and a resilient means operatively attached to or disposed between the outer tube and the inner shaft, The resilient means is provided by an internal coil spring that is free of pre-loading stress so as to provide a smooth or non-jarring compression initiation and a smooth or non-jarring extension termination. The prosthesis simulates a shock absorber when subjected to vertical compressive loads.

In accordance with another embodiment, the present invention provides an impact and torque absorbing prosthetic shock module comprising an outer pylon having a proximal end and a distal end, the outer pylon having at least one internally threaded surface, and an inner pylon having a proximal end and a distal end telescopingly engaged with the outer pylon so that an annular interface is formed between the pylons. The inner pylon is adapted to move axially and rotationally with respect to the outer pylon. A resilient element is provided within the inner pylon having a proximal end and a distal end and being sized and configured to resist relative axial displacement of the pylons. A torque-resisting cuff connected to the pylons provides torsional resistance to relative rotational motion between the pylons.

In another embodiment, the present invention provides an impact and torque absorbing prosthetic shock module comprising an elongated upper pylon and an elongated lower pylon adapted to move axially and rotationally with respect to the upper pylon. At least one of the upper and lower pylons has an internally threaded surface. A resilient element having a proximal end and a distal end resists relative axial displacement of the pylons. A support member is threadingly engaged with the internally threaded surface, the support member providing a base for supporting one of the ends of the resilient element. The longitudinal axis of the upper pylon and the longitudinal axis of the lower pylon are maintained in a generally colinear relationship.

In another embodiment, the impact and torque absorbing prosthetic shock module comprises a first pylon having a proximal end and a distal end, and a second pylon having a proximal end and a distal end. A resilient element comprising a plurality of interconnected disks is also provided, the resilient element having a first end connected to the first pylon and a second end connected to the second pylon.

In another embodiment, the present invention relates to an improved lower limb prosthesis which comfortably reduces impact or shock forces upon the stump of an amputee resulting from a variety of activities ranging from passive to strenuous. A vertical shock absorbing prosthesis constructed in accordance with the present invention is detachably positioned between a prosthetic foot member and a prosthetic knee or a socket for receiving the stump of an amputee. Preferably, a substantially rigid inner pylon is slidably received within a substantially rigid outer pylon. A compression member or assembly having predetermined load-deflection characteristics is contained within the pylons and provides increased comfort for the amputee during both normal and impact loading on the lower limb.

During a normal walking motion, a person's gait or stride results in a cycle of compression and decompression of the lower limb, as contact with the ground transmits forces or loads upward toward the torso. In accordance with the present invention, adjustment of the lower limb prostheses can be achieved by choosing a compressible member having desired deflection characteristic in response to the loading/unloading cycles. Aside from size or length restrictions, such a compressible member is chosen to be stiffer for a heavier person and softer for a lighter person. In accordance With one embodiment, a compressible member having a nonlinear spring characteristic is provided which increases in stiffness as compressed. Thus, during more vigorous activities, or if a larger impact loading is encountered such as when the amputee suddenly has the need to jump or run, the spring will not "bottom-out" or reach maximum deflection. During less vigorous activities, however, the spring will retain more compliant characteristics so as to provide cushioning on amputee's stump from the impact forces.

In one preferred embodiment, Belleville springs are arranged within the inner and outer pylons. The springs are stacked such that they alternately have their concave sides up, down, up, down, etc. in order to allow them to compress to store energy. Belleville springs have a well known nonlinear deflection response to loading. Thus, the arrangement results in a relatively compliant foot at low spring deflections and continued compression of the shock absorbing prosthesis at nearly the maximum deflection of the springs. During activities where a high impact load is applied to the prosthesis, such as when jumping, the springs and pylons do not "bottom out" or stop moving abruptly, but instead reach their point of maximum compression somewhat more gradually.

In another aspect of the present invention, a compression member comprising a compressible medium such as a gas is provided within a chamber of the outer pylon. The compressible medium preferably has a nonlinear displacement or deflection response to loads which provides compliance of the present prosthesis that is more comfortable for the amputee during normal and impact loading types of activities.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

FIG. 2 is an exploded view of the shock module of FIG. 1A, illustrating a preferred configuration for connecting the upper end of the coil spring.

FIG. 14 is a longitudinal sectional view of another alternative embodiment of a shock module having features and advantages in accordance with the teachings of the present invention.

FIG. 15 is a sectional view of the shock module of FIG. 14, taken along line 15—15.

FIG. 22 is a side view illustrating an alternative attachment of a shock module of the invention to a prosthetic foot.

FIG. 23 is a sectional view illustrating the attachment configuration of the shock module and prosthetic foot of FIG. 22, taken along line 22—22.

FIG. 32 is a perspective view of a tubular cuff used to connect the first pylon of FIG. 24 to the second pylon.

FIG. 33 is a top view of the tubular cuff of FIG. 32.

FIG. 34 is a cross-sectional view of the tubular cuff of FIG. 32.

FIG. 45 is a an exploded perspective view of the composite disk spring of FIG. 43.

DETAILED DESCRIPTION OF THE PREFERRED EMBODIMENTS

Figures 1A, 1B:
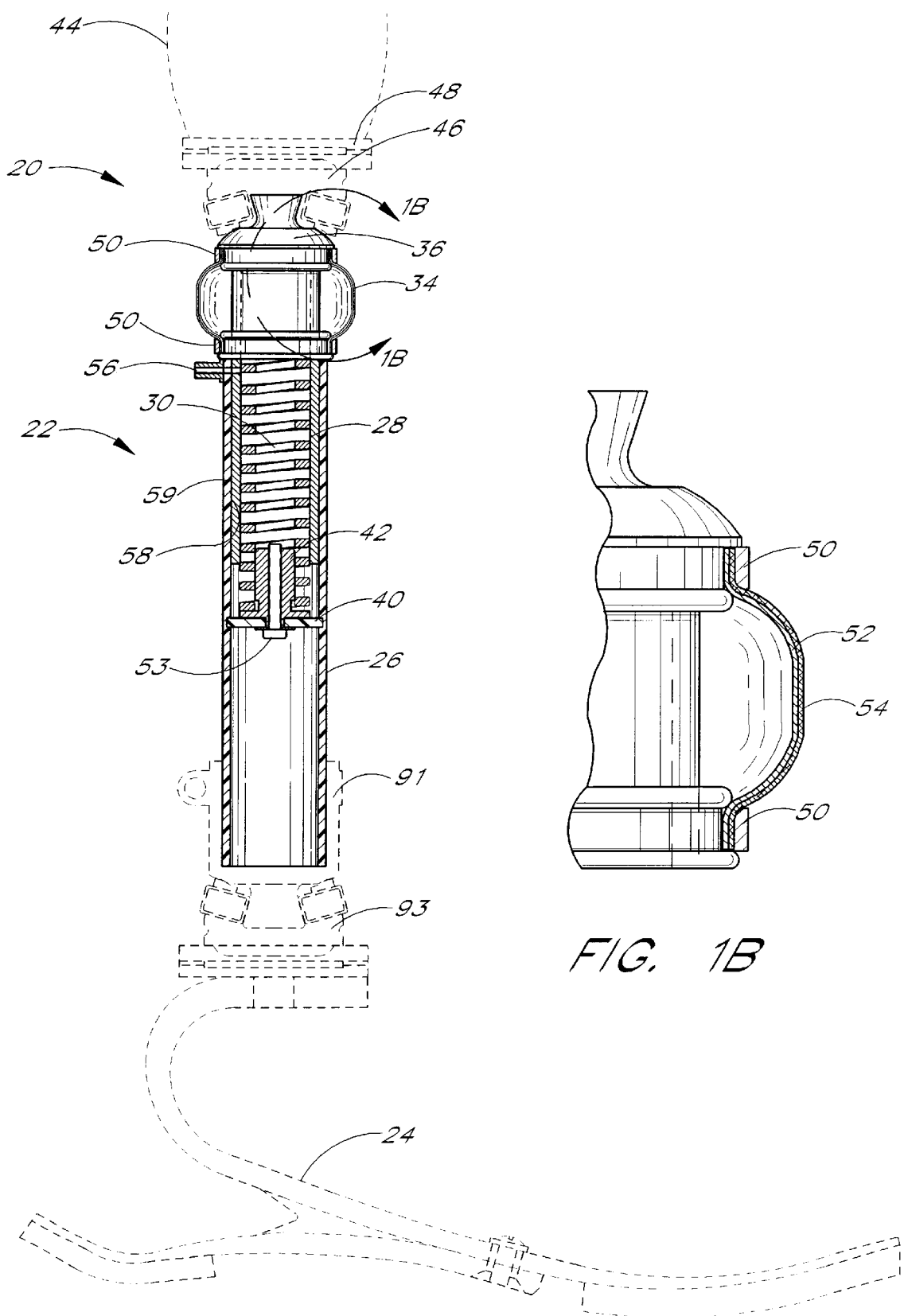
FIG. 1A is a longitudinal sectional view of a lower limb prosthesis illustrating one embodiment of a shock module having features and advantages in accordance with the teachings of the present invention.
FIG. 1B is a partial sectional view of the shock module of FIG. 1A, illustrating a preferred configuration of the torque-resisting cuff of the present invention.

FIG. 1A shows a preferred embodiment of a lower limb prosthesis 20 including a shock module 22 constructed and assembled in accordance with the teachings of the present invention. For purposes of illustration, the prosthesis 20 is shown as also including a prosthetic foot 24, in this case a Flex-Walk® foot available from Flex-Foot, Inc. of Aliso Viejo, Calif., and a stump socket 44. In particular, the upper end of shock module 22 is connected to stump socket 44, illustrated by way of example by utilizing a female pyramid fitting 46 and an alignment cup 48.

Shock module 22 includes telescoping hollow cylindrical pylons 26 and 28, shaped and adapted for smooth relative motion. Pylons 26 and 28 are preferably slidingly and rotationally interengaged with each other while retaining their operative horizontal alignment with each other through a relatively close fit between the inside dimensions of outer pylon 26 and the outside dimensions of inner pylon 28. Inner pylon 28 is adapted to be attached to a stump socket 44, as described later herein. Outer pylon 26 preferably has a cylindrical outer surface to facilitate the attachment of various types of prosthetic feet using conventional prosthetic couplers. For example, the lower end of pylon 26 may be attached to a prosthetic foot having a horizontal attachment section, such as the prosthetic foot 24 in FIG. 1, or to a prosthetic foot having a vertical attachment section. Both types of attachments are well known in the prosthetic foot art.

Shock module 22 includes a resilient element, such as a coil compression spring 30 or a compressible fluid, for providing impact absorption during use of the prosthesis 20. Shock module 22 preferably includes a hybrid spring-fluid resilient element, comprising an internal coil compression spring 30 in combination with a compressible fluid such as air. Spring 30 is preferably proximally fixed with respect to inner pylon 28 and distally fixed with respect to outer pylon 26. A valve 56 is provided within pylon 26 to vary the pressure of the fluid inside of shock module 22. Valve 56 is in fluid communication with the interior space defined by pylon 26, including the narrow annular space between pylons 26 and 28 and the interior space defined by inner pylon 28. A torque-resisting cuff 34 provides torsion-resistance to the prosthesis and also keeps dirt and other debris from getting between pylons 26 and 28 and affecting their relative motion. The cuff 34 may be configured to provide some additional impact resistance. The cuff 34 is proximally attached to inner pylon 28 and distally attached to outer pylon 26. Preferably, both of these attachments are near the proximal ends of said pylons and are made via ring clamps 50 which provide air-tight seals.

FIGS. 1A and 2 illustrate one example of an attachment construction for attaching the proximal end of the shock module 22 to a stump-supporting socket. A variety of other suitable attachment constructions could also be used without departing from the teachings of this invention. According to the preferred attachment construction, a male pyramid fitting 36 is fixed to the proximal end of inner pylon 28 and is adapted to be coupled to female pyramid fitting 46. This assembly allows the shock module 22 to be proximally attached to a broad selection of prosthetic sockets (for example, in FIG. 1A, to a stump socket 44 via an alignment cup 48) or other intermediate prosthetic devises, such as a prosthetic knee. Fitting 36 is preferably fixed with respect to pylon 28 by a threaded engagement between the exterior surface of fitting 36 and the interior surface of pylon 28. Alternatively, fitting 36 may be adhesively bonded to pylon 28 using, for example, 3M #420/460 toughened epoxy. If desired, fitting 36 may have a bonding hole 37 and/or bonding grooves 39, as can be seen in FIG. 2, so as to facilitate better bonding, Those skilled in the art will appreciate that fitting 36 preferably provides an air-tight seal with respect to the interior space defined by pylon 28. An air-tight seal may be achieved by inserting a rubber O-ring seal between the surfaces of fitting 36 and pylon 28, or alternatively by forming a ring-shaped adhesion bond around the circumference of fitting 36 to bond fitting 36 to the interior surface of pylon 28. Fitting 36 is preferably formed from titanium, but may be formed other suitable materials keeping in mind the goals of strength, light-weight, and maintaining a strong bond/attachment to the inner pylon 28.

FIG. 2 illustrates a preferred attachment configuration for the top end of coil spring 30. Spring 30 is attached to a top spring end fitting 38 secured to the bottom of pyramid fitting 36, so that the top end of spring 30 is fixed in position relative to inner pylon 28. The fitting 38 is preferably fabricated from a low-carbon steel and is secured to fitting 36 via a longitudinal hex cap screw 41 that is provided within a through hole inside of fitting 36 and is threadingly engaged with fitting 38. Fitting 36 has an upper recess 55 that seats the cap of hex cap screw 41 and a lower recess 57 that snugly houses a top protrusion 45 of the fitting 38. Optionally, a rubber washer 43 may be provided against the cap of screw 41 to achieve an air-tight seal. Alternatively, spring end fitting 38 could be formed integrally with fitting 36. In either case, the top surface and top coil of spring 30 are preferably adhesively bonded (using, for example, a 3M #420/460 toughened epoxy) to the horizontal annular surface 47 and the vertical cylindrical surface 49, respectively, of the top spring end fitting 38. Further, the protrusion 51 has a diameter nominally smaller than the inner diameter of the spring 30 but slightly larger than the diameter of cylindrical surface 49, which provides clearance for the aforementioned adhesive bonding of the top spring coil.

Below inner pylon 28, a transverse rigid disk-shaped support base 40 is fixed with respect to outer pylon 26 to provide support for the bottom of spring 30. Alternatively, the lower end of pylon 26 could have a completely solid configuration to provide a base for supporting the spring 30, without departing from the teachings of the invention, Base 40 preferably provides an air-tight seal with respect to the interior space defined by outer pylon 26.

Figure 3:
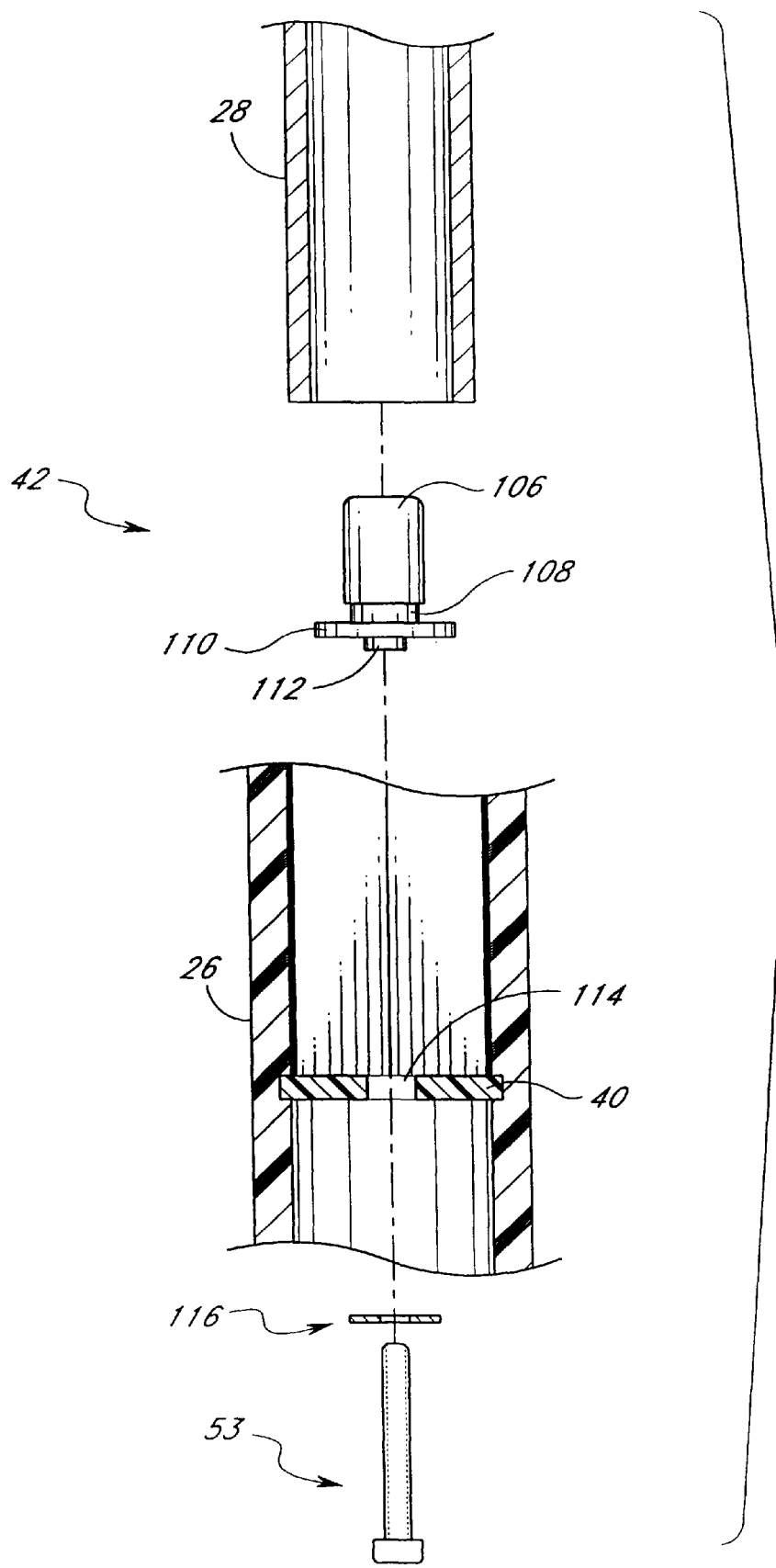
FIG. 3 is an exploded view of the shock module of FIG. 1A, illustrating a preferred configuration for connecting the lower end of the coil spring.

Referring to FIG. 3, a bottom spring end fitting 42 is preferably formed from a low carbon steel and preferably configured similarly to top spring end fitting 38. Fitting 42 may be secured to base 40 via a threaded engagement with a longitudinal hex cap screw 53 provided within a through hole 114 in base 40. Alternatively, fitting 42 could be formed integrally with base 40. Fitting 42 has a bottom protrusion 112 that fits snugly into through hole 114. Optionally, a rubber washer 116 may be provided against the cap of screw 53 to ensure an air-tight seal. A disk-shaped element 110 of the fitting 42 rests on the upper surface of the base 40.

The bottom of coil spring 30 is attached to bottom spring end fitting 42 in the same manner as described above, so that the bottom end of spring 30 is fixed in position relative to outer pylon 26. In particular, the bottom surface and bottom coil of spring 30 are preferably adhesively bonded to the top annular surface of element 110 and the vertical surface of cylindrical element 108, respectively, of the fitting 42. The stem 106 has a diameter nominally smaller than the internal diameter of spring 30 and partially extends into spring 30, thereby providing support to prevent buckling of the spring. The element 108 has a diameter slightly less than that of the stem 106 to permit clearance for the aforementioned adhesive bonding of the bottom spring coil.

Those skilled in the art will understand that spring end fittings 38 and 42 are exemplary and not limiting, and that any of a variety of suitable spring attachment constructions could be used to achieve the purposes of this invention, giving due consideration to the goals of strength and durability of the attachment.

The pylons 26 and 28, including the support base 40, are preferably fabricated from a strong light-weight material, such as, for example, a carbon graphite and epoxy composite. Preferably, the inner surface 58 of outer pylon 26 and/or the outer surface 59 of inner pylon 27 are lined with a polymeric material, such as RULON 142 bearing tape, to minimize frictional forces between said pylons during relative motion therebetween. Alternatively, one or both of the pylons may be fabricated from a light-weight metal, such as age-hardened aluminum, and coated with a low friction material such as a TUFRAM synergistic coating (aluminum oxide anodize with infusion of a low friction polymer and a dry film lubricant). Optionally, a lubricant, such as a Krytox GPL 205 grease manufactured by Miller-Stephenson Chemical, may be smeared on the outside surface of inner pylon 28 for improved smoothness of motion. Also, if necessary, the amputee or prosthetist may adjust the length of the shock module 22 simply by cutting the outer pylon 26 to the desired length, thereby allowing the shock module 22 to be custom-fitted as dictated by the height and/or leg length of the amputee.

Figure 4:
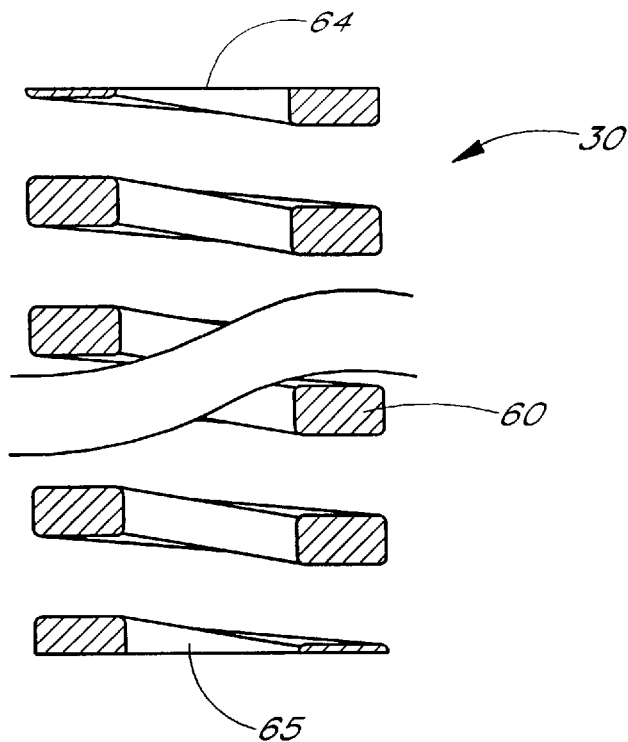
FIG. 4 is a sectional view illustrating a preferred embodiment of the coil spring.
Figure 5:
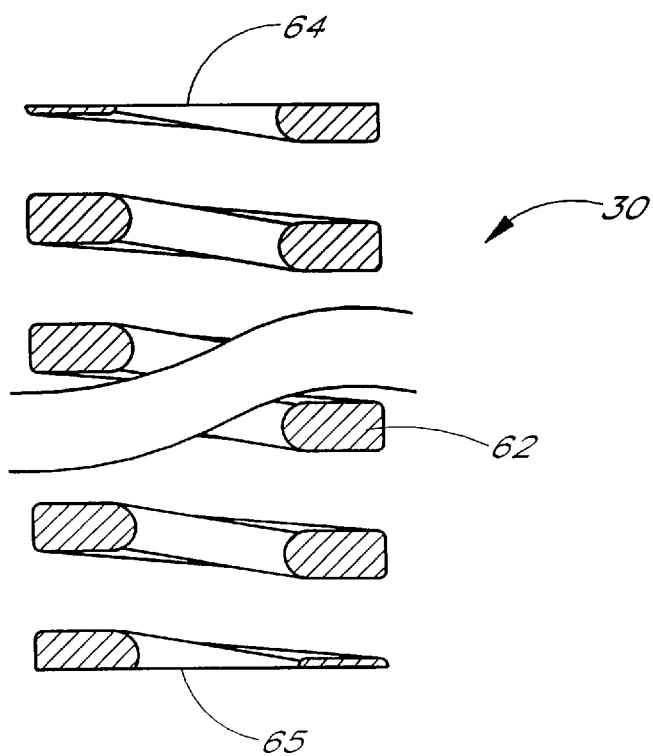
FIG. 5 is a sectional view illustrating another preferred embodiment of the coil spring.

In the preferred embodiment of the invention, the spring 30 is a die spring constructed from chrome-vanadium steel wire. Preferably, the coiled spring wire has either a rectangular-with-rounded-corners cross-section 60 or a D-shaped cross-section 62, shown in FIGS. 3 and 4, respectively. Such cross-sections not only provide for a more compact spring, but, also significantly lower the maximum stress level of the wire and contribute to a considerably longer spring life. Preferably, the top end 64 and the bottom end 65 of the spring 30 are closed and ground square to provide a maximum bearing surface and, hence, a substantially uniform stress distribution. Other preferred manufacturing methods that enhance spring life include heat tempering, shot peening to reduce working stresses and enhance fatigue resistance, and electrostatic coating for a durable, anti-corrosive finish.

Those skilled in the art will realize that a wide variety of other spring types may also be utilized with efficacy without departing from the spirit and scope of the invention. For example, the spring 30 can be constructed from a different chrome-alloy steel wire, such as a chrome-silicon steel wire, or from an oil-tempered high-carbon steel wire. Moreover, the wire cross-section of the spring 30 can assume a variety of shapes, such as circular, ellipsoidal, or trapezoidal, as desired, giving due consideration to the goals of durability, uniform stress distribution, and high fatigue strength. The table below provides examples of die springs that may be employed in the present invention. The nominal inner and outer diameters of all six springs depicted in the table are 0.375 inches and 0.75 inches, respectively.

| Spring Rate (lbs/inch) | Spring Length (inches) | Maximum Deflection (inches) | Wire Size (inches × inches) | Weight (grams) | Brand |
|---|---|---|---|---|---|
| 264 | 2 | 0.80 | 0.156 × 0.093 | 35 | Century |
| 312 | 3 | 0.90 | 0.165 × 0.125 | 64 | Century |
| 362 | 3 | 0.90 | — | 68 | Danly |
| 405 | 3 | 0.75 | 0.165 × 0.135 | — | Century |
| 483 | 3 | 0.75 | — | 67 | Dayton |
| 512 | 3 | 0.75 | — | 68 | Danly |

Advantageously, the coil spring 30 is preferably free of pre-loading stress. In other words, the spring 30 is not compressed when the shock module 22 is in its unloaded state. This ensures a smooth or non-jarring compression initiation of the spring 30 when the amputee applies weight on the prosthesis 20. Upon load release the spring 30 is free to extend smoothly and there is no jarring hard stop at full extension. Thus, the absorption and release of impact energy is achieved in a more comfortable manner for the amputee. Moreover, the spring 30 is chosen such that it exhibits a substantially linear response to loading and unloading. In other words, the axial spring displacement is substantially linearly proportional to the applied force. Field testing has shown that utilization of such a linear spring 30 in the shock module 22 best simulates a natural gait for the wearer. Also, the spring 30 is selected such that its stiffness (or spring rate) is best suited to the weight of the particular amputee. The spring utilized in the shock module 22 is preferably such that during ambulation, for a given amputee's weight, the maximum relative axial displacement between the pylons 26 and 28 is about one inch, thereby providing an inherently comfortable feel for the wearer.

Figure 6:
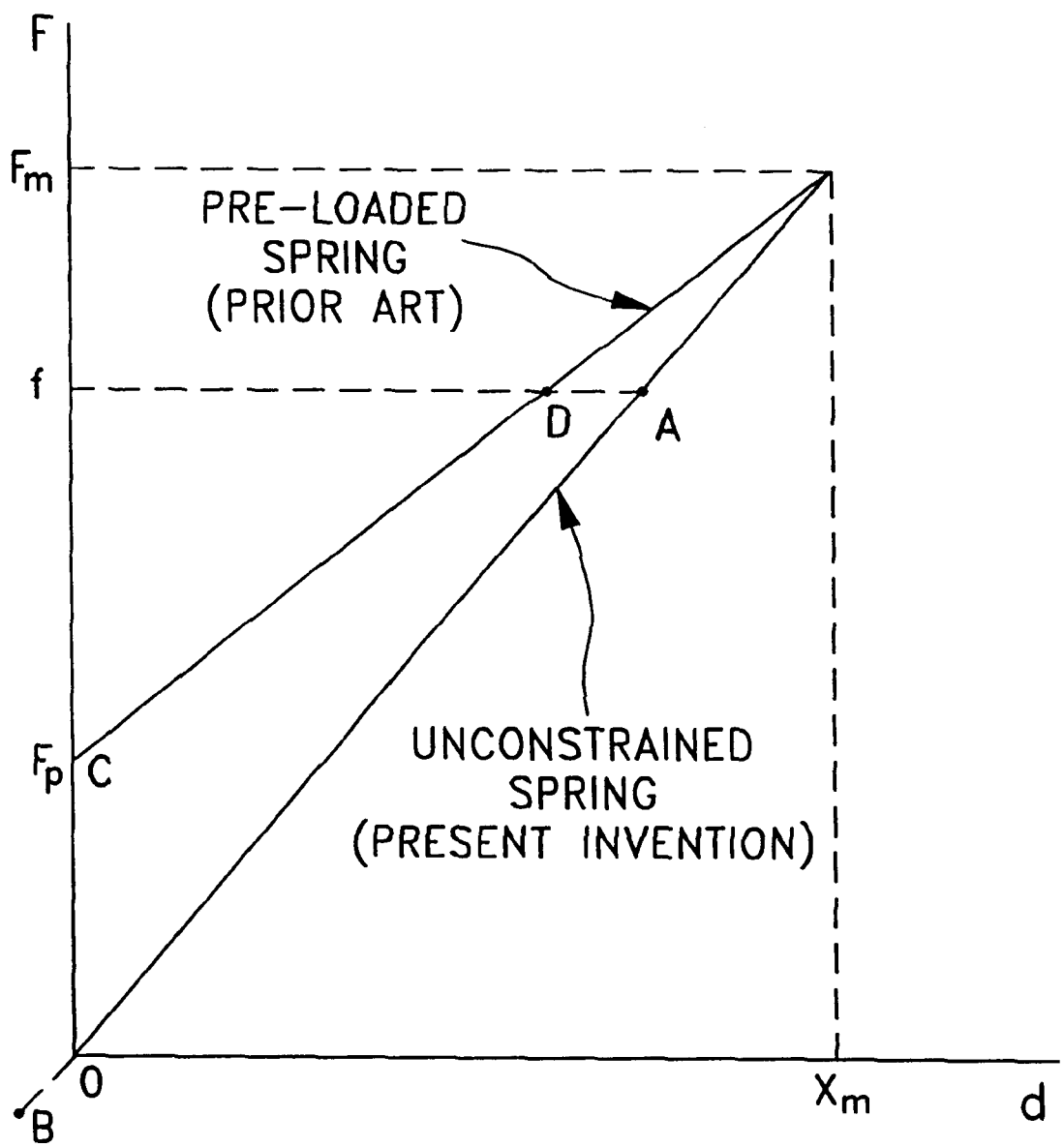
FIG. 6 is a graphical comparison between the impact absorbing characteristics of a preferred embodiment of the coil spring and the prior art.

An examination of FIG. 6 best illustrates the advantageous features of using an "unconstrained" (not pre-loaded) coil compression spring as compared to utilizing a "pre-loaded" spring (employed, for example, by Martel et al, U.S. Pat. No. 4,883,493) in an impact absorbing prosthesis. In FIG. 6, the horizontal axis represents the compressive displacement, d, of the spring, and the vertical axis represents the force or load, F, applied to the spring. By way of example, it is assumed that the maximum compressive displacement, $x_m$, of both springs occurs at the same load, $F_m$, and that both springs are linear. Moreover, the pre-load on the pre-loaded spring is set to a value $F_p$. If an impact force, f, is transmitted to the prosthetic leg at the instant there is foot/ground contact, the unconstrained coil spring will instantaneously compress and non-jarringly absorb the impact energy by moving from point O to point A in FIG. 6. On the other hand, the pre-loaded spring will initially resist compression (due to the pre-load, $F_p$, represented by the line OC in FIG. 6) and deliver a jarring impact to the wearer before it commences compression.

Now, consider the converse scenario in which before the foot loses contact with the ground the load on the springs is f. As foot/ground contact is terminated, the unconstrained spring extends from point A to point O (and possibly overextends to point B, if so desired, before returning to point O) while smoothly releasing its stored energy. In contrast, the pre-loaded spring extends from point D to point C where it experiences a jarring hard stop, the jolting effect of which is transmitted to the amputee's stump. Thus, by the utilization of an unconstrained coil spring 30 in the shock module 22, the wearer's comfort level during mobile activities is dramatically enhanced.

As shown in FIG. 1B, cuff 34 preferably has a tubular dual-layered configuration. According to this configuration, inner layer 52 is preferably formed from a resilient material such as rubber. The thickness of the inner layer 52 affects the impact resistance and torsion-resistance of the shock module 22. A desired level of impact resistance is obtainable by providing a relatively thin inner layer 52. If the inner layer 52 is too thick, it will increase the impact resistance to an undesirable level. However, this thickness might not provide sufficient torsion-resistance. Thus, the outer layer 54 is provided to increase the torsion-resistance. The outer layer 54 preferably comprises a knitted fabric consisting of a combination various fibers, such as spectrafiber, kevlar, nylon, and polyester. The combination of fibers is advantageously selected to provide sufficient elasticity to accommodate the outward expansion of the inner resilient layer 52, and also to provide sufficient strength and resistance to torsion. For example, at an internal pressure of about 50 psi, it is desired that the torsion-resistance be high enough to permit a maximum of about 20 to 30 degrees of rotation. Different outer layers 54 may be offered providing different ranges of torsional stiffness.

The fiber pattern of the outer layer 54 of the cuff 34 affects both the impact resistance and torsion-resistance of the shock module 22. If the fibers are aligned substantially parallel to the longitudinal axes of the pylons 26 and 28, the cuff 34 provides relatively more impact resistance and relatively less torsion-resistance. Conversely, if the fibers are aligned substantially perpendicular to the longitudinal axes of the pylons, the cuff 34 provides relatively less impact resistance and relatively more torsion-resistance. Preferably, the fibers of the knitted fabric 54 are substantially oriented at an angle from the longitudinal axes of the pylons, to achieve a suitable balance between the degrees of impact resistance and torsion-resistance. Such angle is preferably within the range of 30 to 60 degrees, more preferably within the range of 40 to 50 degrees, and most preferably about 45 degrees. Moreover, the fibers are preferably arranged in a crisscross pattern.

The cuff 34 hinders undesired contaminatory materials (such as dust) from entering the body of the shock module 22 and damaging the sliding surfaces 58 and 59 of pylons 26 and 28. It also minimizes wastage of any lubricating grease which may be smeared onto such surfaces.

Shock module 22 provides smooth impact absorption. During the gait cycle of normal ambulation there is axial motion between pylons 26 and 28. Upon heel strike, the inner pylon 28 begins to slide down to cause the aforementioned resilient means to compress and store energy. Maximum compression and storage of energy occurs as the amputee's weight shifts from the heel region of the prosthetic foot towards the toe region. Then, as the amputee's weight shifts closer to the toe region, the compression means begins to expand and release stored energy, providing beneficial lift and thrust forces to the amputee. A prosthetist, or the amputee, can adjust the degree of impact absorption by selectively replacing the spring 30 to suit the particular attributes and activity of the amputee. Furthermore, the amputee can easily and conveniently fine-tune the degree of impact absorption simply by varying the fluid pressure inside of shock module 22.

Shock module 22 also provides smooth rotational compliance of the prosthesis. Cuff 34 is designed to resist the relative rotation of pylons 26 and 28, and at the same time provide some rotational compliance therebetween. As pylons 26 and 28 rotate relative to each other, the top and bottom ends of cuff 34 are likewise twisted with respect to one another. However, the cuff 34 is resistant to such twisting and provides a torsional force opposite to the direction of rotation/twisting. Moreover, as a particular twisting motion is enhanced, the oppositely directed torsional force increases. Thus, the cuff 34 operates like a torsion spring, in that it resists any incremental rotation of the pylons 26 and 28, relative to each other. Furthermore, the amputee can easily and conveniently adjust the degree of torsion-resistance of the cuff 34 by varying the fluid pressure inside of the shock module 22. As the fluid pressure increases, the cuff 34 expands, causing increased tension in layers 52 and 54 of the cuff 34. As a result, the cuff 34 provides greater resistance to twisting and, consequently, increased torsion-resistance.

Figure 7:
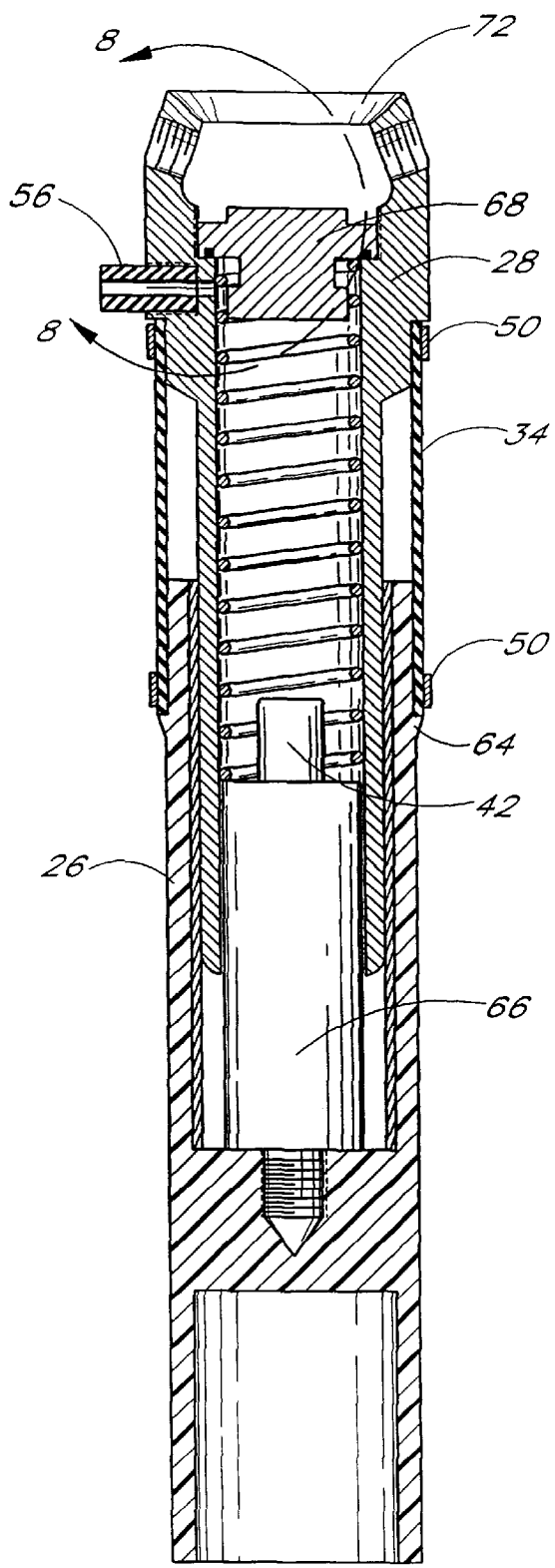
FIG. 7 is a longitudinal sectional view of an alternative embodiment of a shock module having features and advantages in accordance with the teachings of the present invention.
Figure 8:
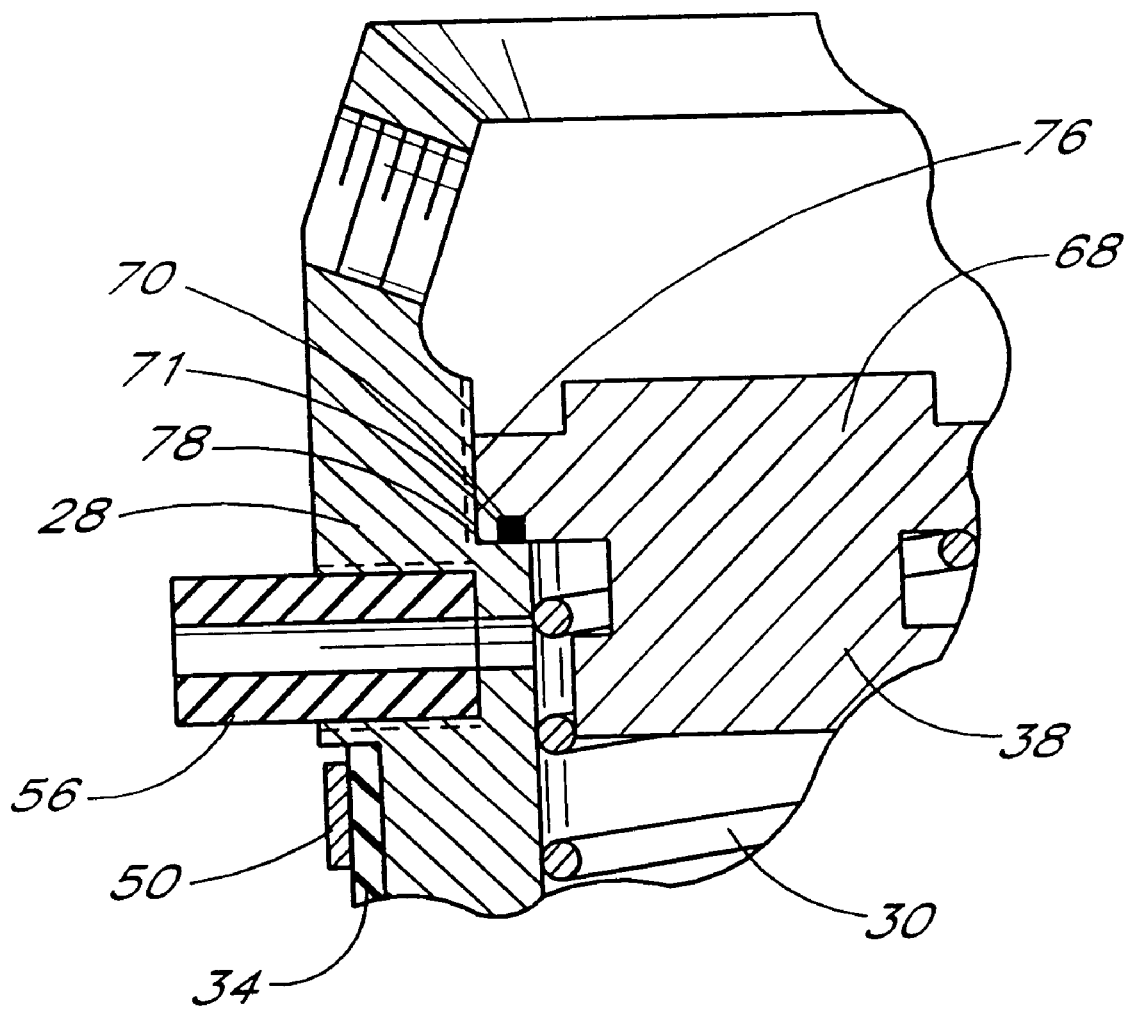
FIG. 8 is an exploded sectional view of the shock module of FIG. 7, illustrating a preferred configuration of the end cap and O-ring assembly.

FIGS. 7 and 8 illustrate an alternative embodiment of the invention. According to this embodiment, outer pylon 26 is configured with a circular ridge 63 on its exterior to help maintain the distal position of the cuff 34 relative to the pylon 26. Pylon 26 optionally has a solid cylindrically-shaped bottom support 66, screwed into the base 40. A bottom spring end fitting 42 is attached to the top of support 66, to which the bottom end of spring 30 is attached. The diameter of bottom support 66 is smaller than the inside diameter of outer pylon 26, forming an annulus within which inner pylon 26 axially moves. The slide surfaces of pylons 26 and 28 and support 66 are preferably lined with RULON tape or TUFRAM coating, as described above, to minimize frictional forces therebetween. Also, the length of bottom support 66 may be customized to suit the amputee. Typically, a prosthetist will select a spring 30 to suit the particular gait, weight, and leg length of the amputee. Then the prosthetist will cut the support 66 to the length that accommodates the selected spring 30. Alternatively, the spring 30 could extend down to the base 40, thus eliminating the need for the support 66.

The torque-resisting cuff 34 may optionally be configured to oscillate between a substantially straight vertical position, as in the embodiment shown in FIG. 7, and a curved position. This may reduce the effective horizontal cross-section of the cuff 34 at maximum compression. However, the outwardly curved position shown in FIG. 1A is preferred, because it prevents inward buckling of the cuff 34 during compression of the shock module 22. Another feature of this embodiment is that the valve 56 is provided in the inner pylon 28, above the cuff 34. Recall that in the embodiment of FIG. 1A the valve 56 is provided in the outer pylon 26, forcing the fluid to travel through the annulus between the pylons 26 and 28. In contrast, the configuration of the shock module of FIG. 7 allows the fluid to travel directly to and from the region surrounding the spring 30. This improves the efficiency of the relative motion between the pylons, because less fluid passes through the annulus therebetween.

As shown in FIG. 7, the inner pylon 28 has an enlarged outside diameter at its proximal end, approximately equal to the outside diameter of the outer pylon 26. This configuration allows the cuff 34 to have a straight vertical position when the shock module 22 is uncompressed. Pylon 28 also has a female pyramid fitting 72 at its proximal end, for attachment to a stump socket (not shown). Further, as shown in FIG. 8, pylon 28 has a circular ridge at its proximal orifice, consisting of vertical surface 76 and horizontal surface 78. Surface 76 is threaded to receive an externally threaded end cap 68. The end cap 68 has a notch 70 in its bottom surface, within which a rubber O-ring seal 71 is positioned. When the end cap is tightly screwed into pylon 28, the O-ring seal 71 is compressed to provide an air-tight seal with respect to the interior of pylon 28. A top spring end fitting 38 is attached to the bottom of end cap 68, to which the top of spring 30 is attached as described above. Fitting 38 may be formed integrally with end cap 68 or may be secured thereto by any well-known means, such as via a hex cap-screw as described above.

Those skilled in the art will understand that both of the embodiments described above could be inverted so that the outer pylon 26 is adapted to be attached to a stump socket and the inner pylon 28 is adapted to be attached to a prosthetic foot, without departing from the spirit and scope of the invention.

FIGS. 9–13 illustrate an alternative embodiment of the present invention. In this embodiment, best illustrated by FIGS. 9A and 9B, a shock module 22 comprises two non-telescoping pylons 80 and 82. A hybrid spring-fluid compression means, comprising a coil compression spring 30 in combination with a compressible fluid such as air, provides impact absorption. A torque-resisting cuff 34 provides torsion-resistance. The spring 30 and cuff 34 are proximally attached to the distal end of upper pylon 80 and distally attached to the proximal end of lower pylon 82. A guide pin 83 is attached to lower pylon 82 to maintain the longitudinal axes of pylons 80 and 82 in a colinear alignment. Upper pylon 80 is adapted to be attached to a stump socket by any of a variety of methods well known in the art. Also, any standard-type prosthetic foot may be attached to lower pylon 82 by utilizing conventional couplers, as described above. Further, pylon 82 can be cut by a prosthetist or amputee to a desired length, to suit the particular requirements of the amputee.

Figure 10:
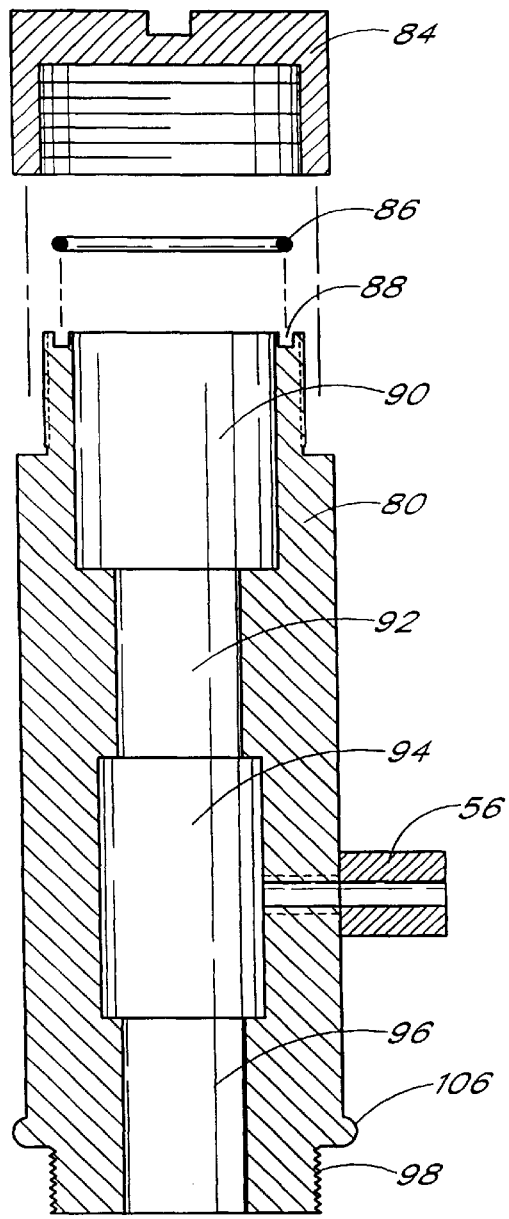
FIG. 10 is a sectional view of the upper pylon and end cap of the shock module of FIG. 9A.
Figure 11:
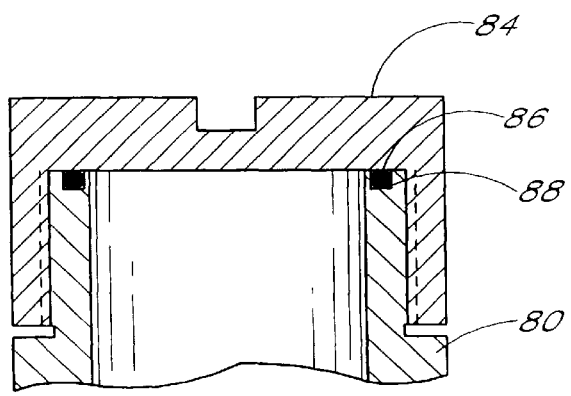
FIG. 11 is an exploded partial sectional view of the end cap and O-ring assembly of the shock module of FIG. 9A.

FIGS. 10 and 11 illustrate in greater detail the preferred structure of upper pylon 80. Pylon 80 is shown having a generally cylindrical exterior. The proximal end of pylon 80 is shown having a smaller outside diameter than the body of pylon 80. Those skilled in the art will understand that pylons 80 and 82 may be configured to have any suitable exterior shape, giving due consideration to the goal of supporting an amputee. The proximal end of pylon 80 is externally threaded to receive an internally threaded end cap 84. An air-tight seal is achieved by enclosing a rubber O-ring seal 86 in a notch 88 that is provided on the upper surface of pylon 80. The end cap 84 is adapted to be attached to the distal end of a stump socket. Further, pylon 80 comprises integrally formed tubular sections 90, 92, 94, and 96. Section 90 has the largest inside diameter of the four sections, while the inside diameters of sections 92 and 96 are both approximately equal to the diameter of guide pin 83. The inside diameter of section 94 is larger than that of sections 92 and 96, but smaller than that of section 90. A valve 56 is attached to section 94 as shown. Valve 56 is in fluid communication with the interior space defined by pylon 80, as well as the interior space defined by cuff 34, described in more detail herein.

Figure 12:
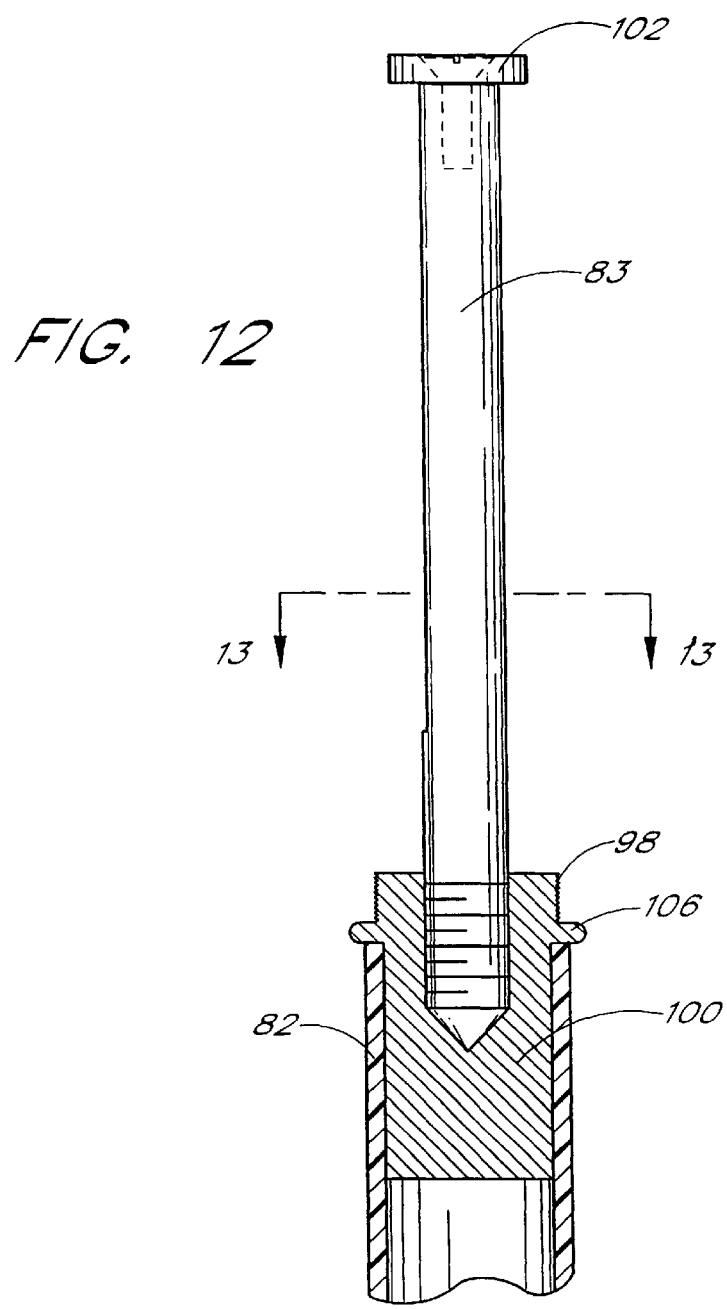
FIG. 12 is a sectional view of the lower pylon, end fitting, and guide pin assembly of the shock module of FIG. 9A.
Figure 13:
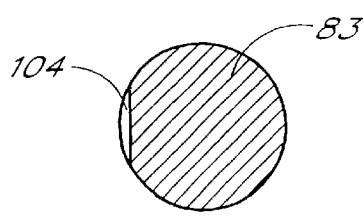
FIG. 13 is a sectional view of the guide pin of FIG. 12, taken along line 13—13.
Figure 16:
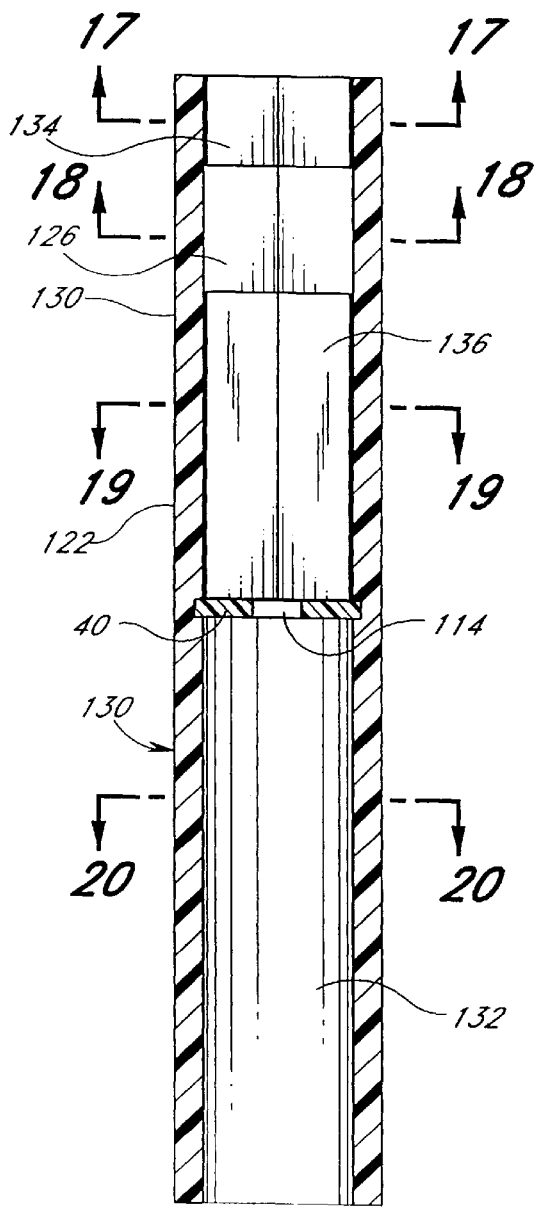
FIG. 16 is a longitudinal sectional view illustrating a preferred embodiment of the outer tube.
Figure 17:
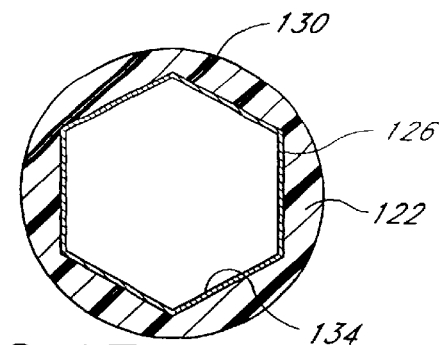
FIG. 17 is a sectional view of the outer tube of FIG. 16, taken along line 17—17.
Figure 18:
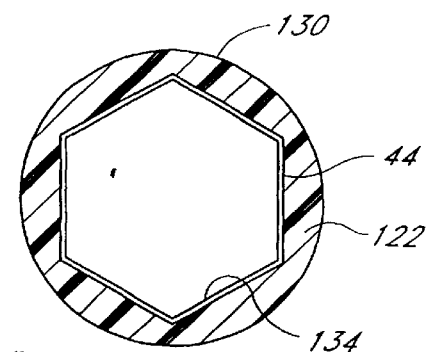
FIG. 18 is a sectional view of the outer tube of FIG. 16, taken along line 18—18.
Figure 19:
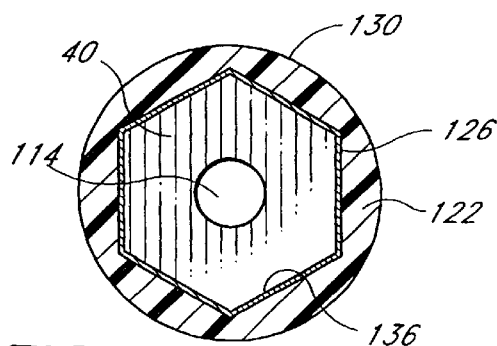
FIG. 19 is a sectional view of the outer tube of FIG. 16, taken along line 19—19.
Figure 20:
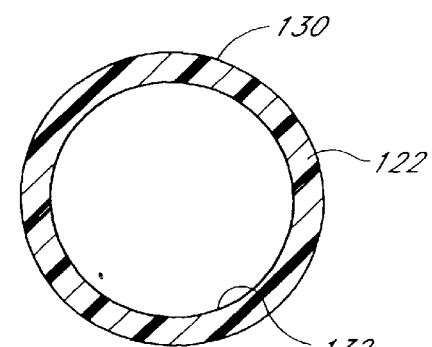
FIG. 20 is a sectional view of the outer tube of FIG. 16, taken along line 20—20.

FIG. 12 illustrates a preferred attachment means for the guide pin 83. Lower pylon 82 includes a fixed solid fitting 100 at its proximal end. Fitting 100 may be fixed within pylon 82 by a variety of means, including adhesion bonding or threaded engagement, or could alternatively be formed integrally with the pylon 82. The distal end of guide pin 83 is attached to fitting 100. In particular, the guide pin 83 is threadingly engaged with, or screwed into, the fitting 100, in a manner such that the guide pin 83 is positionally fixed with respect to pylon 82 and, further, such that the longitudinal axes of guide pin 83 and pylon 82 are maintained in a colinear alignment. Guide pin 83 may be formed from any of a variety of materials, giving due consideration to the goals of strength and light-weight. Suitable materials include titanium, carbon fibers, aluminum, and steel.

The overall construction of shock module 22 allows relative longitudinal and rotational motion between pylons 80 and 82, while maintaining their colinear alignment. The upper portion of the guide pin 83 is telescopically engaged with upper pylon 80. In particular, this engagement allows relative longitudinal and rotational motion between guide pin 83 and pylon 80. Since the diameter of guide pin 83 is approximately equal to the inside diameter of sections 92 and 96 of pylon 80, a relatively close fit is achieved between guide pin 83 and pylon 80. As a result, pylons 80 and 82 are maintained in a colinear alignment. Also, the inside surfaces of sections 92 and 96 and the surface of guide pin 83 may be lined with RULON tape or coated with TUFRAM, as described above, to minimize frictional forces therebetween.

Figure 9A:
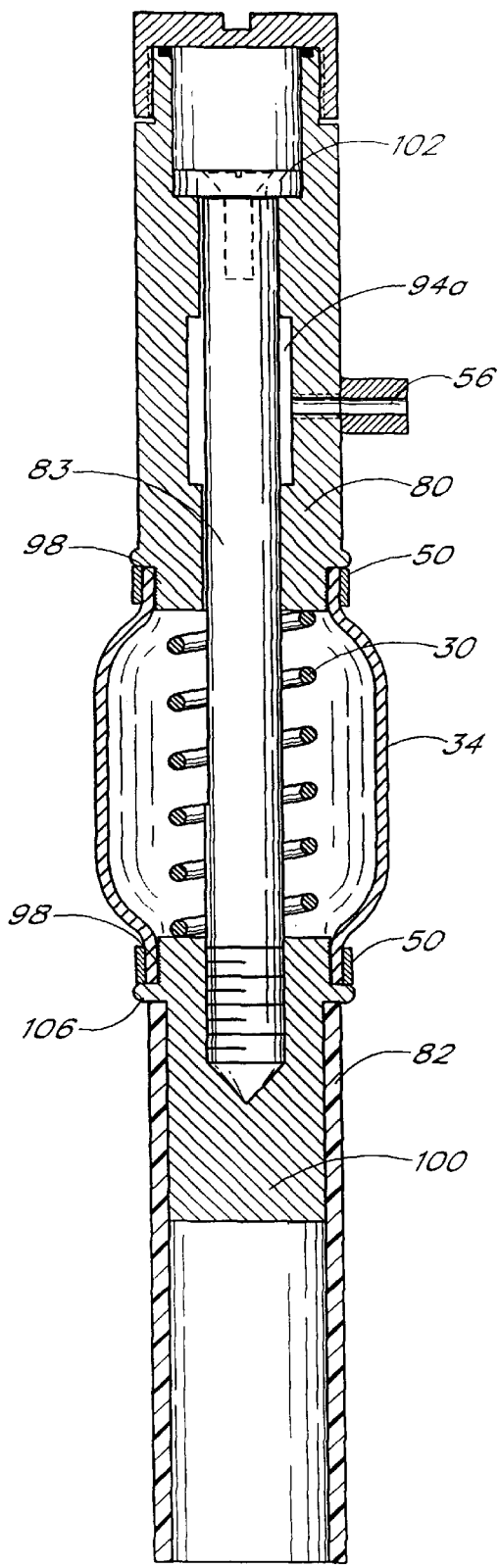
FIG. 9A is a longitudinal sectional view of another alternative embodiment of a shock module having features and advantages in accordance with the teachings of the present invention, shown in an uncompressed position.
Figure 9B:
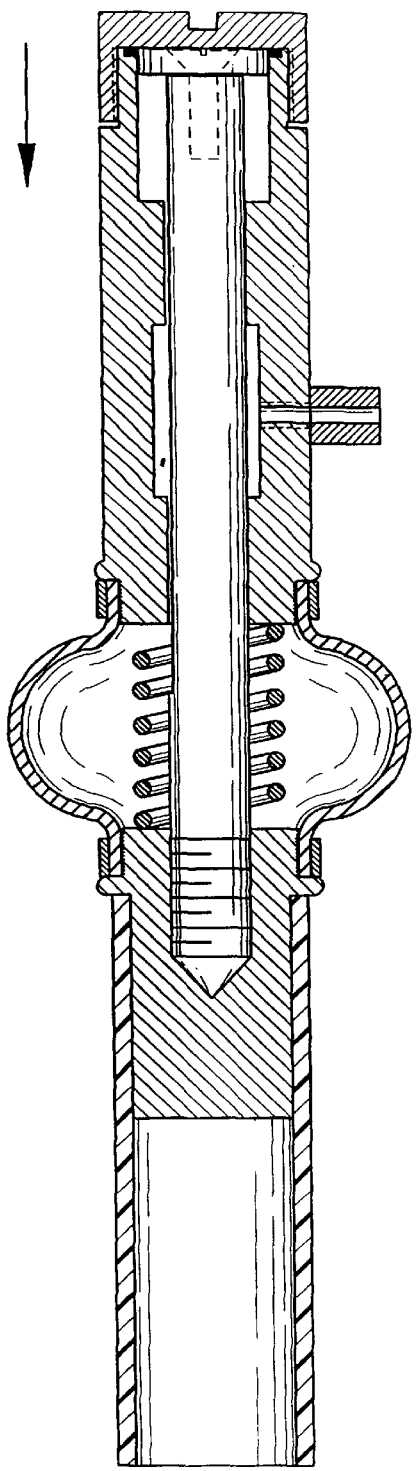
FIG. 9B is a sectional view of the shock module of FIG. 9A, shown in a compressed position.

As shown in FIGS. 9A, 9B, and 12, a disk-shaped guide pin head 102 is optionally attached to the proximal end of guide pin 83. The diameter of guide pin head 102 is larger than the inside diameter of section 92 of pylon 80. Thus, the guide pin head 102 can only travel within section 90 of pylon 80, and the vertical length of section 90 determines the maximum vertical/longitudinal deflection of the shock module 22. Shock module 22 is shown in FIG. 9A in an uncompressed state and in FIG. 9B in a compressed state.

As shown in FIGS. 9A and 9B, a spring 30 is positioned so that its coils spiral around a portion of guide pin 83. The spring 30 is proximally attached to the distal end of upper pylon 80, and distally attached to the proximal end of lower pylon 82, by a screw clamp, welding, or any suitable means known in the art, giving due consideration to the goals of strength and durability of the attachment. Similarly, the torque resisting cuff 34 is proximally attached to the distal end of upper pylon 80, and distally attached to the proximal end of lower pylon 82, via ring clamps 50. Grooves 98 and lips 106 are preferably provided on both the distal end of pylon 80 and the proximal end of pylon 82. The grooves 98 provide a more effective air-tight connection of the cuff 34 to the pylons 80 and 82. The lips 106 are provided to maintain the vertical position of the ends of cuff 34 relative to the pylons, especially during compression of the shock module 22.

During use of the prosthesis, the amputee can utilize the valve 56 and/or a fluid pump (not shown) to vary the pressure of the fluid inside of shock module 22. The fluid pump may either be extrinsic or intrinsic to the shock module 22. As mentioned above, the diameter of guide pin 83 is approximately equal to the inside diameter of sections 92 and 96 inside of upper pylon 80. Thus, the guide pin 83 completely occupies the spaces inside of those sections. However, since section 94 has an inside diameter larger than the diameter of guide pin 83, an annular space 94a, within section 94 and encircling guide pin 83, remains unoccupied as shown in FIG. 9A. The valve 56 fluidly communicates with annular space 94a when the guide pin 83 is engaged within pylon 80. Furthermore, as seen clearly in FIG. 13, the guide pin 83 has a longitudinal notch 104 along its length. During use of the prosthesis, the amputee can utilize the valve 56 to pump fluid into the annular space 94a, which then flows down through the notch 104 to the region surrounding spring 30. Just as in the previously described embodiments, the pressurized fluid provides additional impact absorption to the prosthesis 20, as well as increased torsion-resistance associated with the expansion of the torque-resisting cuff 34, as described above.

All of the shock modules described above are highly useful for virtually all applications. As such, these embodiments are envisioned as being the embodiments of choice for most amputees. However, some amputees may prefer shock modules which do not provide rotational compliance, especially for applications in which the rotation of the lower leg and foot relative to the stump of the amputee is not absolutely essential, such as, for example, long distance running. Thus, the present invention provides a shock module in which rotational compliance is prevented, while maintaining the above-described benefits of selectively adjustable impact absorption and a means for preventing debris from entering and upsetting the smoothness of the relative motion between telescoping members, in a relatively simple but highly effective modular construction. Such a shock module is illustrated by FIGS. 14–21.

FIG. 14 shows a shock module 120 connected to a prosthetic foot 24. Shock module 120 includes an outer tube 122 and an inner shaft 124. The outer tube 122 and the inner shaft 124 are preferably slidingly and reciprocably interengaged with each other in the manner of a sleeve member and an arm member, while retaining their operative horizontal and rotational alignment with each other through a relatively close interlocking fit between the inside dimensions of the outer tube 122 and the inner shaft 124. FIG. 15 shows that the mating inner surface 126 of the outer tube 122 and the mating outer surface 128 of the inner shaft 124 are preferably hexagonal in shape to prevent or limit any relative rotation between the outer tube 122 and the inner shaft 124, Those skilled in the art will understand that any polygonal shape may be utilized for the telescoping surfaces without departing from the scope of the invention, giving due consideration to the goal of preventing or substantially limiting rotational compliance of the shock module.

A resilient means, such as a coil compression spring 30 and/or a compressible fluid such as air, is included to provide impact absorption. The spring type and the spring attachments to the outer tube 122 and inner shaft 124 are preferably the same as described above. Also, the spring 30 is preferably unconstrained, i.e., not pre-loaded. A valve may be provided to vary the fluid pressure. Further, a fluid pump, intrinsic or extrinsic to the shock module 120, may be provided in combination with the valve.

FIGS. 16–20 illustrate in more detail the preferred structure of the outer tube 122. A support base 40 with a central through hole 114 is disposed within the outer tube 122, as can best be seen in FIGS. 16 and 19. The support base 40 provides support and attachment means for the bottom end of the spring 30 as described above. The outer surface 130 preferably has a circular cross-section and facilitates the attachment of a prosthetic foot using conventional prosthetic couplers. The outer tube 122, including the support base 40, is fabricated from a strong light-weight material. A preferred material is a carbon graphite and epoxy composite. The length of the outer tube 122 is adjustable by the user simply by cutting the outer tube 122 to the desired length. Hence, the shock module 120 may be custom-fitted as dictated by the height and/or leg length of the wearer. Another convenience of the invention described herein is that the outer tube 122 is easily and inexpensively replaceable.

The inner surface of the outer tube 122 (FIGS. 16–20) consists of an upper inner surface 126 that has a hexagonal cross-section and a lower inner surface 132 that has a circular cross-section, the support base 40 serving as the divider between the upper inner surface 126 and the lower inner surface 132. Preferably, at least part of the upper inner surface 126 is lined with slide surfaces 134 and 136 to minimize frictional forces during the reciprocable interengagement of the outer tube 122 and the inner shaft 124. The slide surfaces are preferably fabricated from a polymeric material such as RULON 142 bearing tape, as described above.

As shown in FIGS. 14 and 15, the inner shaft 124 is hollow with an inner surface 138, which preferably has a circular cross-section and accommodates a male pyramid fitting 36 at its proximal end, as described above. The inner shaft 124 is preferably fabricated from a light-weight metal such as age-hardened aluminum, Also, as described above, the outer surface 128 of inner shaft 124 is preferably coated with a low friction material such as a TUFRAM synergistic coating and smeared with a lubricant such as a Krytox GPL 205 grease.

Figure 21:
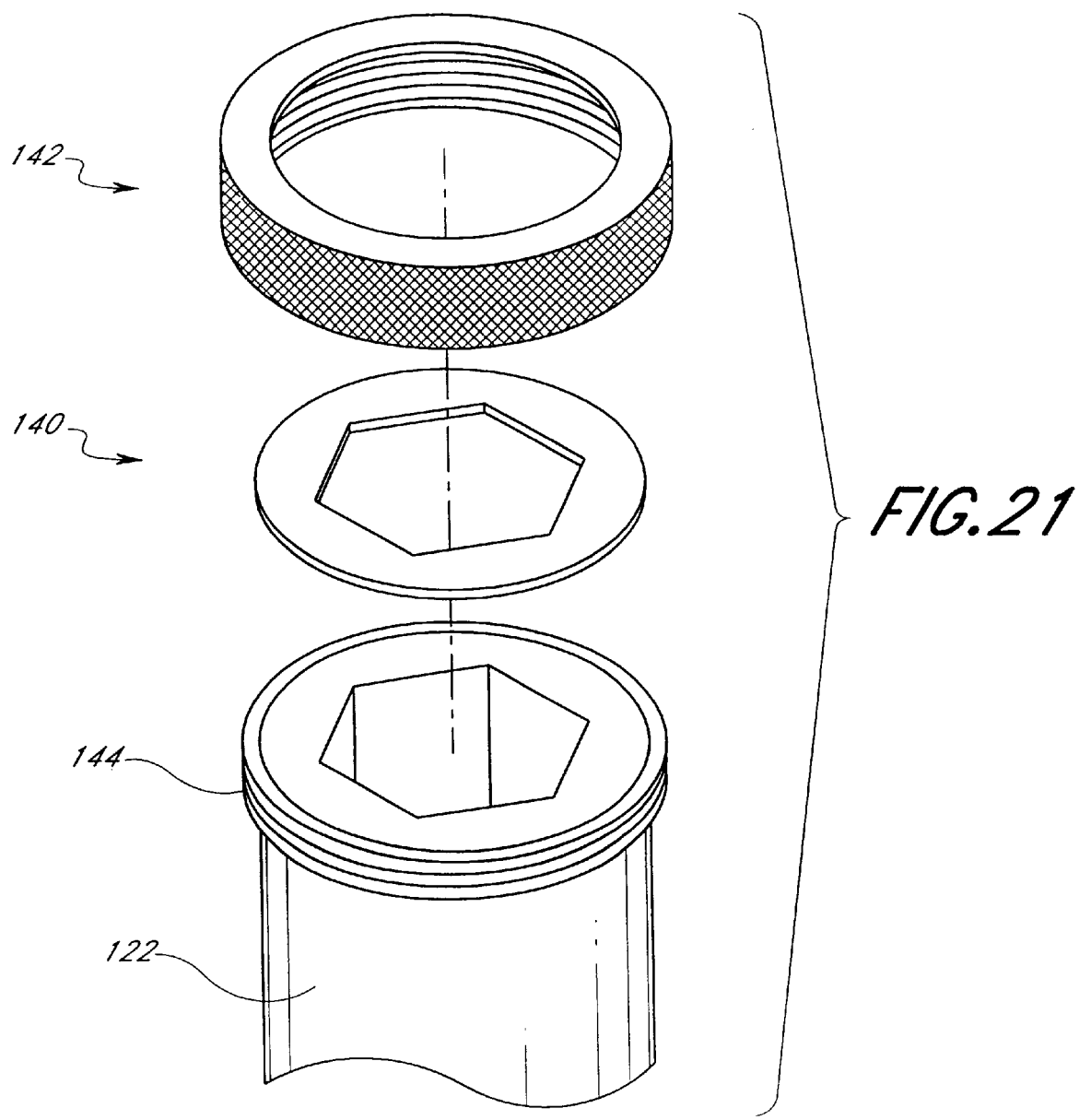
FIG. 21 is an exploded perspective view illustrating a preferred configuration of the grease seal assembly.

In order to prevent debris from entering between the outer pylon 122 and inner shaft 124, there is preferably provided a cuff, such as the torque-resisting cuff 34 described in connection with the embodiments of FIGS. 1–13. Such a cuff may be proximally secured to the inner shaft 124 and distally secured to the proximal end of the outer tube 122. Alternatively, there may be provided a grease seal element 140 as shown in FIGS. 21 and 14. Accordingly, the mouth of the mating opening at the proximal end of the outer tube 122 is circumscribed by a grease seal element 140 which is held in place by a cap 142 and ring 144 assembly. The grease seal element 140 preferably has a circular outer periphery and a hexagonal inner opening. The dimensions of the hexagonal inner opening closely match the dimensions of the outer cross-section of the inner shaft 124. The grease seal element 140 is preferably fabricated from a resilient material such as sheet urethane or teflon. Alternatively, nylon, silicone, or other suitable materials may be used, giving due consideration to the goal of durability. The ring 144 is adhesively bonded to the outer tube 122 using, for example, 3M #420/460 toughened epoxy. The cap 142 and ring 144 are matchingly threaded, which allows the cap 142 to be secured to the ring 144, thus holding the grease seal element 140 in position. The cap 142 and ring 144 are preferably fabricated from aluminum having an anodized finish.

The purpose of the grease seal element 140 is not necessarily to provide an air-tight seal, but rather to function as a "scraper" during the telescoping interaction of the outer tube 122 and the inner shaft 124. That is, the grease seal element, by scraping against the inner shaft 16, not only restricts the lubricating grease (which is smeared on the inner shaft 16, as discussed above) from exiting the body of the outer tube, but also hinders undesired contaminatory materials (such as dust) from entering the body of the outer tube 122. This minimizes wastage of the lubricating grease and protects the sliding surfaces of the reciprocating outer tube 122 and inner shaft 124. Also, the grease seal element 140 is conveniently and inexpensively replaceable by the user.

As mentioned above, the shock modules 22 and 120 are readily attachable to a variety of prosthetic feet, by utilizing well known prosthetic couplers. Moreover, any of a broad selection of couplers may be used, giving due consideration to the goal of providing a stable, long-lasting attachment. An example of an attachment of a shock module to a prosthetic foot having a horizontal attachment section is illustrated in FIG. 1A, which shows the shock module attached to a Flex-Walk® prosthetic foot 24 via a pyramid coupler 91 and female pyramid fitting 93. The female coupler is slipped over the lower extremity of the outer pylon 26 (or outer tube 122) and clamped into position. This assembly, as opposed to inserting a coupler inside the lower extremity of the outer pylon 26 (or tube 122), eliminates the possibility of the coupler interfering with the components internal to the outer pylon 26 (or tube 122). Recall that the outer pylon 26 may be cut to a desired length by the prosthetist or wearer, so that the support base 40 may be near to the lower end of the outer pylon 26 (or tube 122).

Alternatively, the shock modules 22 and 120 may be attached to a prosthetic foot having a vertical attachment section. An example of such an attachment is shown in FIGS. 22 and 23, in which the shock module is attached to a Sure-Flex® prosthetic foot 101 by utilizing a coupler comprising a mounting block 95 and a ribbing 97. Both the mounting block 95 and ribbing 97 are preferably fabricated from a compression molded graphite/epoxy or fiberglass/vinyl ester composite. The ribbing 97, which has a C-shaped cross-section, is bonded to the outer pylon 26 (or tube 122) after the pylon 26 (or tube 122) has been cut to the desired length. The mounting block 95 has a "ribbed" surface to mate with the "ridges" of the ribbing 97. Moreover, the mounting block 95 is equipped with two vertically aligned studs (not shown) that connect with the vertical attachment section 99 of the prosthetic foot 101.

In the attachment configuration shown in FIGS. 22 and 23, the shock module and the prosthetic foot 101 may be temporarily secured in place with band clamps (not shown) or can be permanently secured together by the user with an epoxy binder with or without overlying wet cloth lamination (not shown). A convenience of this attachment method is that the wearer can easily make minor adjustments in the length of the prosthesis via the vertical positioning of the mounting block 95 on the ribbing 97. Moreover, the mounting block 95 is also available in an "angled" design (not shown), so that the wearer can choose a desired angular offset between the shock module and the prosthetic foot 101.

Figure 24:
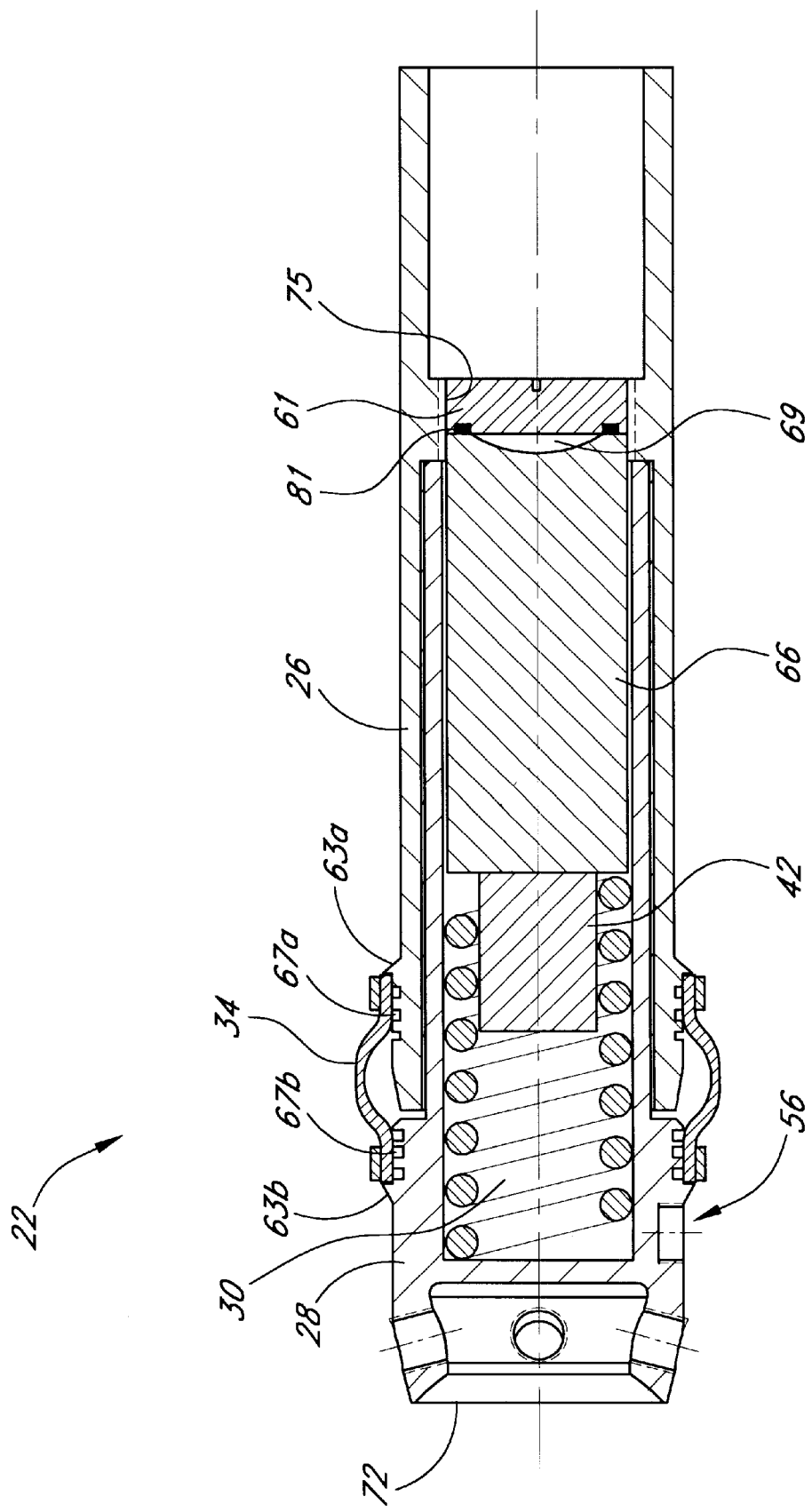
FIG. 24 is a cross-sectional view of an alternative shock module including two telescoping pylons.
Figure 25:
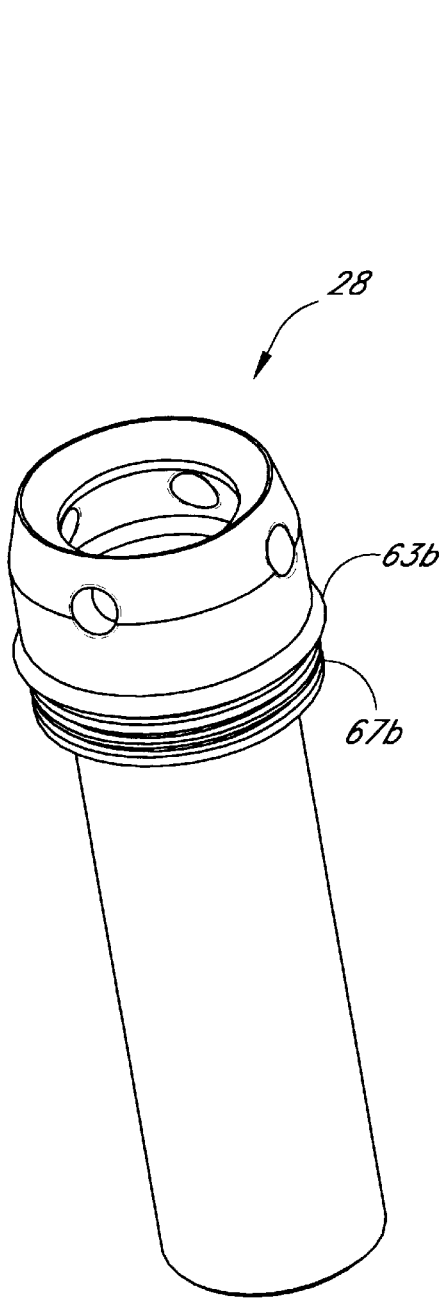
FIG. 25 is a perspective view of the first pylon of FIG. 24.
Figure 26:
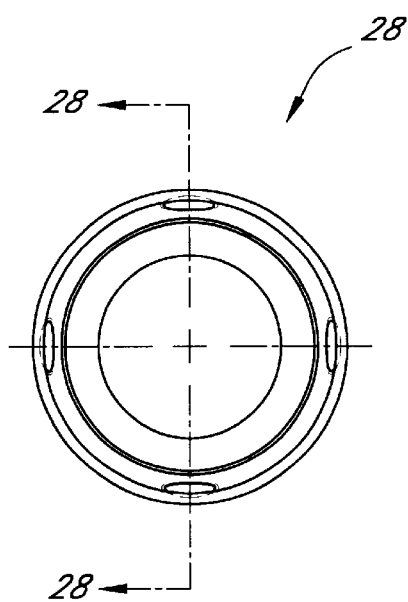
FIG. 26 is a top view of the first pylon of FIG. 24.
Figure 27:
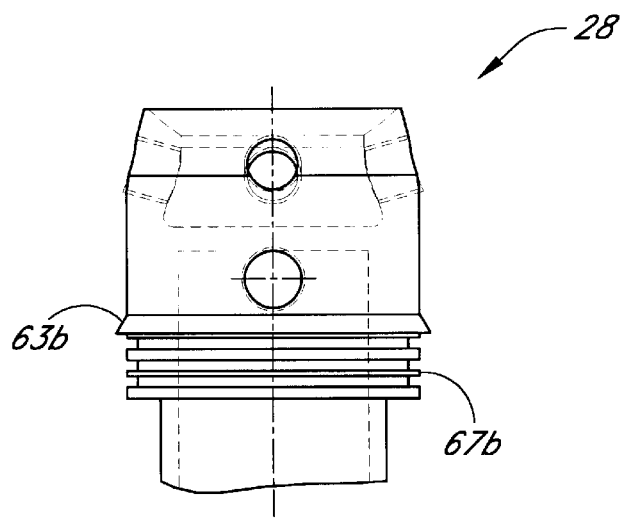
FIG. 27 is a side view of the head of the first pylon of FIG. 24.
Figure 28:
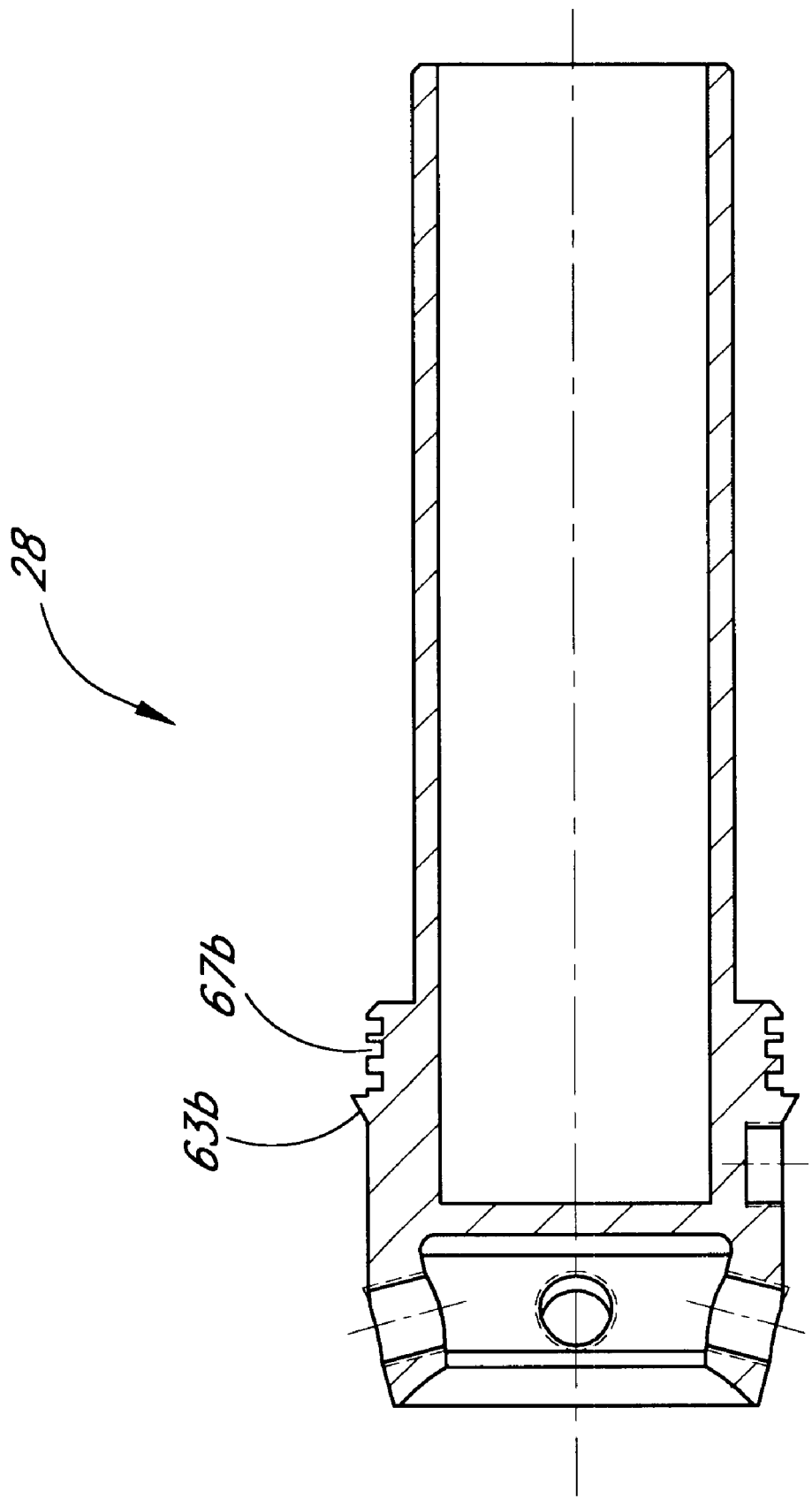
FIG. 28 is a cross-section view of the first pylon of FIG. 24.

FIG. 24 illustrates an alternative shock module having features in accordance with another embodiment of the present invention. This shock module is similar to that described in FIGS. 7 and 8 above, and therefore identical reference numerals are used to identify corresponding parts. Shock module includes outer pylon 26 and inner pylon 28, shaped and adapted for smooth relative motion. Pylons 26 and 28 are preferably slidingly and rotationally interengaged with each other while retaining their operative horizontal alignment with each other through a relatively close fit between the inside dimensions of outer pylon 26 and the outside dimensions of inner pylon 28. The inner pylon 28 has an enlarged outside diameter at its proximal end, approximately equal to the outside diameter of the outer pylon 26. This enlarged diameter portion of the inner pylon 28 therefore extends beyond the proximal end of the outer pylon 26 and does not extend into the outer pylon 26.

As described with respect to FIG. 7 above, pylon 28 also has a female pyramid fitting 72 at its proximal end, for attachment to a stump socket (not shown). Outer pylon 26 preferably has a cylindrical outer surface to facilitate the attachment of various types of prosthetic feet using conventional prosthetic couplers. For example, the lower end of pylon 26 may be attached to a prosthetic foot having a horizontal attachment section, such as the prosthetic foot 24 in FIG. 1, or to a prosthetic foot having a vertical attachment section. Both types of attachments are well known in the prosthetic foot art.

Shock module 22 preferably includes a hybrid spring-fluid resilient element, comprising an internal coil compression spring 30 in combination with a compressible fluid such as air. Spring 30 is preferably proximally fixed with respect to inner pylon 28 and distally fixed with respect to outer pylon 26 via spring support 66. Optionally, a valve 56 is provided within pylon 26 to vary the pressure of the fluid inside of shock module 22. A torque-resisting cuff 34 provides torsion-resistance to the prosthesis and also keeps dirt and other debris from getting between pylons 26 and 28 and affecting their relative motion.

Figures 29, 30:
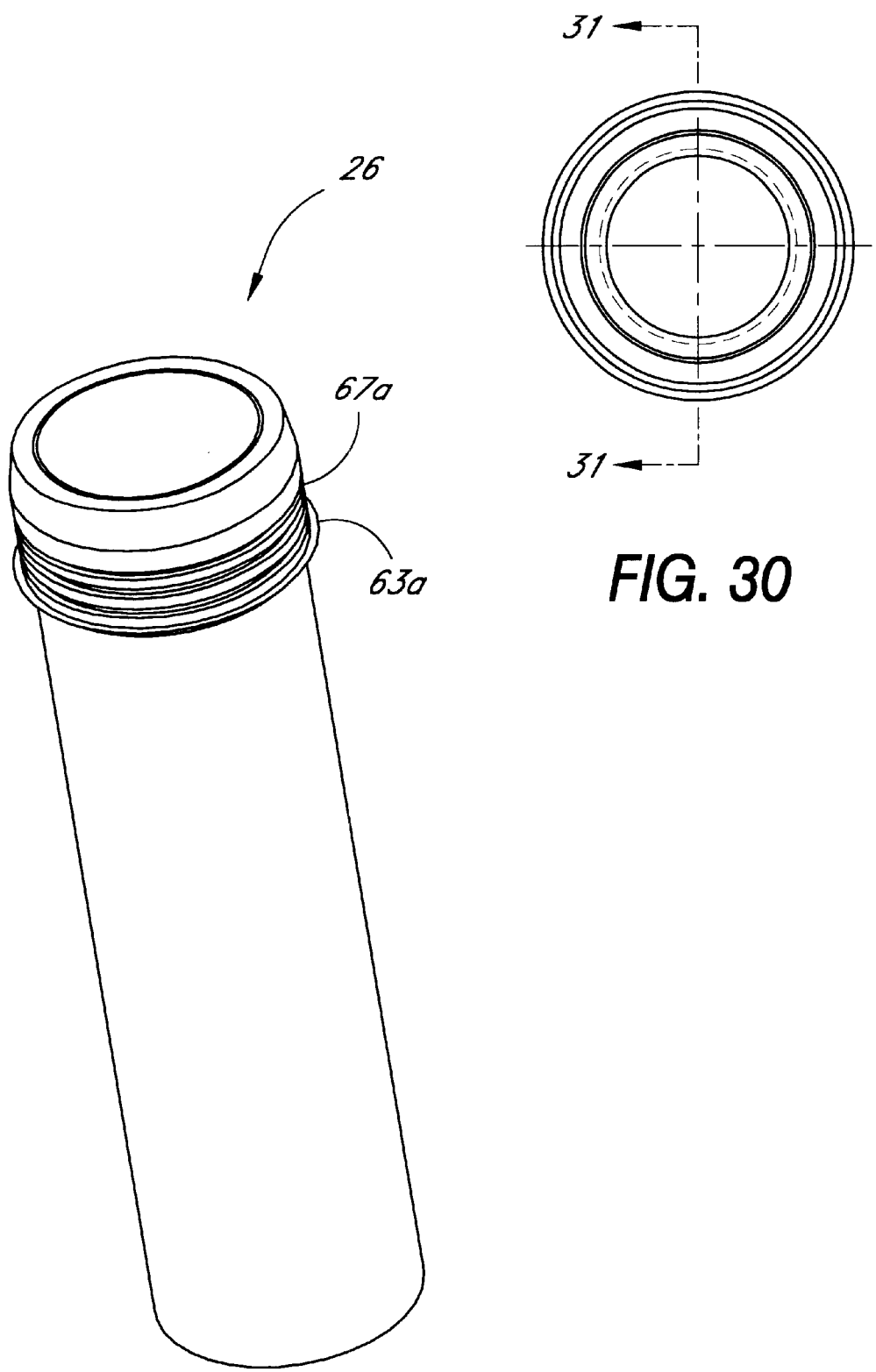
FIG. 29 is a perspective view of the second pylon of FIG. 24.
FIG. 30 is a top view of the second pylon of FIG. 24.
Figure 31:
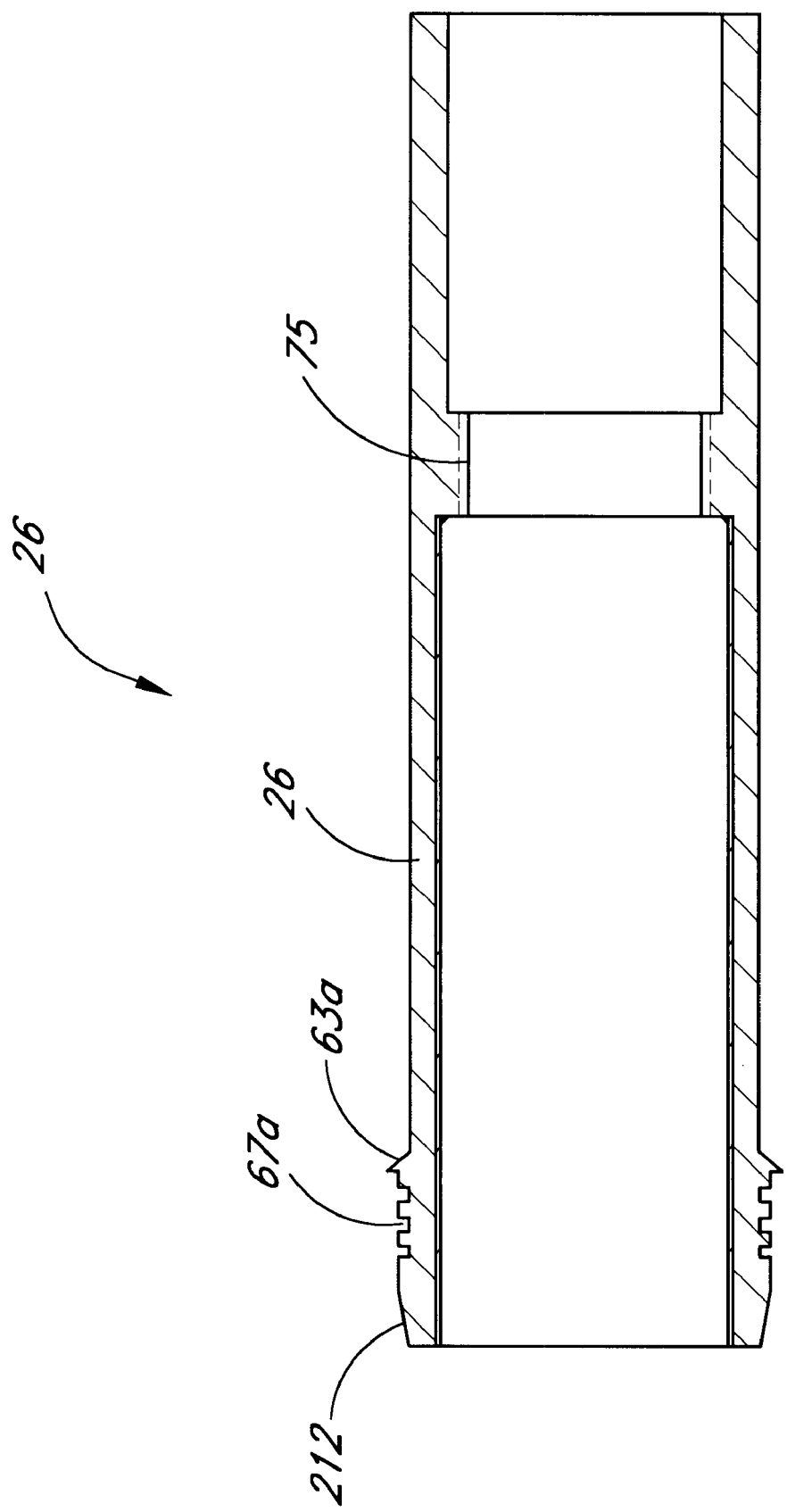
FIG. 31 is a cross-sectional view of the second pylon of FIG. 24.
Figure 36:
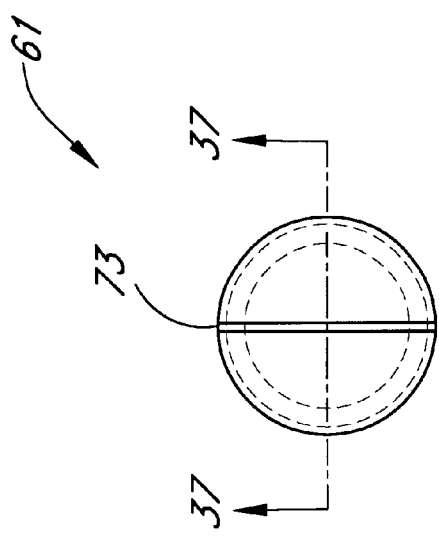
FIG. 36 is a top view of the plug of FIG. 35.

Cuff 34, shown more particularly in FIGS. 32–34, has a distal end 34a and a proximal end 34b, each of these ends adapted and configured to engage corresponding portions of the outer and inner pylons, respectively. Accordingly, outer pylon 26, shown more particularly in FIGS. 29–31, is configured with a circular ridge 63a on its exterior at its proximal end to help maintain the distal position of the cuff 34 relative to the pylon 26. Pylon 26 further includes grooves 67a beyond the circular ridge 63a adapted to engage the distal end of the cuff 34. Similarly, on the exterior of the enlarged diameter portion of the inner pylon 26, shown more particularly in FIGS. 25–28, grooves 67b are provided below the ridge 63b to engage the proximal end 34b of the cuff 34. As shown in FIG. 24, the cuff 34 is further secured to the pylons through use of ring clamps 50 which provide air-tight seals.

The torque-resisting cuff 34 is preferably configured to oscillate between a relatively straight vertical position, when the outer pylon and inner pylon are moved relatively far apart, and a curved position, when the outer pylon and inner pylon are compressed relative to one another. FIG. 24 illustrates the shock module 22 in a fully compressed configuration such that the cuff 34 is curved and the inner pylon 28 extends as far as possible into the outer pylon 26. More particularly, when fully compressed the enlarged outer diameter portion of the inner pylon 28 preferably abuts against the proximal end of the outer pylon 26.

Figure 40:
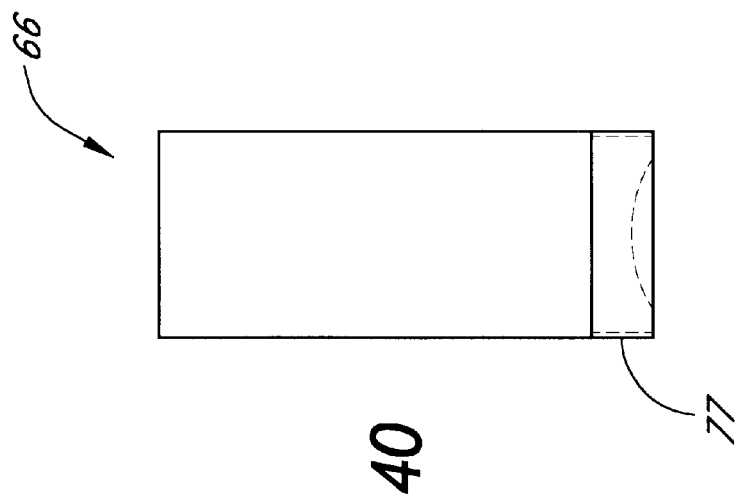
FIG. 40 is a side view of the spring support of FIG. 39.
Figure 41:
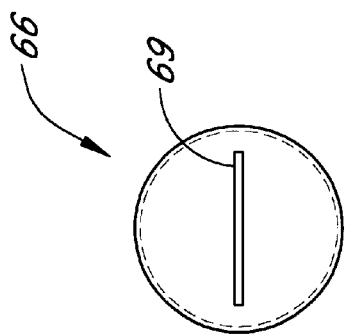
FIG. 41 is a bottom view of the spring support of FIG. 39.
Figure 39:
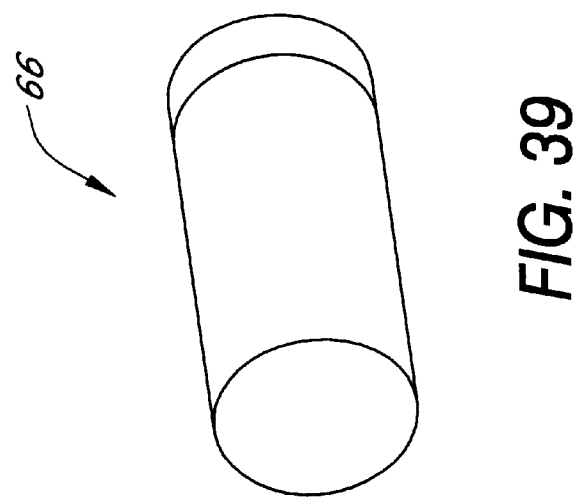
FIG. 39 is a perspective view of a spring support used in conjunction with the outer pylon of FIG. 24.

As shown in FIGS. 24 and 31, pylon 26 preferably includes an internally threaded surface 75 between its proximal and distal ends with an inner wall diameter that is less than that of its adjacent surfaces. This portion of the inner wall with the increased wall thickness acts as a support base for the inner pylon 28 when the shock module is in its fully compressed configuration. The threaded surface 75 preferably engages a spring support 66, shown more particularly in FIGS. 39–41. The spring support 66 includes an externally threaded surface 77 at its distal end which engages the internally threaded surface 75. The spring support 66 engages the inner wall of the pylon 26 through the use of slot 69 for screwing the spring support 66 into the surface 75. When engaged with the inner wall of the pylon 26, the spring support 66 extends proximally within the pylon 26 toward the inner pylon 28 and forms an annulus within which inner pylon 26 axially moves. As described with respect to FIG. 7 above, a bottom spring end fitting 42 is attached to the top of support 66, to which the bottom end of spring 30 is attached.

Figure 38:
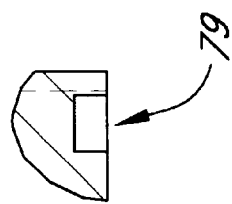
FIG. 38 is an enlarged cross-sectional view of a portion of the plug of FIG. 35.
Figure 35:
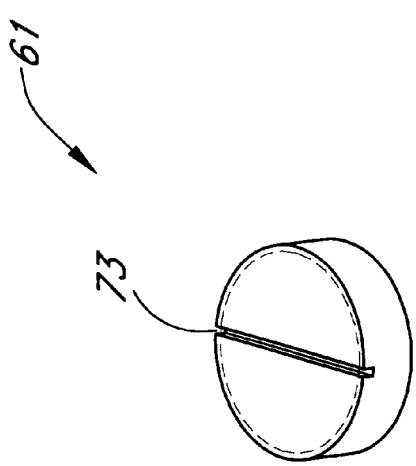
FIG. 35 is a perspective view of a plug used in conjunction with the inner pylon of FIG. 24.
Figure 37:
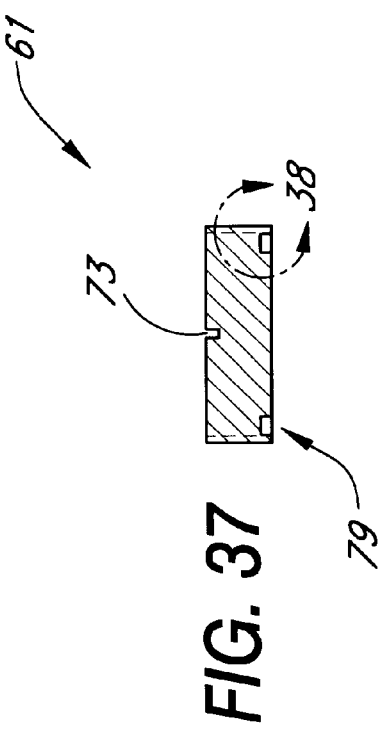
FIG. 37 is a cross-sectional view of the plug of FIG. 35.

In one embodiment, an end cap 61 preferably seals the outer pylon 26 below the spring support 66. As shown more particularly in FIGS. 35–38, the body of end cap 61 is preferably threaded and configured to engage the internally threaded surface 75 of outer pylon 26. This cap preferably has a slot 73 for screwing the cap into the threaded surface 75 to secure the position of the spring support. FIGS. 37 and 38 further illustrate that the end cap 61 preferably has a notch 79 on the surface adapted to engage the spring support 66. This notch is configured to receive an O-ring 81 (shown in FIG. 24) for sealing the bottom of the outer pylon 26.

Figure 42:
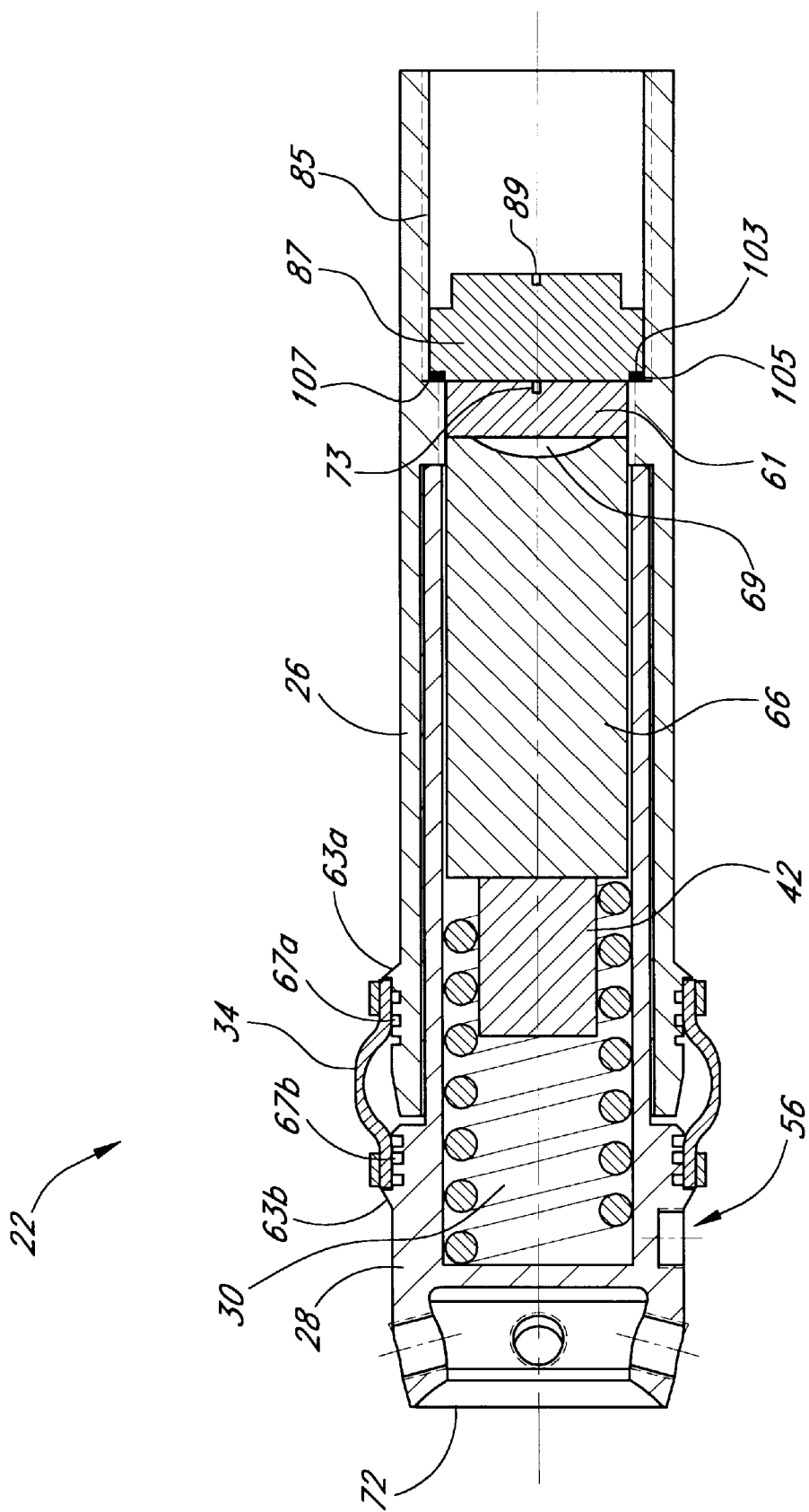
FIG. 42 is a cross-sectional view of an alternative shock module.

FIG. 42 illustrates another embodiment of a shock module similar to that of FIG. 24. In this embodiment, end cap 61, which screws into internally threaded surface 75, does not have a notch for placement of an O-ring. Rather, sealing of the bottom of the outer pylon is achieved by providing additional internal threading below surface 75 on surface 85 extending to the distal end of the outer pylon 26 for receiving a cover cap 87 having mating external threading. The cover cap 87 is then preferably screwed into internally threaded surface 85 using slot 89 to secure the cover cap 87 against the end cap 61. Along the surface that secures end cap 61, the cover cap 87 is provided with an O-ring notch 103 that abuts against the horizontal surface 107 between the surfaces 75 and 85. By providing an O-ring 105 into this notch, when the cover cap is screwed into the internally threaded surface 85 against the horizontal surface 107, the O-ring 105 is compressed to provide an air-tight seal with respect to the interior of pylon 28.

Figure 43:
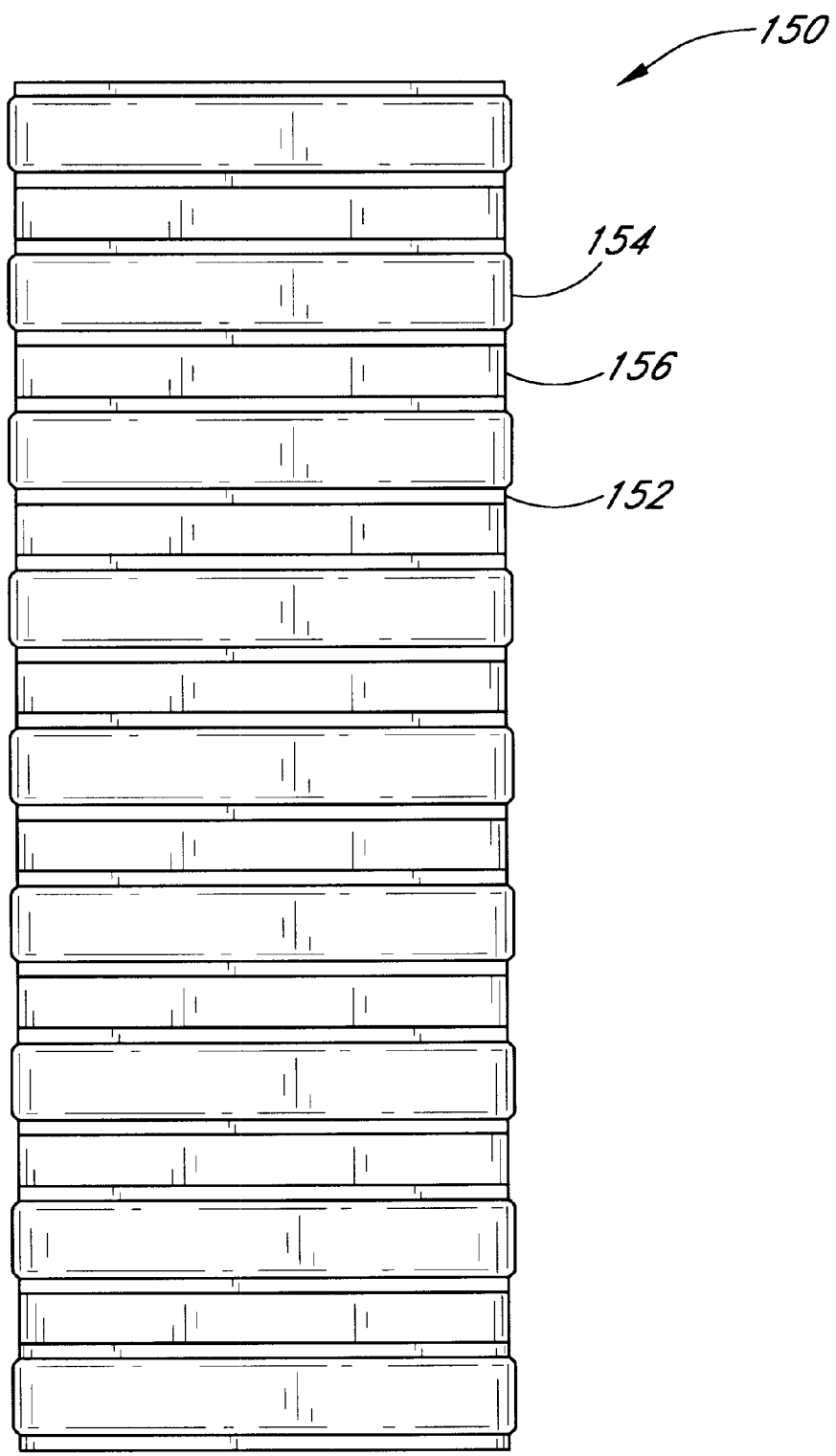
FIG. 43 is a side view of a composite disk spring according to one embodiment of the present invention.
Figure 44:
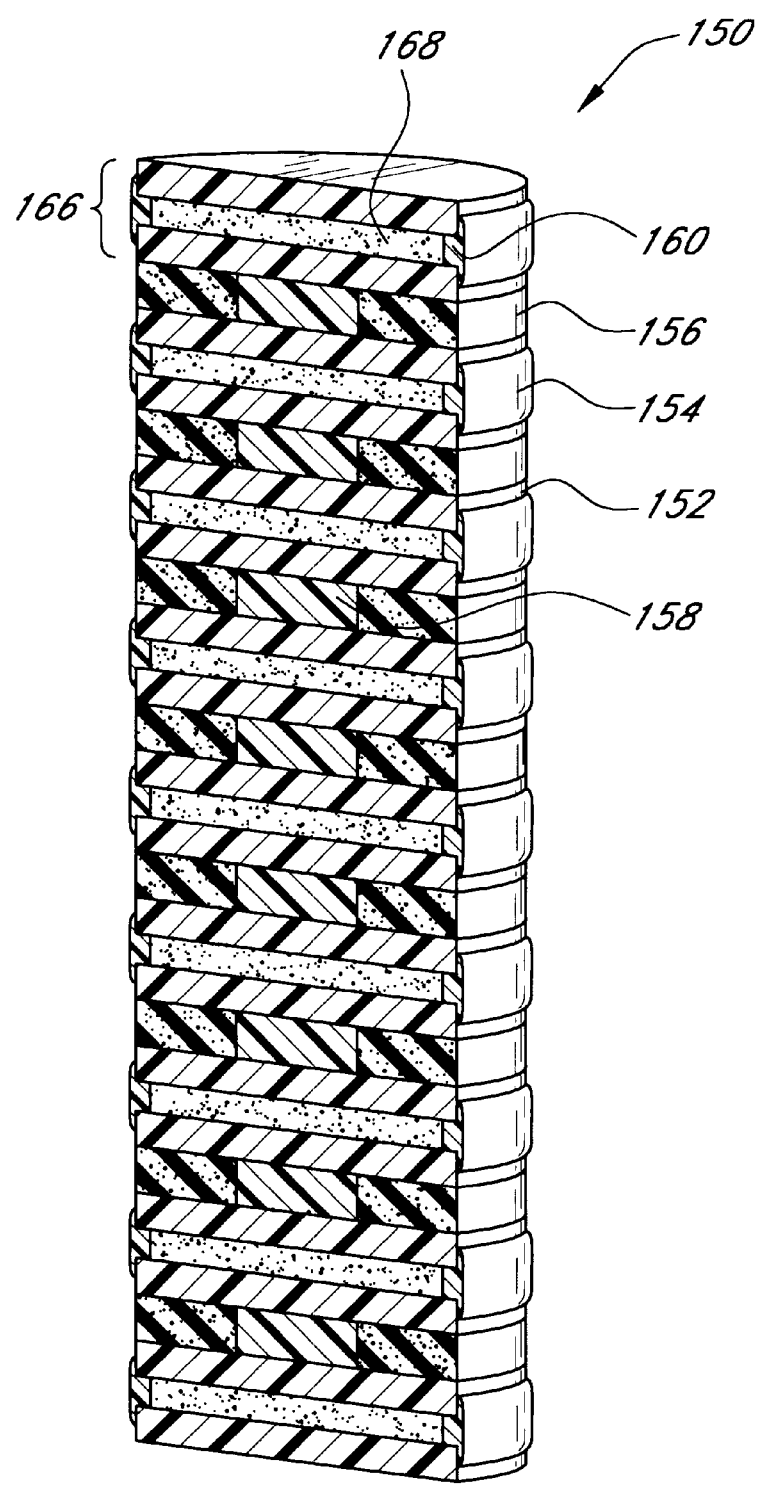
FIG. 44 is a cross-sectional view of the composite disk spring of FIG. 43.

In the embodiments described above, a coil compression spring 30 may be used to provide impact absorption to the prosthesis. It will be appreciated that other types of springs or compression members may also be used for providing the desired impact absorption. FIGS. 43–45 illustrate a disk spring 150 that may be used in accordance with the embodiments above in place of the coil compression spring 30. As shown in FIG. 43, the spring 150 preferably incorporates a plurality of interconnected disks 152. More preferably, these disks are connected by metal rings 154, foam rings 156 and other components described below.

As illustrated more particularly in FIG. 44, the disks 152 are arranged in pairs along the length of the spring 150, with each pair of disks 152 attached to one of the rings 154. The ring 154 has an outer diameter that is preferably slightly greater than the diameter of the disks 152, and an inner diameter that corresponds to the diameter of the disks. As shown in FIGS. 44 and 45, each ring 154 also includes an internal support section 160 that is preferably integrally formed with the ring. The support section 160 is preferably centered longitudinally along the inner surface of the ring 154 and extends inward toward the center of the ring such that the inner diameter of the internal support section 160 is smaller than the inner diameter of the ring 150. This internal support section thereby defines an upper surface 162 and a lower surface 164 within the ring 154 on which to seat the disks 152. The disks 152 when seated on these surfaces 162 and 164 preferably have a thickness that extends above the upper and lower edges of the ring 154.

Figure 46:
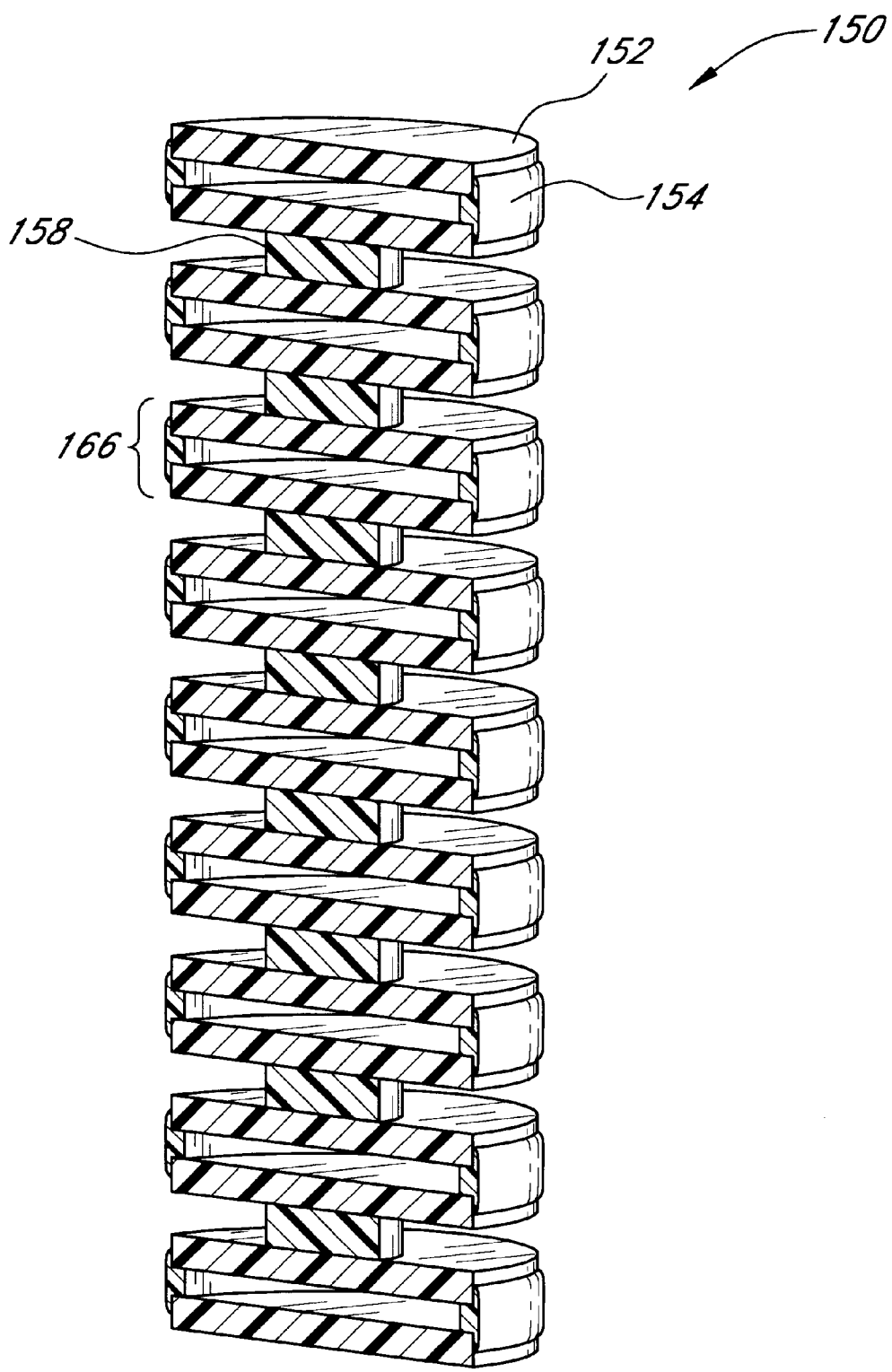
FIG. 46 is a cross-sectional view of the composite disk spring of FIG. 43, shown without foam rings or foam disks for clarity.

The combination of a ring 154 and a pair of disks 152 on the upper and lower sides thereof preferably defines one module 166 of the spring 150. In one preferred embodiment, provided between the two disks of each module, and within the space defined by the support section 160, is a foam disk 168. The foam disk 168 provides stability to the composite disk spring 150. For clarity, FIG. 46 illustrates the spring 150 without the foam disks 168. The ring 154 is preferably made of metal, and in one embodiment, is made of aluminum. The disks 152 are preferably made of a fiber-reinforced composite material such as fiber-reinforced graphite and epoxy.

Figure 47:
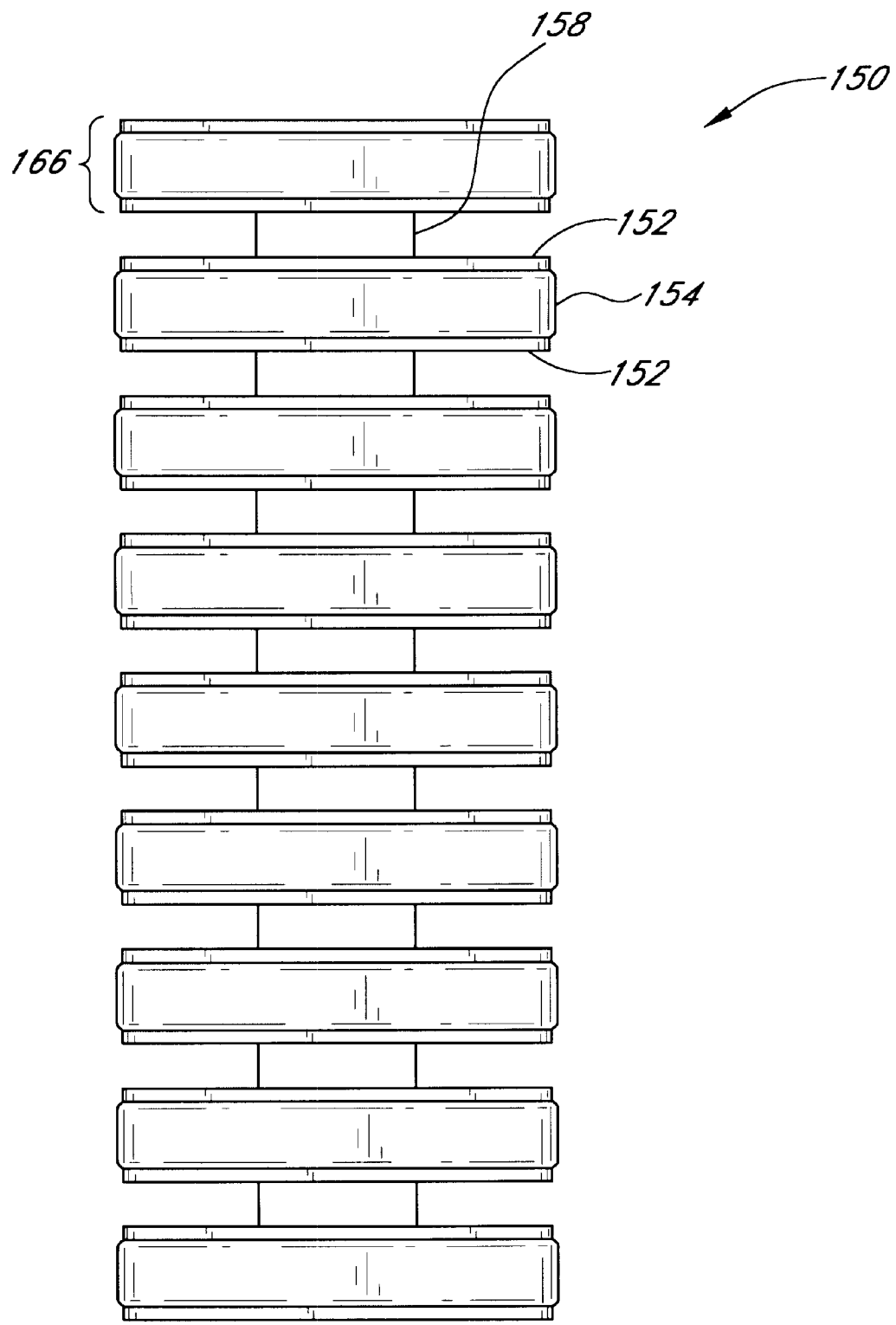
FIG. 47 is a side view of the composite disk spring of FIG. 43, shown without foam rings for clarity.

Each module 166 of the spring 150 is preferably stacked over one another in the manner shown in FIGS. 46 and 47. These figures show nine such modules 166, comprising a total of nine rings 154 and eighteen composite disks. A spacer or button 158 is provided between each of the modules, such that when nine modules are used, eight buttons will be incorporated into the design of the spring 150. The buttons 158 are preferably made of a thermoplastic elastomer material, more preferably a urethane material. FIGS. 43 and 44 illustrate that a foam ring 156 may preferably be provided surrounding the urethane button 158 between each of the modules 166. This foam ring 156 advantageously adds stability to the spring structure.

Figure 48:
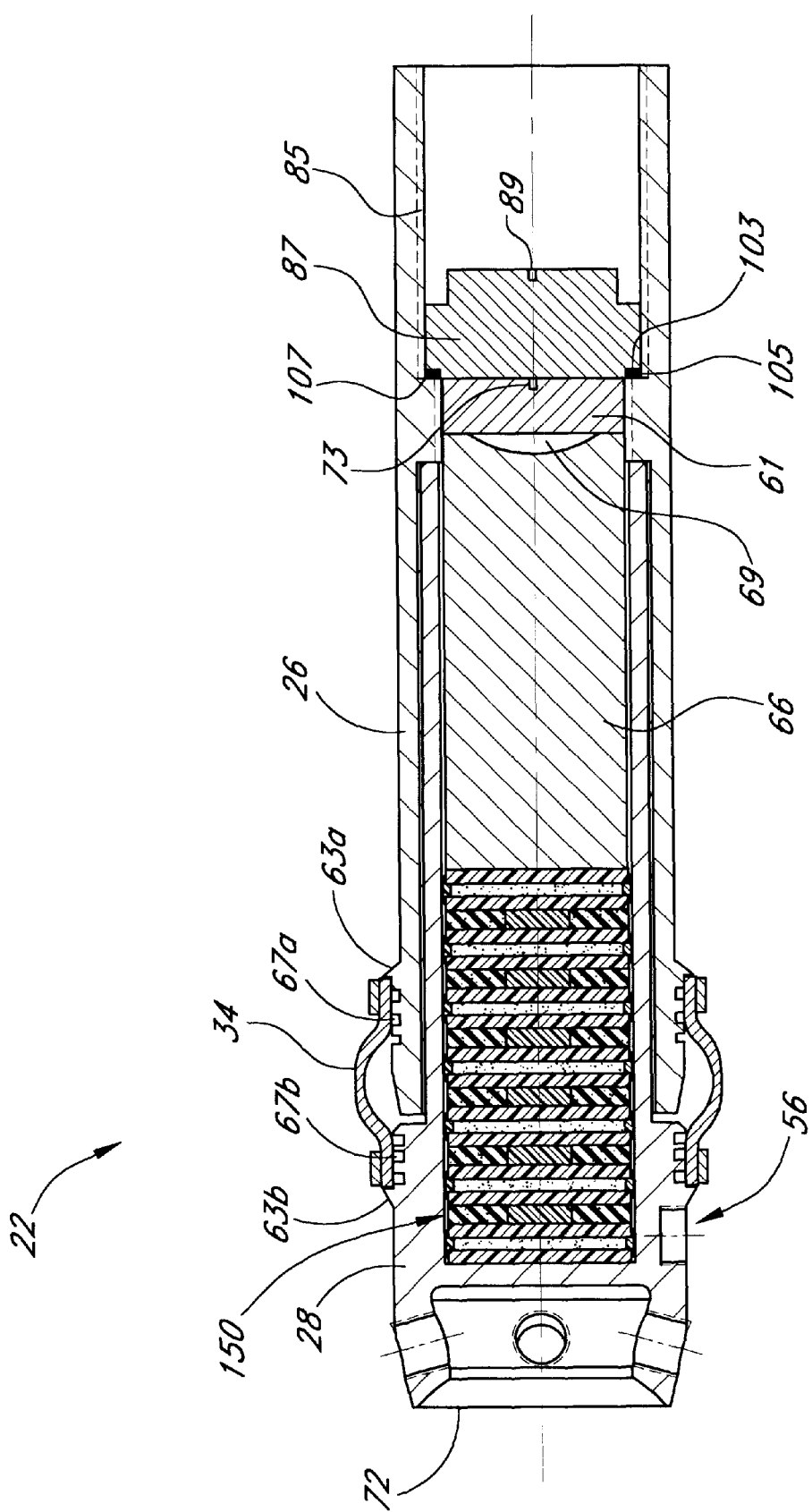
FIG. 48 is a cross-sectional view of a shock module incorporating a composite disk spring.

FIG. 48 illustrates the composite disk spring 150 implemented into the shock module of a prosthetic foot, such as described above. Similar to the embodiment of FIG. 42 above, the spring 150 is inserted into inner pylon 28. The compression disk spring 150 extends within the pylon 26 from the upper end of the bore within the pylon 28 to the support 66 which is threaded into the outer pylon 26, as described above. In one embodiment, the composite disk spring 150 has a length of about 4 inches and a diameter of about one inch. It will be appreciated that the composite disk spring 150 may have other dimensions as well, and may be implemented with any of the embodiments described above incorporating telescoping pylons.

When incorporated into a shock module, as shown in FIG. 48, composite disk spring 150 provides impact absorption by the force of the buttons 158 on the disks 152. When a compressive force is applied to the shock module, the buttons 158 press against the center of the composite disks 152 causing them to deflect and bow concavely inward towards the foam disk 168. The resistance of the disks to this deflection, as well as the compression of the buttons 150, create the desired spring rate, which in one embodiment, may be between about 300 and 750 lb/in. Optionally, the composite disk spring may be slightly preloaded. It will be appreciated that the spring rate of the composite disk spring may be adjusted by selecting disks 152 of varying thickness and stiffness. Furthermore, it is also contemplated that the spring rates of each module 166 may be varied to achieve a desired performance.

Figure 49:
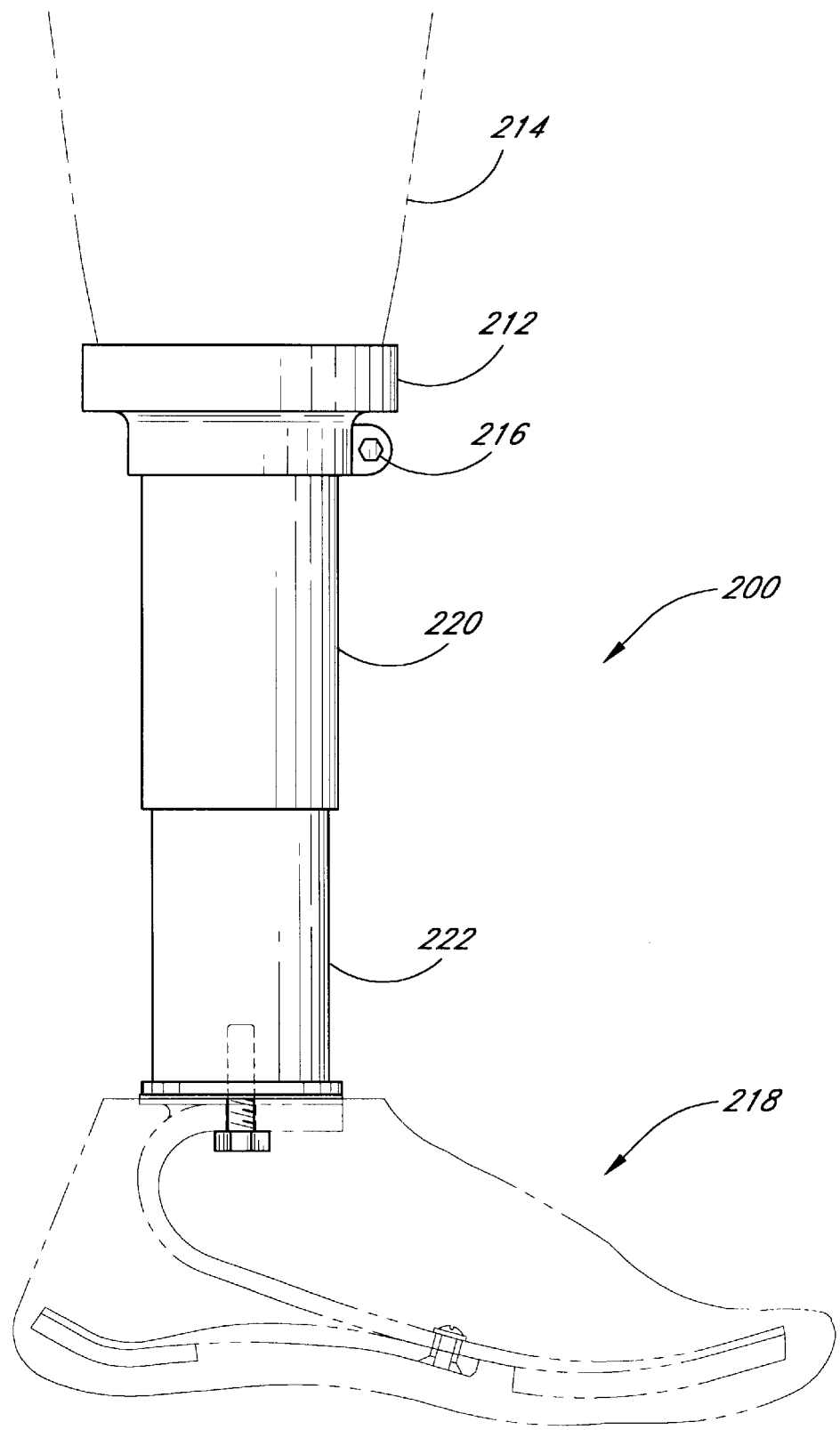
FIG. 49 is a side elevation view of a shock absorbing prosthesis constructed in accordance with another embodiment of the present invention, the socket and prosthetic foot, being shown for illustrative purposes only.

FIG. 49 shows a vertical shock absorbing prosthesis 200 having features according to another embodiment of the present invention. In the preferred embodiments of the present invention, the prosthesis 200 is located above the ankle region and below the knee of the amputee. A connector 212, such as a 30 mm Graphite Clamp available from Flex-Foot, Inc. in Aliso Viejo, Calif., is utilized for attaching a socket 214 or other device for receiving the stump of an amputee. The socket 214 is received into the upper portion of the connector 212 as shown. The connector 212 is positioned at the upper or proximal end of the prosthesis 200 and is preferably securely fixed by tightening of a bolt 216. Of course, other connectors known to those of ordinary skill in the art may be utilized as desired. A prosthetic foot 218, shown here as the FLEX-WALK™ from Flex-Foot, Inc., is attached to the lower or distal end of the prosthesis 200. Other types of flexible or nonflexible prosthetic feet may alternately be used without loss of advantage from the present invention. The foot 218, as well as connector 212, may be either permanently or temporarily (demountably) attached to the prosthesis 200. Advantageously, this allows for interchangeability according to the amputee's needs.

Figure 54:
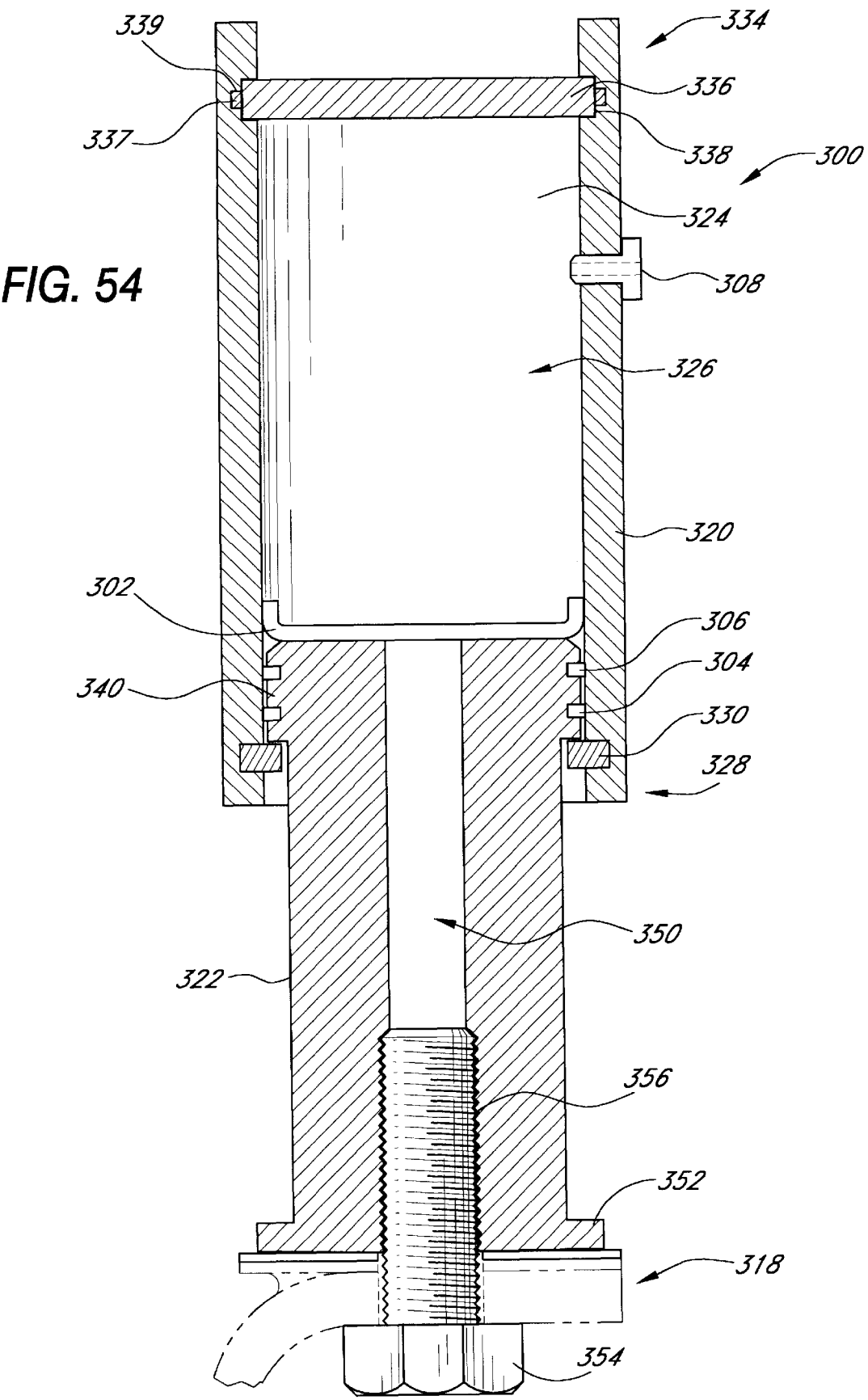
FIG. 54 is a longitudinal cross-section of another preferred embodiment of a shock absorbing prosthesis constructed in accordance with the present invention.

The prosthesis 200 generally comprises an outer and an inner cylinder or pylon 220, 222, respectively. The lower or distal, inner pylon 222 is slidably received within the upper or proximal, outer pylon 220. Alternatively, the pylons 220, 222 may be arranged in the opposite fashion, where a proximal, inner pylon 222 is slidably received within a distal, outer pylon 220. A compression member or assembly 224, 324, two examples of which are illustrated in FIGS. 49 and 54, is provided within a chamber 226 of the outer pylon 220. The member 224, 324 is subjected to compressive force by axial motion of the inner pylon 222 into the outer pylon 220.

The compression member 224 of the vertical shock absorbing prosthesis 200 constructed in accordance with this embodiment preferably provides nonlinear deflection characteristic. That is, during normal compression-decompression cycling, the prosthesis has a generally compliant deflection characteristic. However, for large deflection forces, the prosthesis becomes more stiff to prevent bottoming out. An impact force on the prosthesis 200 results in a rate of deflection of the compression member 224 near its point of maximum compression that is more gradual than for spring elements having linear load-deflection characteristics. This is discussed in greater detail in connection with FIG. 53.

Figure 50:
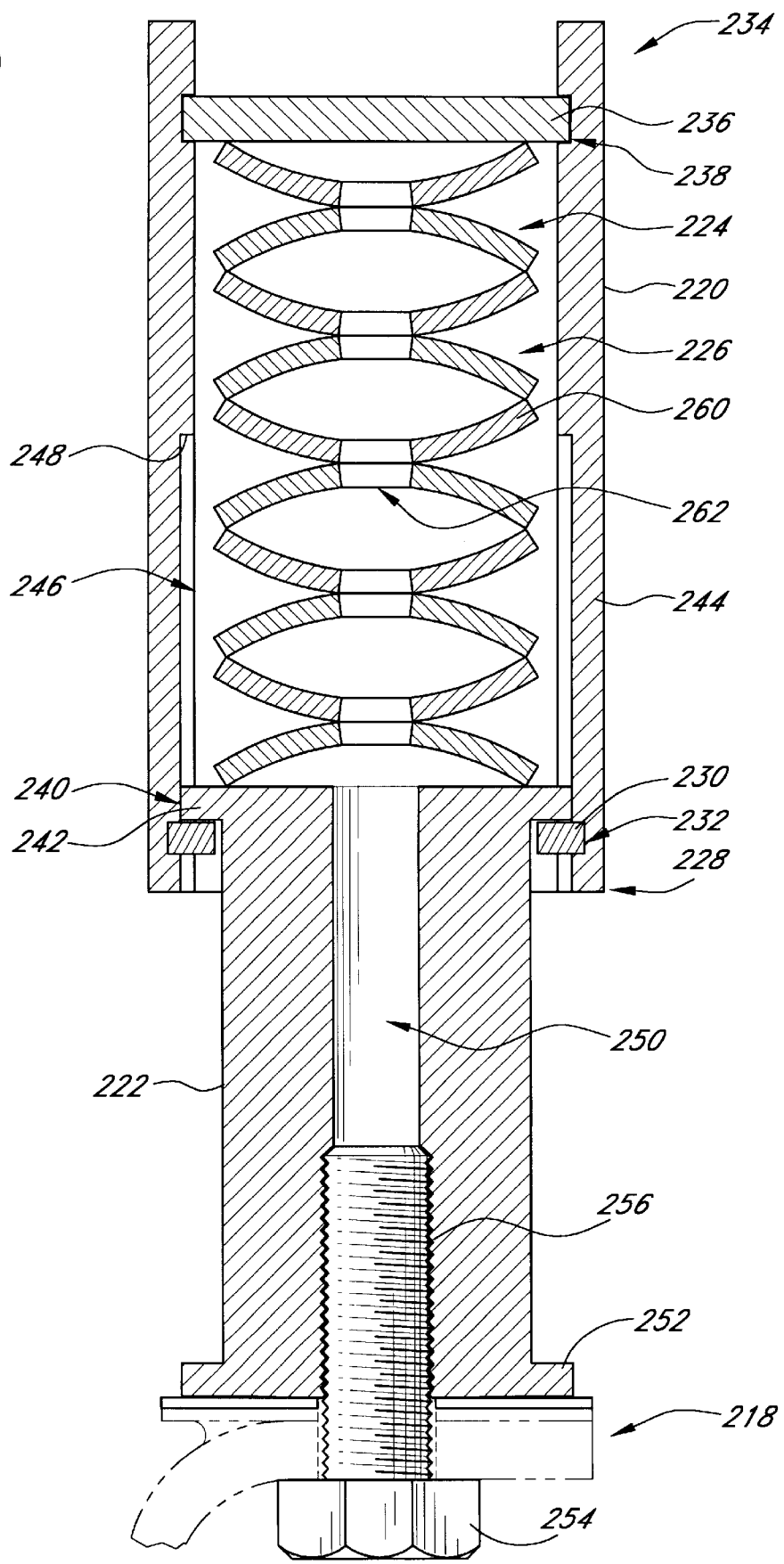
FIG. 50 is a longitudinal cross-section of another embodiment of a shock absorbing the prosthesis of the present invention.

Referring now in detail to FIG. 50, the outer pylon 220 is generally cylindrical. In this embodiment, a distal end 228 of the outer pylon 220 includes an annular element or spring clip 230 which is received in a groove 232 on the interior of the outer pylon 220 for preventing the inner pylon 222 from becoming dislodged after assembly. A proximal end 234 of the outer pylon 220 includes a disk 236 received into a groove 238 formed on the interior of the proximal end 234. Thus, a chamber 226 is formed between the disk 238 at the proximal end 234 of the outer pylon 220 and a proximal portion 240 of the inner pylon 222.

The inner pylon 222 includes a projection 242 formed radially outward at the proximal portion 240. A distal portion 244 of the outer pylon 220 comprises a longitudinally extending recess 246 on the interior which is sized to fit with the projection 242 of the inner pylon 222. The projection 242 of the inner pylon 222 is limited in its longitudinal travel within the outer pylon 220 by a wall 248 at the proximal end of the recess 246 and by the annular element 230 at the distal end 228 of the outer pylon 220.

The inner pylon 222 also includes a central channel 250 running through its length. A base portion 252 is located at the distal end of the inner pylon 222. The base portion is either formed as part of the inner pylon 222 or as a separate plate and serves as a limiter to the downward motion of the outer pylon 220, as well as an attachment surface for the prosthetic foot member 218. A bolt 254 is engaged at a threaded portion 256 of the distal end of the channel 250 to allow securement of the foot member 218. Although the embodiments of the prosthesis are described to have the outer pylon 220 positioned proximal to the inner pylon 222, the opposite positioning is also possible in the present embodiment. Further, although circular pylons 220, 222 are described, other shapes may be employed while retaining the advantages of the present embodiment.

For the inner and outer pylons 220, 222, it is preferred that a relatively strong, lightweight, and durable material be used, such as a composite of fiber and resin. Such fibers may include, for example, carbon graphite, fiberglass, kevlar and the like. In laminated and/or chopped form, these fibers may be polymer impregnated with a thermoplastic or thermosetting resin, such as epoxy, polyethylene, polypropylene, or the like. Alternately, titanium, aluminum, extruded nylon, or other suitable materials having strength and durability may be utilized.

The mating surfaces of the pylons 220, 222 are preferably coated with a material to minimize friction between the pylons, the compression member 224. A nonstick coating, such as Teflon™ by DuPont or Silverstone™, may be used to minimize the frictional resistance between contacting surfaces of the prosthesis 200.

In the embodiment shown in FIG. 50, compliance is provided through the use of Belleville springs 260. This type of spring element 260 has characteristics that are desirably different from conventional coil springs, in that its material and structure result in nonlinear load-deflection characteristics as described below. Generally, a Belleville spring 260 is formed of resilient material, well known to those skilled in the art, and has a generally coned-disk shape, with an optional aperture 262 centrally located thereon. As shown in FIGS. 50 and 51a–55b, the springs are placed in an alternating convex up 260a, concave up 260b sequence, as shown. An optional elongated bolt 264, shown in FIG. 52, may be used to maintain alignment of the springs 260 during assembly and use.

Figure 51A:
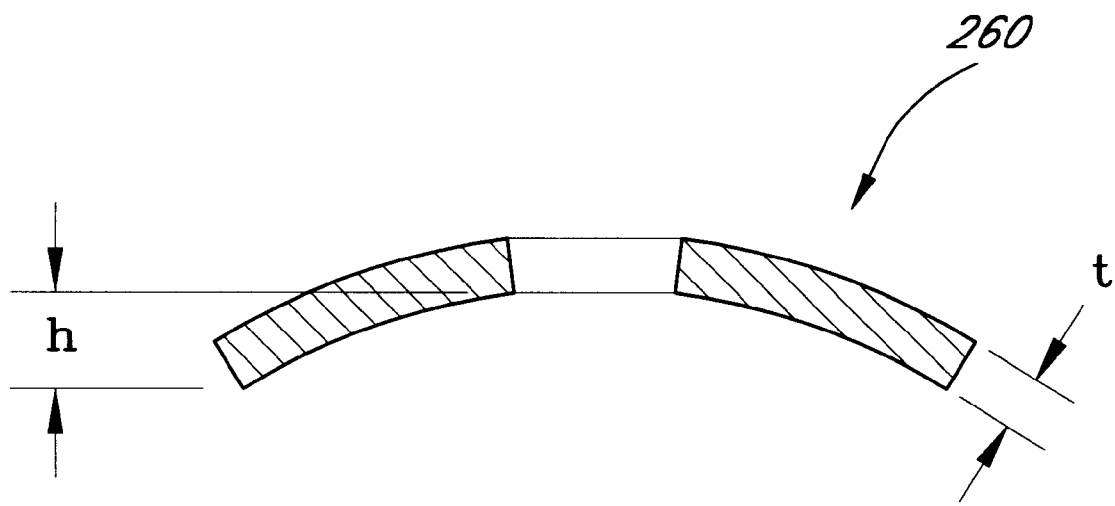
FIG. 51a shows a Belleville spring in an uncompressed state.
Figure 51B:
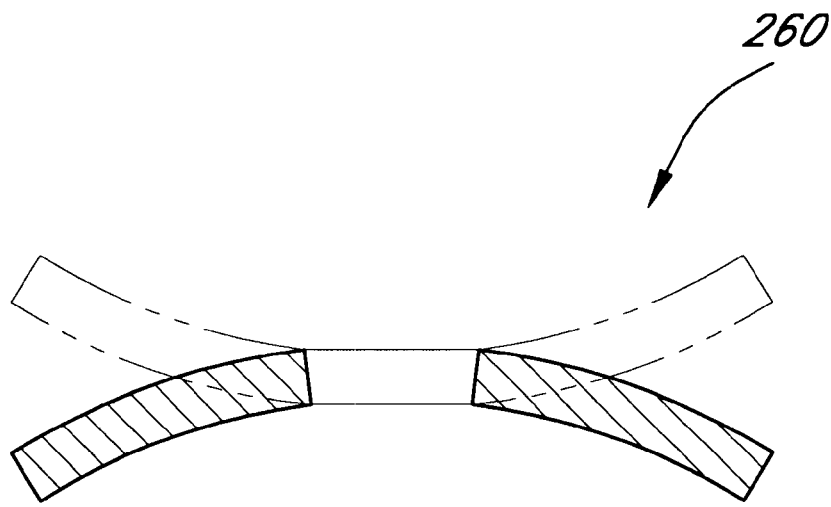
FIG. 51b shows a Belleville spring in an inverted state in phantom.
Figure 53:
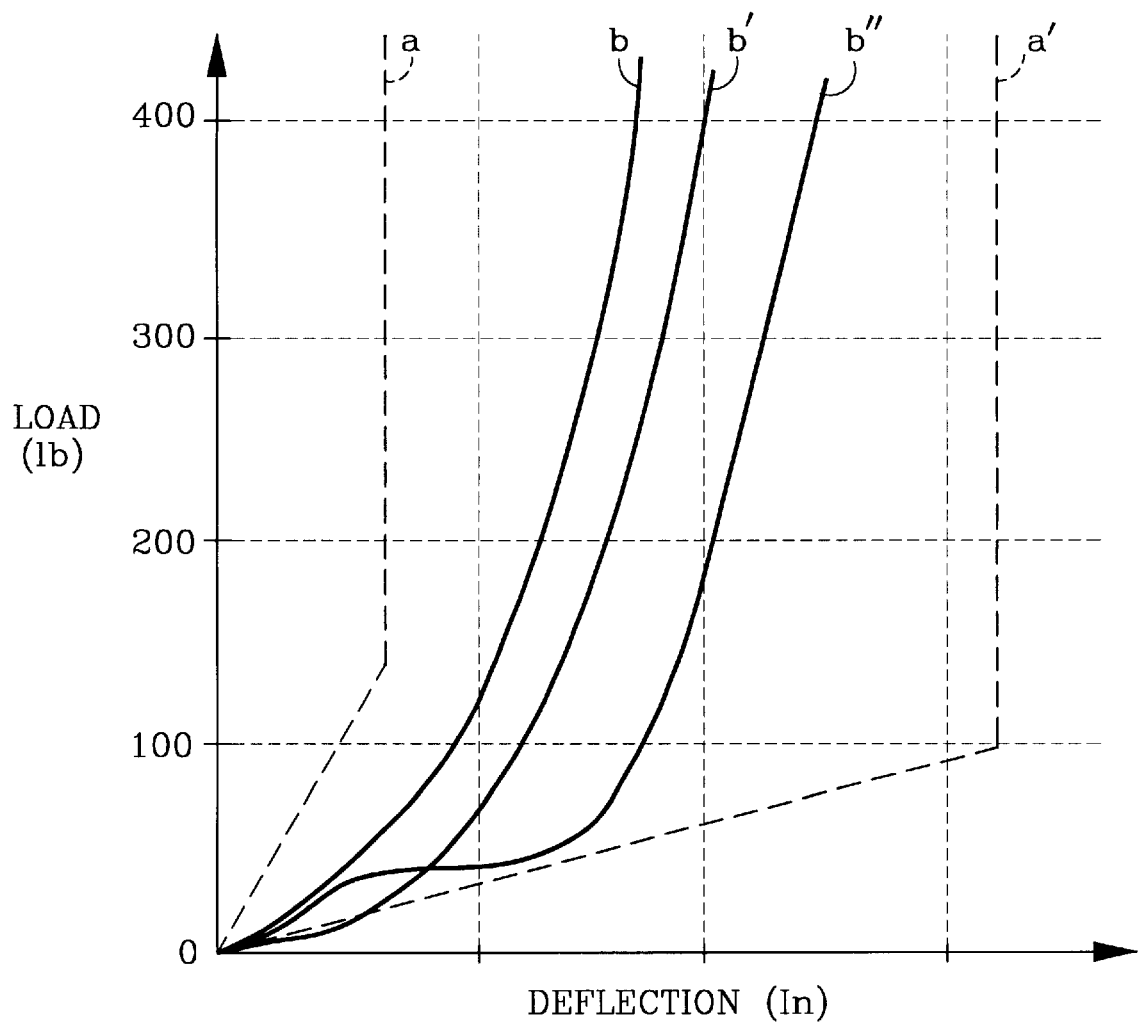
FIG. 53 is a graph showing the load-deflection characteristics of a prosthesis constructed in accordance with one embodiment of the present invention.

Referring to FIGS. 51a and 51b, depending upon the dimensions of the overall diameter, the aperture diameter, the thickness (t) and the height (h) of the conical shape of the Belleville spring 260, the Belleville spring can have a deflection response to increasing loads as illustrated by curves b, b', b' in FIG. 53. At height-to-thickness ratios, h/t, of approximately 3.0 and greater, the response curve resembles a divergent sinusoid (not shown), reflecting a negative loading and inversion of the spring from convex up 260a to concave up 260b (FIG. 51b). For purposes of the present embodiment, hit ratios of less than about 2.0 are desired for a non-sinusoidal response to increased loading. Springs 260 provided for use in the prosthesis 200 preferably offer a range of h/t ratios such that greater customization of the compliance of the prosthesis 200 is achieved.

Figure 52:
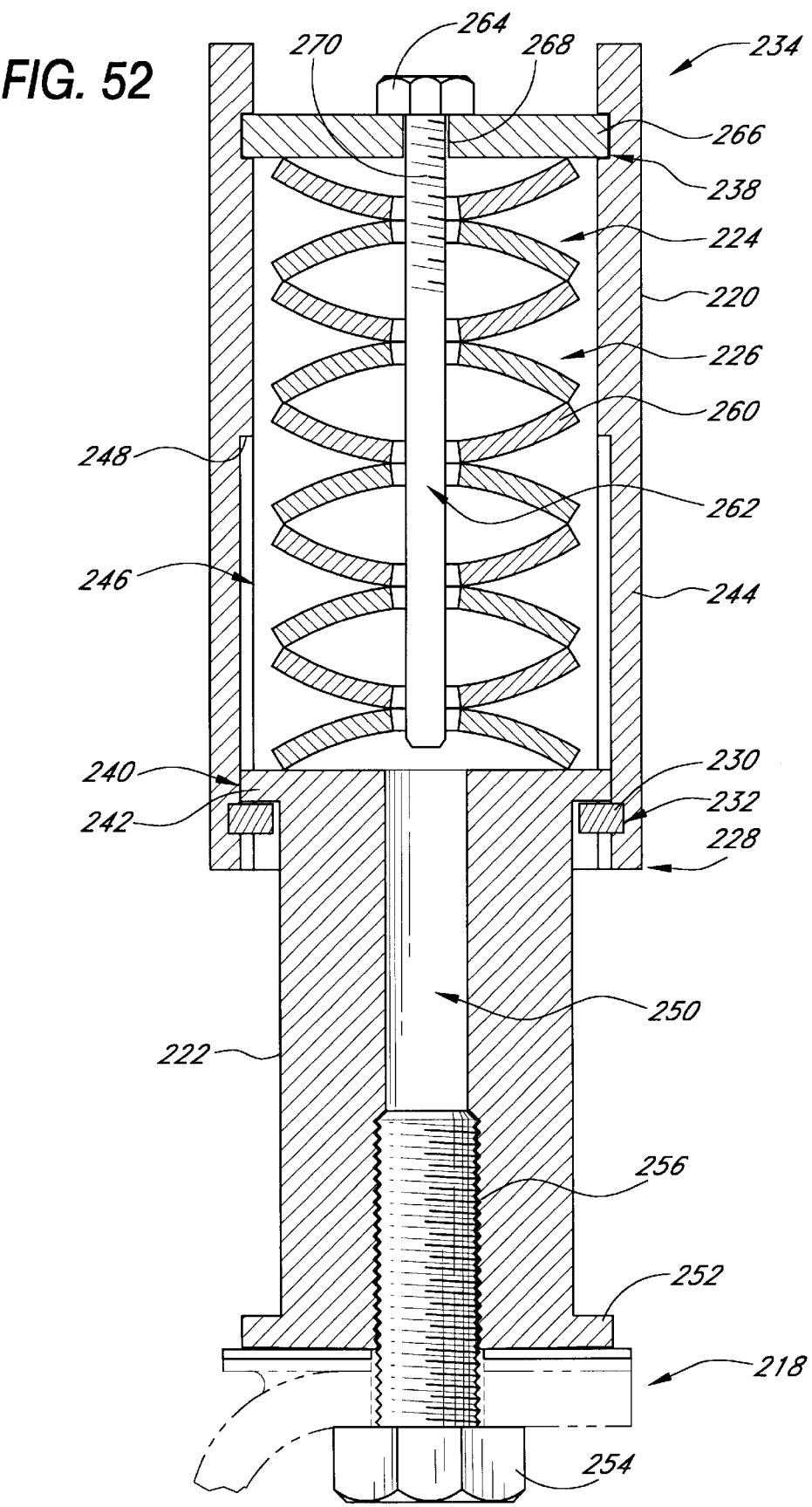
FIG. 52 is a longitudinal cross-section of an alternative embodiment of the shock absorbing pylon of FIG. 50.

Referring to FIG. 52, the aligning element 264 is used with a disk 266 having a threaded aperture 268. The bolt 264 includes a threaded portion 270 of its shaft extending a length at least equal to the thickness of the disk 266, although it need not be threaded along its entirety. The bolt length is such that upon full compression of the pylons 220, 222, the bolt 264 extends into the channel 250 but does not contact the mounting bolt 254.

The outer diameter of the compression member 224 is preferably such that under full compression there is no significant radial loading of the interior of the outer pylon 220. The inner diameter of the outer pylon 220 should be greater than the uncompressed outer diameter of the compression member 224 and may be the same as the outer diameter of the fully compressed member 224.

Load-Deflection Response

FIG. 53 illustrates a desired deflection response to increased loads that characterizes the compression member 224, 324 of the prosthesis 200, 300 of the present invention. The dashed lines a, a' indicate linear load-deflection responses from very stiff and very soft coil springs, respectively, while curves b, b', and b" indicate desirable responses provided by Belleville springs 260, or, alternatively, other compressible media. The nonlinear response of the prosthesis 200 is a characteristic of the compression member.

A comparison of the a, a' curves versus the b, b', and b" curves shows that a point of maximum deflection ($y_{max}$), or the point where there is no further deflection (y) in response to increased load (F), is achieved in a smoother, more gradual manner for the prosthesis 10 constructed in accordance with the present invention. Conventional compression springs have a linear characteristic a, a'($y=k \times F$, where k is the spring constant), terminating abruptly at point P (end of travel) wherein the maximum deflection of the spring occurs. The nonlinear curves b, b', b", on the other hand, show a smoother final transition to maximum deflection wherein the rate of change in slope toward infinity is more gradual than for the conventional springs.

Another embodiment of a vertical shock absorbing prosthesis 300 constructed in accordance with the present invention is illustrated in FIG. 54. A compression member 324 comprising a gas such as air is contained in a chamber 326 of an outer pylon 320. Alternatively, any compressible medium having a desired compression response to load may be utilized in the present embodiment. A piston-like inner pylon 322 transmits compressive loads to the member 324 and upper portion of the prosthesis 300 as it slides up and down as foot member 318 contacts with the ground. Any of the methods for retaining the inner pylon 322 within the outer pylon 320 as described above in connection with FIG. 50 may be utilized with the embodiment of FIG. 54. Similar elements from the embodiment 200 of FIG. 50 include a base portion 352 and a threaded portion 356 of a channel 350 of the inner pylon 322.

Preferably, the cylindrical outer pylon 320 has a proximal end 334 having an annular groove 338 formed on its interior. A disk 336 is sized for a close fit in the groove 338, and a sealing member or O-ring 337 is provided around the disk 336 and received in a secondary groove 339 formed in the disk groove 338. Alternatively, the secondary groove for the O-ring may be formed around the perimeter of the disk 336. Also, as previously described in connection with the embodiment of FIG. 50, a coating is preferably provided on at least the interior surface of the outer pylon 320 in order to minimize energy loss due to frictional contact between the inner and outer pylons 322, 320.

A cup-shape rubber seal 302 is preferably provided on top of a proximal portion 340 of the inner pylon 322. As the inner pylon 322 is pushed upward into the outer pylon 320 and the pressure of the gas 324 increases, pressure on the rubber seal 302 in a tighter seal between the inner and outer pylons 322, 320. Piston rings 304 positioned in annular grooves 306 around the exterior of the inner pylon 322 are utilized to provide additional sealing so that the gas or fluid 324 does not escape during use of the prosthesis 300. An annular element 330 on a distal end 328 of the outer pylon 320 limits the distal travel of the inner pylon 322.

As illustrated in FIG. 54, a one-way valve 308 is preferably located on the outer pylon 320, spaced below a proximal end 334 of the outer pylons 20 such that it does not prohibit attachment of a connector 212 (FIG. 49) such as described above. When the compressible medium 324 is a gas, the amputee can attach a gas cartridge to fill the prosthesis to a desired pressure before each use. A single cartridge may hold enough gas for several inflations of the prosthesis 300, as necessary. Alternatively, a pump may be used to pump air into the chamber 326.

In another embodiment utilizing a compressible medium, a piston head or disk (not shown) attached via a rod to either the outer or inner pylon and extending within the medium parallel to the upper end of the inner pylon may be utilized to provide clamping of to the sliding spring motion of the inner pylon. The disk would have a diameter substantially the same as the inner diameter of the outer pylon and include at least two one-way valves that limit flow between an upper and a lower chamber portion thus formed within the outer pylon of the prosthesis. The one-way valves may comprise ball or leaf valves or the like. The length of the rod attaching the disk may be equal to approximately one-quarter to one-half the uncompressed distance between the interior upper end of the outer pylon and the exterior upper end of the inner pylon so that motion therebetween is not obstructed.

Referring to FIG. 49, the vertical shock absorbing prosthesis 200, 300 of the present embodiments may be permanently or detachably mounted to upper and lower prosthetic members 212, 218. The construction of the prosthesis utilizing the pylons and compression member allows a range of combinations and customization for the amputee that can be obtained from a relatively small inventory of components. Thus, the prosthesis 200, 300 of the present invention allows a more natural feel and increased comfort through its performance characteristics and also provides additional or alternative control and adjustability for the amputee of its size and attachment.

Figure 55:
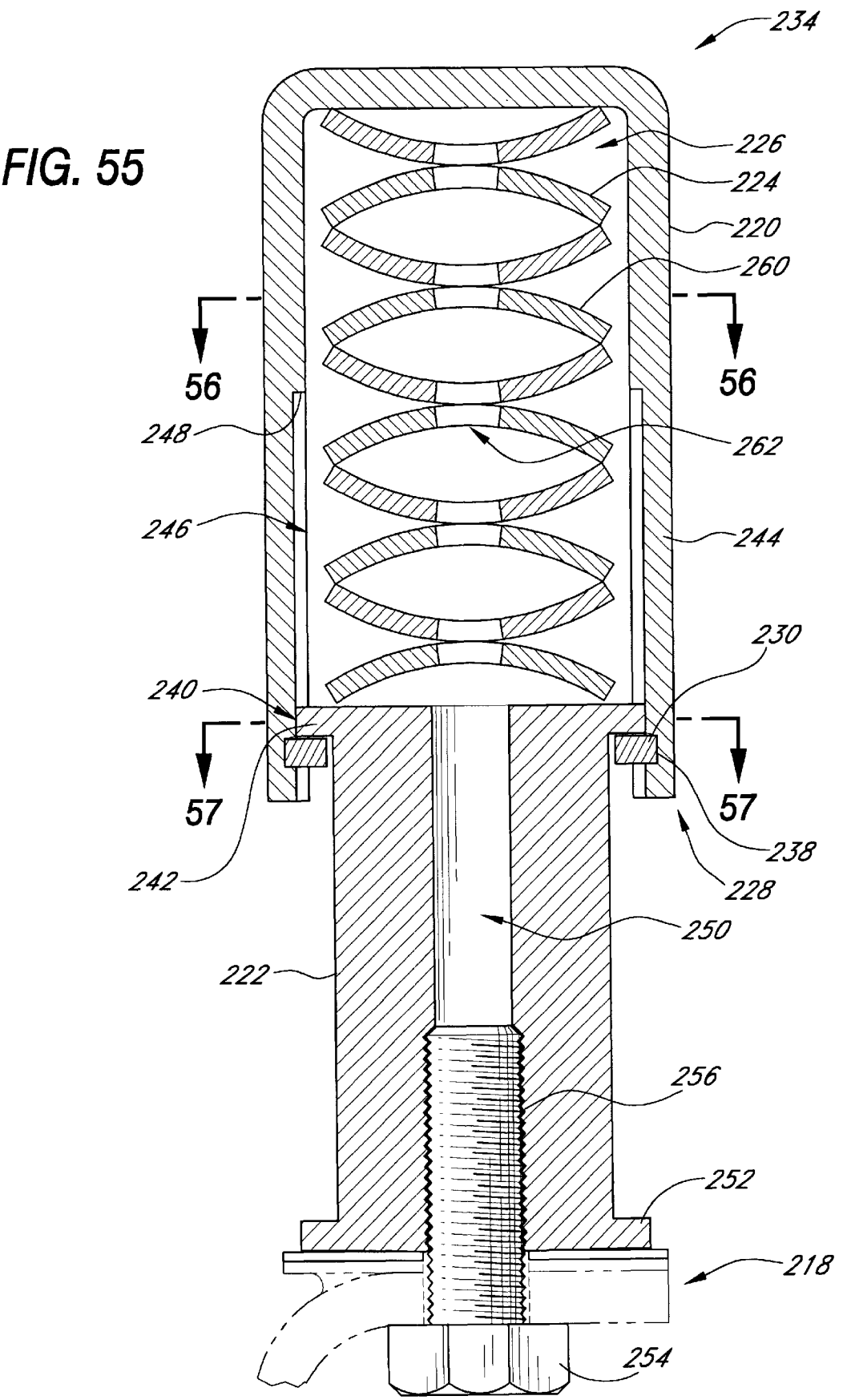
FIG. 55 is a longitudinal cross-section of another alternative embodiment of the prosthesis of the present invention.
Figure 56:
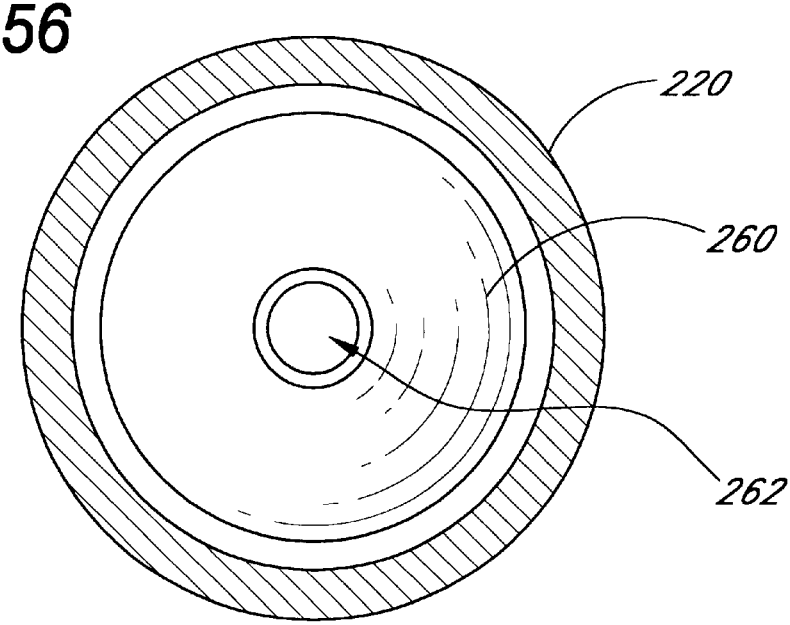
FIG. 56 is a cross-sectional view of the prosthesis of FIG. 55, taken along line 56—56.
Figure 57:
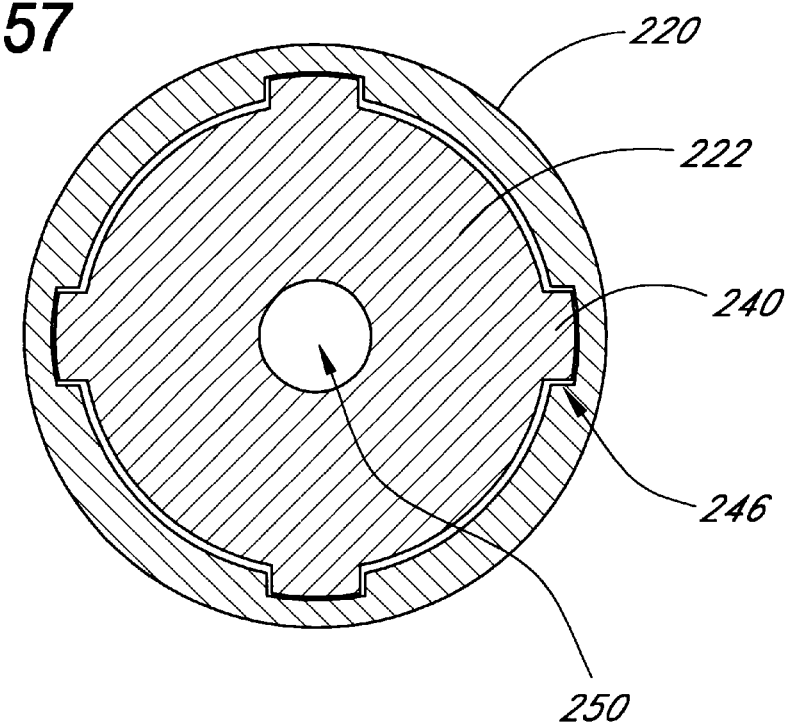
FIG. 57 is a cross-sectional view of the prosthesis of FIG. 55, taken along line 57—57.

FIGS. 55–57 illustrate an alternative shock absorbing prosthesis 200 similar to that shown in FIG. 50, with the outer pylon 220 having a sealed proximal end 214. FIG. 57 more particularly illustrates that the outer pylon 220 in one embodiment includes four longitudinal recesses 246 which correspondingly mate with four flanges 242 on the proximal end 240 of the inner pylon 222.

Figure 58:
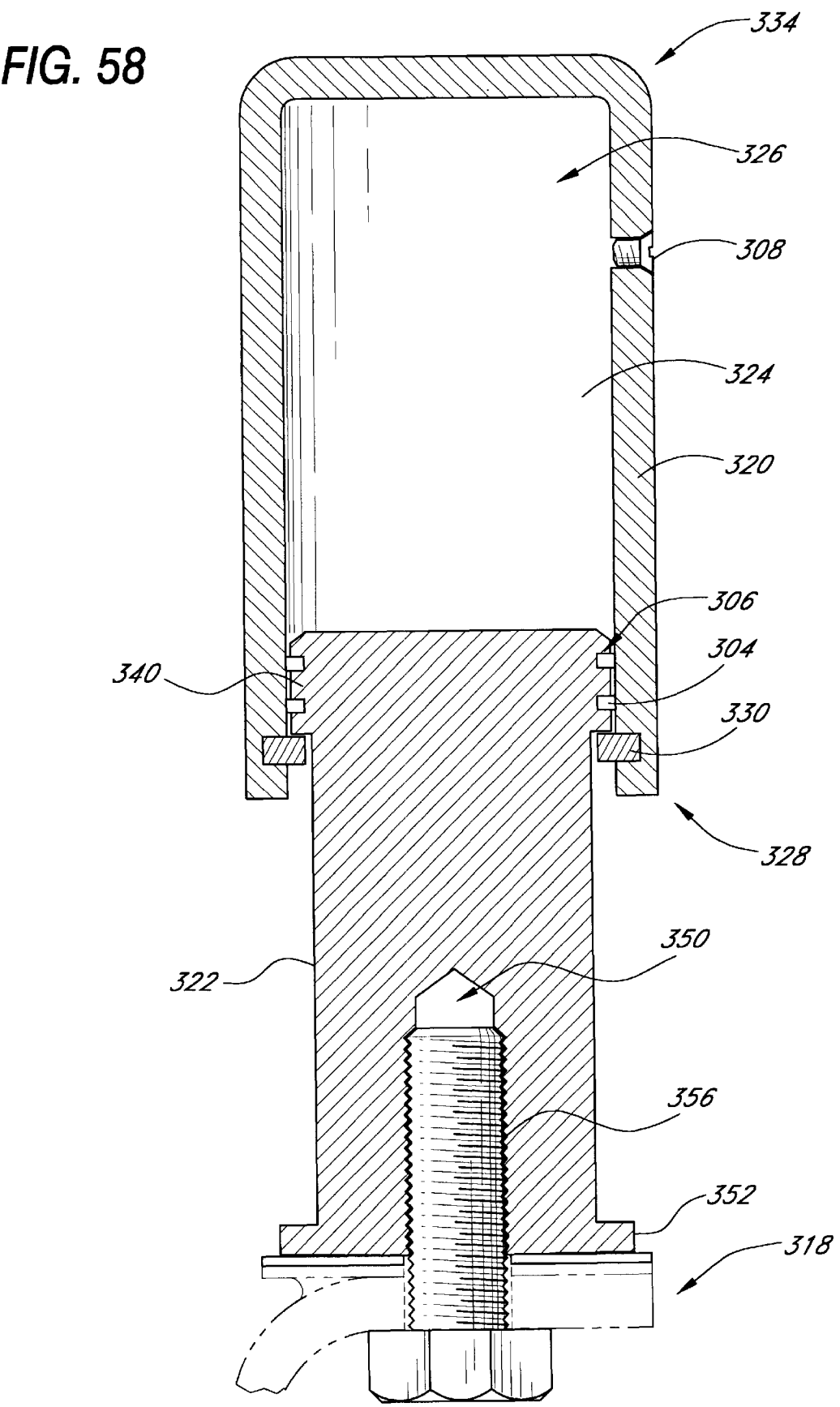
FIG. 58 is a longitudinal cross-sectional view of another alternative embodiment of the prosthesis of the present invention.

FIG. 58 illustrates an alternative shock absorbing prosthesis 300 similar to that shown in FIG. 54. In FIG. 58, the outer pylon 320 has a sealed proximal end 334. Furthermore, the proximal end of the inner pylon 322 is also sealed, such that channel 350 extends only partially trough the inner pylon. This thereby eliminates the need for the seal 302 of FIG. 54.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow.

What is claimed is:

1. An impact and torque absorbing prosthetic shock module, comprising:
   an outer pylon having a proximal end and a distal end, said outer pylon having at least one internally threaded surface;
   an inner pylon having a proximal end and a distal end telescopingly engaged with said outer pylon so that an annular interface is formed between said pylons, said inner pylon adapted to move axially and rotationally with respect to said outer pylon;
   a resilient element within said inner pylon having a proximal end and a distal end and being sized and configured to resist relative axial displacement of said pylons;
   a torque-resisting cuff connecting the pylons and providing torsional resistance to relative rotational motion between said pylons; and
   an internal support for said distal end of said resilient element, said internal support being threadingly engaged within said outer pylon.

2. The shock module of claim 2, wherein said resilient element further comprises a coil spring.

3. The shock module of claim 2, wherein said resilient element further comprises a compressible fluid in combination with said coil spring.

4. The shock module of claim 1, wherein said resilient element comprises a compressible fluid.

5. The shock module of claim 1, wherein said resilient element comprises a plurality of interconnected disks.

6. The shock module of claim 1, wherein said cuff has a proximal end connected to the proximal end of said inner pylon and a distal end connected to said proximal end of said outer pylon.

7. An impact and torque absorbing prosthetic shock module, comprising:
   an outer pylon having a proximal end and a distal end;
   an inner pylon having a proximal end and a distal end telescopingly engaged with said outer pylon so that an annular interface is formed between said pylons, said inner pylon adapted to move axially and rotationally with respect to said outer pylon;
   a resilient element within said inner pylon having a proximal end and a distal end and being sized and configured to resist relative axial displacement of said pylons;
   a torque-resisting cuff connecting the pylons and providing torsional resistance to relative rotational motion between said pylons; wherein
   said cuff has a proximal end connected to the proximal end of said inner pylon and a distal end connected to said proximal end of said outer pylon; and wherein the shock module further comprises ring clamps that clamp said cuff to said pylons and provide air tight seals with respect to the entire circumference of said pylons.

8. The shock module of claim 1, wherein the proximal end of the inner pylon has an enlarged outside diameter corresponding generally to the outside diameter of the outer pylon.

9. The shock module of claim 1, wherein the proximal ends of the inner and outer pylons include grooves for engaging said cuff.

10. The shock module of claim 1, wherein said internal support has a proximal end and a distal end, the distal end being externally threaded to engage with said outer pylon.

11. The shock module of claim 1, further comprising an end cap threadingly engaged with said outer pylon below said internal support.

12. The shock module of claim 11, further comprising an O-ring between the end cap and the spring support.

13. The shock module of claim 1, wherein said outer pylon includes two internally threaded surfaces, said first surface threadingly engaging said internal support and an end cap, and said second surface threadingly engaging a cover cap below said end cap.

14. The shock module of claim 13, further comprising an O-ring between the cover cap and the end cap.

15. The shock module of claim 1, wherein said proximal end of said inner pylon is attachable to a socket for receiving a stump of an amputee, and said distal end of said outer pylon is attachable to a prosthetic foot.

16. The shock module of claim 7, further comprising an internal support for said distal end of said resilient element, said internal support being threadingly engaged within said outer pylon.

17. The shock module of claim 7, wherein said resilient element further comprises a coil spring.

18. The shock module of claim 17, wherein said resilient element further comprises a compressible fluid in combination with said coil spring.

19. The shock module of claim 7, wherein said resilient element comprises a compressible fluid.

20. The shock module of claim 7, wherein said resilient element further comprises a plurality of interconnected disks.

21. The shock module of claim 7, wherein the proximal end of the inner pylon has an enlarged outside diameter corresponding generally to the outside diameter of the outer pylon.

22. The shock module of claim 7, wherein the proximal ends of the inner and outer pylons include grooves for engaging said cuff.

23. The shock module of claim 16, wherein said internal support has a proximal end and a distal end, the distal end being externally threaded to engage with said outer pylon.

24. The shock module of claim 16, further comprising an end cap threadingly engaged with said outer pylon below said internal support.

25. The shock module of claim 24, further comprising an O-ring between the end cap and the spring support.

26. The shock module of claim 16, wherein said outer pylon includes two internally threaded surfaces, said first surface threadingly engaging said internal support and an end cap, and said second surface threadingly engaging a cover cap below said end cap.

27. The shock module of claim 26, further comprising an O-ring between the cover cap and the end cap.

28. The shock module of claim 7, wherein said proximal end of said inner pylon is attachable to a socket for receiving a stump of an amputee, and said distal end of said outer pylon is attachable to a prosthetic foot.

* * * * *